(12) United States Patent
Rajashekara et al.

(10) Patent No.: US 8,075,879 B2
(45) Date of Patent: Dec. 13, 2011

(54) BRUCELLA MELITENSIS MUTANTS AND METHODS

(75) Inventors: Gireesh Rajashekara, Madison, WI (US); Gary Splitter, Brooklyn, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 12 days.

(21) Appl. No.: 12/580,213

(22) Filed: Oct. 15, 2009

(65) Prior Publication Data

US 2010/0158954 A1   Jun. 24, 2010

Related U.S. Application Data

(63) Continuation of application No. 11/633,371, filed on Dec. 1, 2006, now abandoned.

(60) Provisional application No. 60/741,282, filed on Dec. 1, 2005.

(51) Int. Cl.
*A61B 5/055* (2006.01)

(52) U.S. Cl. .................. 424/93.2; 424/93.1; 424/252.1; 435/252.1

(58) Field of Classification Search .................. None
See application file for complete search history.

(56) References Cited

U.S. PATENT DOCUMENTS 5,830,702 A   11/1998   Portnoy et al.

FOREIGN PATENT DOCUMENTS

WO   WO 2005/084706   9/2005

OTHER PUBLICATIONS

Alton et al. (1967) "*Brucella melitensis* Vaccine. The Stability of the Degree of Attenuation," *J. Comp. Pathol.* 77:293-300.
Anderson et al. (Apr. 2006) "CGHScan: Finding Variable Regions Using High-Density Microarray Comparative Genomic Hybridization Data," *BMC Genomics* 7:91-98.
Blasco, J.M. (1997) "A Review of the Use of *B. melitensis* Rev 1 Vaccine in Adult Sheep and Goats," *Prev. Vet. Med.* 31:275-283.
Boschiroli et al. (Feb. 2002) "The *Brucella suis* virB Operon is Induced Intracellularly in Macrophages," *Proc. Nat. Acad. Sci. USA* 99:1544-1549.
Braun et al. (1947) "Independent Variation of Characteristics in *Brucella abortus* Variants and Their Detection," *Am. J. Vet. Res.* 8:386-390.
Comerci et al. (2001) "Essential Role of the virB Machinery in the Maturation of the *Brucella abortus*-Containing Vacuole," *Cell. Microbiol.* 3:159-168.
Contag et al. (1995) "Photonic Detection of Bacterial Pathogens in Living Hosts," *Mol. Microbiol.* 18:593-603.
DelVecchio et al. (2002) "The Genome Sequence of the Facultative Intracellular Pathogen *Brucella melitensis*," *Proc. Nat. Acad. Sci. USA* 99:443-448.
Elberg et al. (1957) "Immunization Against *Brucella* Infection. VI. Immunity Conferred on Goats by a Nondependent Mutant from a Streptomycin-Dependent Mutant Strain of *Brucella melitensis*," *J. Bacteriol.* 73:211-217.
Fry et al. (2000) "The *galE* Gene of *Campylobacter jejuni* is Involved in Lipopolysaccharide Synthesis and Virulence," *Infect. Immun.* 68:2594-2601.
Grode et al. (Sep. 2005) "Increased Vaccine Efficacy Against Tuberculosis of Recombinant *Mycobacterium bovis* Bacile Calmette-Guerin Mutants that Secrete Listeriolysin," *J. Clin. Invest.* 115(9):2472-2479.
Henderson et al. (Mar. 2001) "Virulence Functions of Autotransporter Proteins," *Infect. Immun.* 69(3):1231-1243.
Hone et al. (1987) "Construction of Defined *galE* Mutants of *Salmonella* for Use as Vaccines," *J. Infect. Dis.* 156:167-174.
Hong et al. (2000) "Identification of Genes Required for Chronic Persistence of *Brucella abortus* in Mice," *Infect. Immun.* 68:4102-4107.
Kimoto et al. (May 2003) "Differences in Gama Interferon Production Induced by Listeriolysin O and Ivanolysin O Result in Different Levels of Protective Immunity in Mice Infected with *Listeria monocytogenes* and *Listeria ivanovii*," *Infect. Immun.* 71(5):2447-2454.
Ko et al. (2002) "Virulence Criteria for *Brucella abortus* Strains as Determined by Interferon Regulatory Factor 1-Deficient Mice," *Infect. Immun.* 70:7004-7012.
Ko et al. (2003) "Molecular Host-Pathogen Interaction in Brucellosis: Current Understanding and Future Approaches to Vaccine Development for Mice and Humans," *Clin. Microbiol. Rev.* 16:65-78.
Kovach et al. (1995) "Four New Derivatives of the Broad-Host-Range Cloning Vector pBBr1MCS, Carrying Different Antibiotic-Resistance Cassettes," *Gene* 166:175-176.
Lapaque et al. (2005) "*Brucella* Lipopolysaccharide Acts as a Virulence Factor," *Curr. Opin. Microbiol.* 8:60-66.

(Continued)

*Primary Examiner* — Patricia A Duffy
(74) *Attorney, Agent, or Firm* — Greenlee Sullivan P.C.

(57) ABSTRACT

Certain attenuated mutants of *Brucella*, especially *B. melitensis, B. abortus, B. suis* and *B. ovis*, when administered to a human or animal trigger a protective immune response such that subsequent challenge with virulent *Brucella* of the same species does not result in disease or results in much less severe symptoms. Functional inactivation of galE, a virB gene or the operon (ORFs 1087-1090) comprising the gene encoding β-hexosaminidase (BMEI1087) and a lytic murein transglycosylase gene (BMEI1088). A specific example of the attenuated galE mutant which produces a protective immune response is *B. melitensis* GR024. The specific example of an inactivated ORF1087-1090 operon is *B. melitensis* GR026; it has an insertion mutation in the promoter region upstream of ORF 1090. Vaccination with live cells of either or both of these mutants results in a T cell response which protects the human or animal against challenge with virulent *B. melitensis*. Similar strategies for protective immunity using live attenuated mutants are useful for *B. abortus, B. suis* and *B. ovis* as well.

9 Claims, 15 Drawing Sheets
(4 of 15 Drawing Sheet(s) Filed in Color)

OTHER PUBLICATIONS

Lestrate et al. (2000) "Identification and Characterization of in vivo Attenuated Mutants of *Brucella melitensis*," *Mol. Microbiol.* 38:543-551.

Maskell et al. (1992) "The gal Locus from *Haemophilus influenzae*: Cloning, Sequencing and the Use of gal Mutants to Study Lipopolysaccharide," *Mol. Microbiol.* 6:3051-3063.

Monreal et al. (Jun. 2003) "Characterization of *Brucela abortus* O-Polysaccharide and Core Lipopolysaccharide Mutants and Demonstration that a Complete Core is Required for Rough Vaccines to be Efficient Against *Brucella abortus* and *Brucella ovis* in the Mouse Model," *Infect. Immun.* 71:3261-3271.

Monriyon et al. (2004) "Rough Vaccines in Animal Brucellosis: Structural and Genetic Basis and Present Status," *Vet. Res.* 35:1-38.

Moreno et al. (Jan. 8, 2002) "*Brucella melitensis*: A Nasty Bug with Hidden Credentials for Virulence," *Proc. Nat. Acad. Sci. USA* 99(10):1-3.

Pei et al. (Jun. 2004) "*Brucella abortus* Rough Mutants are Cytopathic for Macrophages in Culture," *Infect. Immun.* 72:440-450.

Petrovska et al. (1999) "*Brucella melitensis* 16M: Characterization of the *galE* Gene and Mouse Immunization Studies with *galE* Deficient Mutant," *Vet. Microbiol.* 65:21-36.

Pierson et al. (Oct. 1996) "Identification of the *galE* Gene and a *galeE* Homolog and Characterization of Their Roles in the Biosynthesis of Lipopolysaccharide in a Serotype O:8 Strain of *Yersinia enterocolitica*," *J. Bacteriol.* 178:5916-5924.

Rajashekara et al. (2005) "Temporal Analysis of Pathogenic Events in Virulent and Avirulent *Brucella melitensis* Infections," *Cellular Microbiol.* 10:149-1473.

Rajshekara et al. (Aug. 2004) "Comparative Whole-Genome Hybridization Reveals Genomic Islands in *Brucella* Species," *J. Bacteriol.* 186(15):5040-5051.

Rajashekara et al. (May 2006) "Attenuated Bioluminescent *Brucella melitensis* Mutants GR019 (*virB4*), GR024 (*galE*), and GR026 (BMEI1090-BMEI1091) Confer Protection in Mice," *Infect Immun.* 74(5):2925-2936.

Rittig et al. (2003) "Smooth and Rough Lipopolysaccharide Phenotypes of *Brucella* Induce Different Intracellular Trafficking and Cytokine/Chemokine Release in Human Monocytes," *J. Leukoc. Biol.* 74:1045-1055.

Robertson et al. (1993) "The Role of *galE* in the Biosynthesis and Function of Gonococcal Lipopolysaccharide," *Mol. Microbiol.* 8:891-901.

Schurig et al. (2002) "Brucellosis Vaccines: Past, Present and Future," *Vet. Microbiol.* 90:479-496.

Scupham et al. (1997) "Isolation and Characterization of the UDP-glucose4'-epimerase-encoding Gene, *galE*, from *Brucella abortus* 2308," *Gene* 202:53-59.

Young, E.J. (1995) "An Overview of Human Brucellosis," *Clin. Infect. Dis.* 21:283-289.

Prosecution History for parent application, U.S. Appl. No. 11/633,371.

A
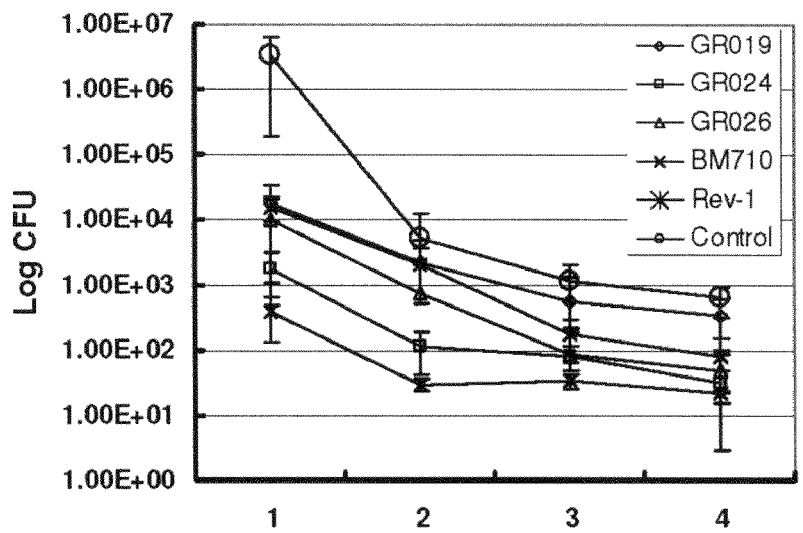
B
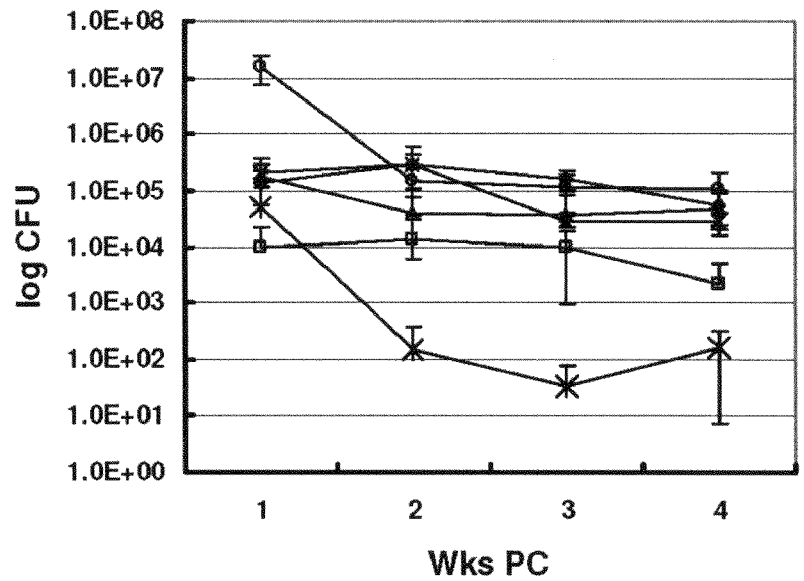
Wks PC
Figure 8

FIG. 11

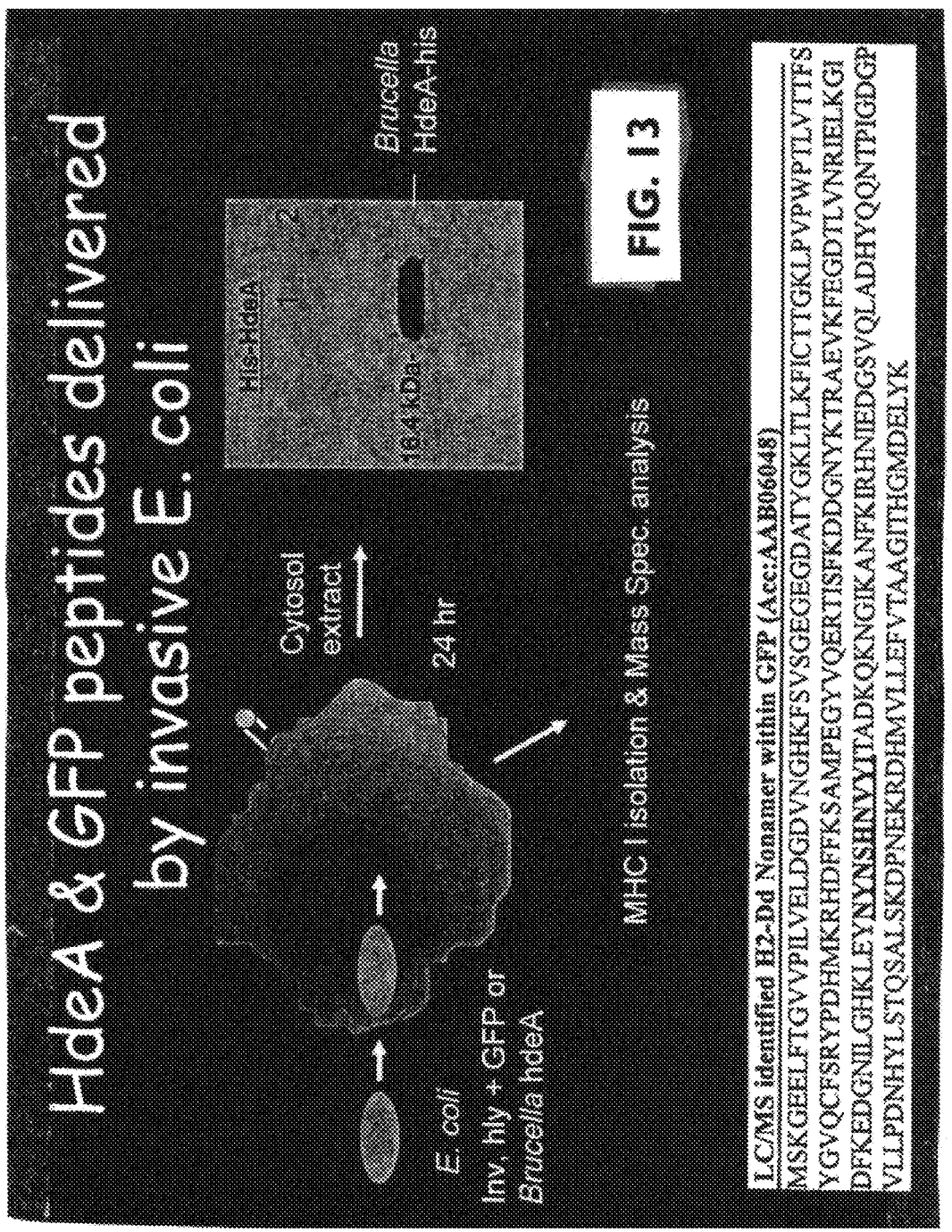

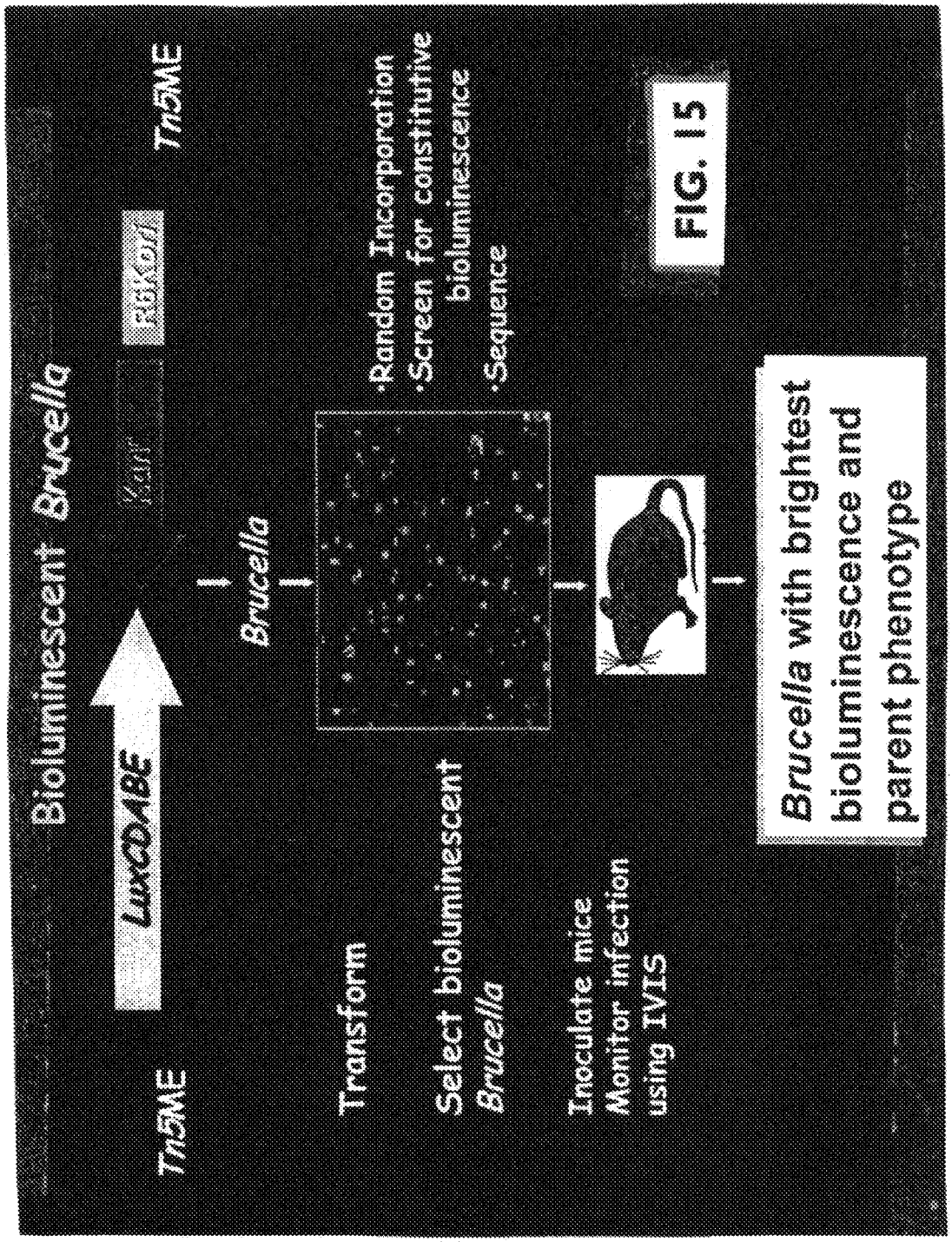

SEQUENCE LISTING

```
<160> NUMBER OF SEQ ID NOS: 29

<210> SEQ ID NO 1
<211> LENGTH: 32
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 1
atcaacggta cccgttcagc gcgtcgagat cg                                32

<210> SEQ ID NO 2
<211> LENGTH: 33
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 2
gctctaggat ccgactgata attatgccgt gcg                               33

<210> SEQ ID NO 3
<211> LENGTH: 33
<212> TYPE: DNA
<213> ORGANISM: Artificial sequence
<220> FEATURE:
<223> OTHER INFORMATION: Synthetic:  oligonucleotide useful as a
      primer.
```

-continued

```
<400> SEQUENCE: 3
acagtcggat ccataaccga agcctattcc ttc                                    33

<210> SEQ ID NO 4
<211> LENGTH: 30
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 4
ggtaacctgc agcgaacgtg cccgcatcat                                        30

<210> SEQ ID NO 5
<211> LENGTH: 32
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 5
agatacggta cctcttccat cgttccgggc ct                                     32

<210> SEQ ID NO 6
<211> LENGTH: 34
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 6
catgcatcta gagacgccgt tgatgttcca tgta                                   34

<210> SEQ ID NO 7
<211> LENGTH: 28
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 7
tcttgagaat tccccaatgc gaccgctt                                          28

<210> SEQ ID NO 8
<211> LENGTH: 31
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 8
gattcagaat tctttggcga tccgcctggc a                                      31

<210> SEQ ID NO 9
<211> LENGTH: 35
<212> TYPE: DNA
<213> ORGANISM: Artificial sequence
<220> FEATURE:
<223> OTHER INFORMATION: Synthetic:  oligonucleotide useful as a
      primer.

<400> SEQUENCE: 9
```
agagagggta cccatgttca tattgccgct gatcg        35

<210> SEQ ID NO 10
<211> LENGTH: 35
<212> TYPE: DNA
<213> ORGANISM: Artificial sequence
<220> FEATURE:
<223> OTHER INFORMATION: Synthetic: oliognucleotide useful as a
      primer.

<400> SEQUENCE: 10
agagagggat cctgctggtt acagtcaggg cgaat        35

<210> SEQ ID NO 11
<211> LENGTH: 35
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 11
agagagggta ccaaagcccg gtaaaacgat tgatg        35

<210> SEQ ID NO 12
<211> LENGTH: 33
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 12
agagagggat ccgttccggc attttctggc aaa        33

<210> SEQ ID NO 13
<211> LENGTH: 32
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 13
agagagacta gttgtgccgt cgtttccacc tg        32

<210> SEQ ID NO 14
<211> LENGTH: 32
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 14
agagagctcg agagggacgg ggatcgggtt at        32

<210> SEQ ID NO 15
<211> LENGTH: 20
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 15
gctcgaggcc gcgattaaat        20

-continued

```
<210> SEQ ID NO 16
<211> LENGTH: 22
<212> TYPE: DNA
<213> ORGANISM: Artificial sequence
<220> FEATURE:
<223> OTHER INFORMATION: Synthetic: oligonucleotide useful as a
      primer.

<400> SEQUENCE: 16
tcaccgaggc agttccatag ga                                          22

<210> SEQ ID NO 17
<211> LENGTH: 9
<212> TYPE: PRT
<213> ORGANISM: Artificial sequence
<220> FEATURE:
<223> OTHER INFORMATION: Synthetic: peptide from Brucella-infected
      Raw264.7 cells.

<400> SEQUENCE: 17

Asn Tyr Asn Ser His Asn Val Tyr Ile
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic: peptide from Brucella-infected
      Raw264.7 cells.

<400> SEQUENCE: 18

His Tyr Leu Ser Thr Gln Ser Ala Leu
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic: peptide from Brucella-infected
      Raw264.7 cells.

<400> SEQUENCE: 19

Leu Phe Thr Gly Val Val Pro Ile Leu
1               5

<210> SEQ ID NO 20
<211> LENGTH: 9
<212> TYPE: PRT
<213> ORGANISM: Artificial sequence
<220> FEATURE:
<223> OTHER INFORMATION: Synthetid: peptide from Brucella-infected
      Raw264.7 cells.

<400> SEQUENCE: 20

Lys Phe Ile Cys Thr Thr Gly Lys Leu
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic: peptide from Brucella-infected
      Raw264.7 cells.

<400> SEQUENCE: 21
```

-continued

Asp Phe Lys Glu Asp Gly Asn Ile Leu
1               5

<210> SEQ ID NO 22
<211> LENGTH: 9
<212> TYPE: PRT
<213> ORGANISM: Artificial sequence
<220> FEATURE:
<223> OTHER INFORMATION: Synthetic:  peptide from Brucella-infected
      Raw264.7 cells.

<400> SEQUENCE: 22

Leu Pro Val Pro Trp Pro Thr Leu Val
1               5

<210> SEQ ID NO 23
<211> LENGTH: 9
<212> TYPE: PRT
<213> ORGANISM: Artificial sequence
<220> FEATURE:
<223> OTHER INFORMATION: Synthetic:  peptide from Brucella-infected
      Raw264.7 cells.

<400> SEQUENCE: 23

Glu Tyr Asn Tyr Asn Ser His Asn Val
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic:  peptide from Brucella-infected
      Raw264.7 cells.

<400> SEQUENCE: 24

Thr Pro Ile Gly Asp Gly Pro Val Leu
1               5

<210> SEQ ID NO 25
<211> LENGTH: 10
<212> TYPE: PRT
<213> ORGANISM: Artificial
<220> FEATURE:
<223> OTHER INFORMATION: Synthetic construct:  peptide.

<400> SEQUENCE: 25

Asn Tyr Asn Ser His Asn Val Tyr Ile Thr
1               5                   10

<210> SEQ ID NO 26
<211> LENGTH: 10975
<212> TYPE: DNA
<213> ORGANISM: Brucella melitensis

<400> SEQUENCE: 26
aggctgccat tgctcaaaat caatgcaact gaagccgttc cgacaaaagc gcgaagcggt      60 ttttggaat catcctcaaa caaaatcttg gagcgggatg atggttggac ttaaattcaa     120
cccgttttag agcgcgtttc gatctgattg aatcagatcg gcgctctaat cctttgtttt     180
gacgcgcatc ttttccgaaa accgtttcac acttttcggg atgcgctcta agaacggaa     240 gacgtgcctt cgatgaacgg ctgatatcga accggcatga ggtcttcctg ttcaaaacgg     300
cttccaacct ttgaaatccg cgtcatgatc tggcgtccat cgccagggcc gatcggggct     360
atcaggacgc catgggtggc gagcagttca acgaaatggc gcggcacctc atcgcatgcg     420

```
agccagatga caatgcggtc aaacggcccg cccggcatac cgtggcgccc gtctgtatgt    480
ttcaccatga tattctcgcg cttcagcgaa acgaactgct ggagagcgtg gtcgcagagt    540
tttcgatacc gttccaccgt cgttacacgg ccggacagca aggacataac ggcggcggta    600
aagccggagc cggtgccgat ttccagaacc cgatggccgg gctcaagctt cagggcggaa    660
atgacgcgcg cctgatcgtc tatgccttcc atatattcac cgcaatcaag ggcgcggtt    720 cgcgggctat aggcaagatg cgaccatgcc gccgccagaa agctctggcg cggcgttgct    780
tcaattgccg caaaaagttg cggatcatca atgctgtgcc cacgcatccg cagaacaaag    840
gatgcaaatc cctcccggtc cgaaagccgc gggcgttcag acgttgcctg cctcatgctt    900
ccactccaag cgccgcgccc agttctgcac gaaccttatg agcggtcaga tcaaggtgga    960
gtggggtcac tgaaatgcaa cccgaacgga tggcagcaat atcgctgtcg tcggcaaccg   1020
gagccttgcc gcgaccgaaa tgcagccaga aataagggaa accacgtcca tcgcggcgct   1080
cgtcaaggcg cgcatcatgg ctaagcttgc cttgtgccgt gacgcgcacg cccttcactt   1140
cttccggagc gcaattcggg aaattgaggt tcaacagcac gccttccggc cagcccgcct   1200
ccatcagcct cccgataagc tcaggcgcat gagcttccgc cgtttcccac ggcacgatcc   1260
ggcgatcgcc cgcatattca tattcctgcg acaaagcgat ggctcgcaca ccaagcaatg   1320 tccctccat cgcaccggca accgtgcccg aataggtcac atcgtcggcc atgttcgccc   1380
cggaattgac gccggagagg acgagatcgg gcgcgcccgg caatacatgg cgcacccca   1440 tgatgacgca atcggtcgga gtgccgcgca gggcaaaatg acgggcatcg atctggcgaa   1500
ggcgaagcgg ctccgacagt gtcagtgagt gggcaagccc gctctggtcc gtttcagggg   1560
ccaccaccca cacatcgtcg gagagcttgc gtgcaattcg ctccagaaca gcgaggcctt   1620
cagcgtggat accgtcatcg ttcgtcagca gaatacgcaa tttgtcactc cttcgccgaa   1680
atggataaga cacttaagac actacagcgg ttccagttga atgggatcg ttgaaactgc   1740 tctctctttg ttctttcgca tgtccccaaa accggttccc acttttgggg gcatgctata   1800
attccagatc aagcggcttt ttcgatccgc gtgaggccgc ccatatatgg ctgtaatgct   1860
tcaggaatat gaatgctgcc gtcttcctgc tggtaatttt ccataaccgc aatcagcgcg   1920
cgcccgacag cagcgcccga cccgttgagg gtgtgcacga agcgcgtgga ttttcgcct   1980 tccgggcgat agcgggcatt catgcggcgg ccctggaaat caccgcaggt cgaacagctt   2040
gaaatttcgc gataggtgtt ctgccccggc aaccagacct cgatatcata ggtccgctgt   2100
gcgccaaagc ccatgtcgcc cgtgcaaagc acaacggtac ggaacggcag gcccagccgc   2160
ttcagcactt cttccgcgca agccgtcatg cgctcatgct cggcaacgga gctttccgca   2220
tcggtgatcg ataccatctc cactttcagg aactgatgct ggcgcaacat gccgcgcgta   2280
tcgcgcccgg ccgaccccgc ttccgagcga aaacatgggg tcagcgccgt gaagcgcagc   2340 ggcagccct tcatatcgac aatttcttcg gcaaccagat tggtgagcgg cacctccgcc   2400
gtcgggatca gccagcggcc atccgtcgtg cggaaaagat cttctgaaaa cttcggcaat   2460
tgccccgtgc catagaccgc ttcgtcgcgc accatcagcg gcggcatgac ttcggtataa   2520
ccgtgttctg tcgtgtgaag atcgagcatg aactggccaa gcgcgcgctc aagacgggcg   2580
agcgggcctt tcagcaccgt aaagcgcgca ccggcaagct tggccgcgcg ctcgaaatcc   2640
atgtatccaa gcgcctcgcc aagctcaaaa tgctctttcg gctggaagga gaaattgtgc   2700
gggttgccaa tgcggcgcag ctcaacattg tcgctttcat ccttgccgag cggcacatca   2760
tcaagcggaa tattgggaat ggtggacaat gcgtcgctca gttccttgct gaggcggcgc   2820
```

```
tcgtcttctt ccgcatgggc gagaaaatct ttcagttcgc ccacttcggc cttcagcttt   2880
tcagccgtgc ccatgtcctt tgcggccatg gccttgccga tttccttcga ggcggcattg   2940
cggcgctcct gcgctgcctg caccttgccg acatgctcgc ggcgcttttc atccagcgca   3000
atcagttcgg acgaaagcgg agcagcccca cgctttgcga cgcccttgtc gagggtttcc   3060
gggttttcgc gaatccattt gatgtcgagc atggaaaaaa gccatttcgt gaaattgaac   3120
agaagcgagg ctaaacgatc ttcagcccca aagatgcctg acgtcagatc aggtggagga   3180
agcgttgtta tcagcgtcgg cagatgcctg cgcctcatcc cgcttcttct cgatcatgcg   3240
cgccagaaag atcgaaatct cgtaaagaag atcgtcggc aaggcaagac cgatctggct   3300
cgccgggtcc ggcggggtca gcaccgcagc cgcgacgaag gcaatgacga tcgcatattt   3360
gcgcttgtcc ttcagccccg ccgaagtcac cagccccaca cgcgccatga ggctcgtcac   3420
caccggcaac tggaagacca ggccaaaagc aaagatgagc gtcatgatga ggctcagata   3480
ttccgacact tcggcagaa gcgaaatctg gacctcgccg ctgccgccgg tctgctgcat   3540
ggcgaggaag aaccacatca ccatgggcgt gaaaaagaaa tagacgagcg cgccgccgat   3600
caggaacaga tgggcgacg cgatcaggaa cggcagaaat gcagtgcgtt cgtgcttgta   3660
gagaccggga gccacgaatt tataaatctg tgcggcgatg accgggaggg ccagcacaat   3720
gccgccgaac atgccaccct tcacctgcgt gaagaagaat tcctgaggtg cggtatagat   3780
caattccgcc ttggagcggt ccatgccggc ccagtcgatg gcccattgat acggcaccac   3840
aagcaggttg aagagctgtt ttgcgaaagc aaagcagaaa atgaatgcca cgaaaaaagc   3900
caggatagcc caaataaggc ggcggcgcag ttcgatcagg tgttcaagca gaggcgctgc   3960
gctctgttcg atttcatcct cgtcccggtt cacgctttgg ttcctgtctt ctttgtggtc   4020
tttttaaccg gcgttgcggt cttgtctgcc gtcggcttgg gggtagctcc ggttttttg   4080 gcagtctttg tcgtcgtcgg tttcggcccg gcttttgcag ccggacgcgg tgatgttttc   4140
ctaggcttgg cgggttcttc gggcgcgtg atcattggta cgggaactgg cggcgcggga   4200
actggcgttc cgcccggctc aaccggcgtc gtaacctcac ccaccttgtt ctcggtgact   4260
ggcgacattg atgttgcgga ctggagacca gaccgcaaat cctcgccagc actgcgaatc   4320
gggtcaaaaa cctgtgtcag ccttgtgcgc ggatcaaggc ttctggcttc atcgatgatg   4380
gtcttgacgt cttcaagttc cgcctcttc aaggcctcgt tgaattgatg gcgaaactcg   4440
ttggcggtgg tgcgcatgcg tgcagtcgcc ttgccgaacg cgcgaagcat tttcggcaaa   4500
tccttgggac cgaccaccac aatcatgaca attgcgataa tcagcagttc agaccaagcg   4560
atatcgaaca taatttgata ccttgcgctc tgcgcgcaca tcctgtctct tggcgaaaag   4620
ccgcactgcc cacaaacctg ccatgcgcgt tttcagccca tggcagttca tcccggaagg   4680
atcaggactt ggtggtcttc ttgacgtcct tgacgggttc ttccgctttg gcgtcgatcg   4740
tacgcggatc ttccttggcg tcttcgtcag ccatgccctg cttaaaattc ttgatacccg   4800
tggcgacatc gcccatcagc tcggggatct tgccgcggcc gaacagaaga agcacaaccg   4860
ccagaacgat cagccagtgc cagatggaaa agctacccat attattcctc tcagtgccgc   4920
ccaaggcgcg gcatatgcct gctatctccg atacgattta agcgctttca acaaatcttt   4980
caaacagaag tgtgatgatg aacggcttca aaccggatta attcgtcgca ggcagaaatt   5040
ttgttctatt ctcccctggg tgcaagcaaa cccagtccct ccagatcaat atcctccagc   5100
gggtcctccc cttcggtcag ctcgtccggg tcgatattgg ggatcggtac ggcaaaactg   5160
gaaggaatgc gcgccgagag aagccctgcg ccgcgcaatt cctcaagacc gggcagatcg   5220
```

```
cggatttccg gcaggccaaa atggtcgagg aaagcgtcgg tggtgccata tgttaccggg    5280
cgccctggcg tgcgcctgcg cccgcgcagc ttgatccagc cggtttccat caagacatca    5340
agcgtcccct tggatgtttc cacgccgcga atatcctcaa gttcggcgcg tgtcaccggc    5400
tggtgatagg caatgatggc aagcacctcc atggtcgcgc gcgaaagctt gcgctgctga    5460
acagtctcgc ggttcatgat gaaggcgaga tctggcgcgg tgcgaaacgc ccagccactg    5520
cccaccttca caaatgcacg ccccctgccc tcgtaaacct tctggagatg gttcaaaacc    5580
ggagcaatat ccacattggc gggaagccgc tcggcaagtg cgcgctcgca acaggctgc     5640 gaagacgcaa aaacaatcgc ctccacaatg cgggcaagct cggcaagcgt caccggcgag    5700
gcaggccccg cctgctcttc ttccccaacg ccttccatat ccatcaaatc gcggcgctct    5760
gcttcaggca ttttcgtcct catcgaattc atcgagttcg cggtcgcgc gcatatagat     5820 cggctcgaac ggagcgttct ggcgtacttc aagcttgcct tcgcgcacca gctcgaggca    5880
tgcggcgaaa gaactggcaa gcgccgacgc cctctcctgc ggagaaagtg cataatcgat    5940
caaaaaacgg tccagcgaaa cccagtcgcc caccgcgccc atcaggcgca caagcgccgt    6000
gcgtgcctcc ttgagggacc agacgctgcg ttttctatc tgtacctggg aaaccgcctg     6060
gcgctggcgc tgcgacgcat aagcgctaag cagatcgtaa agcgttgcgg aaaaacggct    6120
ggcgcggtcc accaccacca tttccggcat gccgcgcggg aaaacatcgc ggccgagccg    6180
atgacgattg acgagtgccg ccgccgcatc gcgcatggct tcaagccgtt tcaaccggaa    6240
ttgcagggag gcaacgagtt cctcgcccgt ggcgccatcg tcgccctgct gcttcgggat    6300
cagcagcttg gatttcagat aggcaagcca tgccgccata acgagataat cggcggcaag    6360
ctccagacgc agcgcgcgcg cctgctccac gaaaccgaga tattgttcgg caagcgccag    6420
cacggaaatg cgcgcaagat cgacgcgctg gttacgcgca agatgcagaa gaaggtcgag    6480
cggaccttca aagccctgca catcgatcag cagtgacggc tcgcctgcgc ctcgcccggc    6540
ctcattttgc cacagggtat ccatcggcac gcgtgtgccg tcgtttccac ctgtatgtgc    6600
atccgatgct gccaagcctg tcgtcctgct gttgcccctg ccggcacaga ttctgccagc    6660
aggaacaagt ttatcaagtt ttgccgatta cgctatcggt tcaaacatgg cattgaattc    6720
ggcgcgcacc tcgtcctcgt cggaaagatc ggggtcgccc gcatagactt ccgccagttc    6780
ggcccggcgc tttgctttgc catccagaac cggcacacgg gcggcaacct ttaccagttc    6840
ctccataacg cctgagcaat agagcacgat atcgcagccc gccgtaacga tgccgtcggt    6900
tatatcgcca agatcgccgg acaatgcctt catggaaatg tcgtcactga tgacaaggcc    6960
gtcgaacccg atcacatcgc gaatgatcgt attaataacc gtcggcgaaa gcgtggacgg    7020
tctttccggg tcgatgcaat cgaacaccac atgggcggtc atggccatcg gcagatcatt    7080
gagcgccttg aacggcacga atcatgcgc aaccagttcg ttgagcgcaa cgctgacccg      7140
cgccagttcc ttatgcgtat cggaaaaggc gcggccatgg cccggcatat gcttcacgac    7200
gggaagaacg ccgccagcca aagaccttc ggcggcagcg cgtcccattt ccgcaaccgc     7260 atggggttt ttggaatagg cccgcattcc gatcacatca tgcgcgccct ccaccggcac     7320
atccagaacc ggcaggcaat ccgcattgac gccgaccttc aacagatcga aagcatggag    7380
ccgggcatgg agccaggcgg cacgcaaccc cttttccttg tcgcgtgcat agatcgcgcc    7440
aatttcggac gcggacggat agttcggtac cagcggcggg cgaaggcgct gcacgcgccc    7500
gccctcctga tcgatgaaaa ccggcgtctg gtccagcccc gtcaggtcac gcagatgggc    7560
ggtgagctcg ctcacctgtt cgaggctttc cacattgcga gcaaaagaa tgaagcccca    7620
```

```
cggggtttca tcccggaaga aggcaatctc gtccggggtg agcttcgtgc cggatatacc   7680
ggcaatccat gccttgcact ctttcatgcg gcttttcctc gaattgtctt gctgaatcaa   7740
actcgcctcc gccgggttta gccgaaaaaa cggccgcttg gtaggctgta ggctgtggtg   7800
acgaattaac ttatggttcg gtatgaacga aaatgctcaa tagcccggca gatgcgaaaa   7860
gggcggctga cgccgccctc aaatggctgg aaccttgctg gttgttttta ctgcgtcacg   7920
aaacagcttc cgccagccga cttgagacgg ctgcaaagcg ccaatgcatc ttccttcgag   7980
ccagcctgta cgcgaacacg gtaataggtg cccttgccct gaatgtcggc gcgcttgata   8040
tcgacgctat gaccgccaat cacactggca tatttctggg ctatgttggc ataggacttc   8100
tgcgccagct cagcagaagg ctgcgaggca atctggatga aataaccacc cgccccggct   8160
gccgatgcga cctgcggtgc agccgatgcc tgcgcgcgct gcggcacgtt accgacgata   8220
ttgacgggct gttcagcggg gcgcgacggc acgatcggag cgcgggtcgg aaggcgtggg   8280
gtctccggcg tcgcggattg ctgtgcctgt ggcgctggcg gttcatttcc tgccgcgagt   8340
gcgccgattt catcccgtgc tgccggtgcg gcaggcggcg ccatattgtc ggctaccgac   8400
ggctgtgctg catgtccgaa cgaaggctga atgatcgtgc catccgggcg aacgatcatc   8460
gtttcgacct cacgcggctg gatcagcggt tcatgcgtgc cggaatgagc ctgttgcgca   8520
tcgttctgcg gtacattgcc acccggttct tctgtggcat tatattcgct gtcatcggta   8580
ccggaaatat cgaccggttc ttcaccggat gtaatcaggg cttttctgttc cgggttgttc   8640 ggaagcgttc cggccacacg gtcatagacc gccttatcct ggttcggaac cgtggttccg   8700
cccggatttt ccggctgcat cttgatgggc tggttatcgg cgcgaatcac aaccggctca   8760
ccggagcctc cgccgccgag gaaatgatag ccgattccgc cgagcagaac cgccacaccg   8820
gcaacacttg ccaaaatcaa gccacggcga ccacgaaccg ggcgattgcg gtaagcttcc   8880
gccgcgccgc ccagatcgtc ttccgtcggc attgcggcgc gctcgccata atcgccgcct   8940
tccatggtct gcgcacccetg cgcggcccag tgattgtaga aatcatcctg gctggcagtc   9000
gttgcagcgg caggtgcagc ttcagacccg gcgcgtcggt aggaagcagc agccgctgcc   9060
gccgcagcac ccaagccggc cgcggccatg ccgctattcg gcatataggt cgatgcgctt   9120
tcacggaaga tgtcctcaaa agccctgtcg gcttcgctct ggccttccgt gatctgcaca   9180
ttctcatcaa caccaatcgt gctgaaaact tccgcgaact ccgcttccag ctcactgaga   9240
ttggtgcccg cttcctcttc gccgtaattc acttccggca gatcgagcga atgcgtctgt   9300
tcgaccttgt tttccgtgac cgtgagggtc tcaacctccg gtgcaggctc cggtgcgggc   9360
atacgcgccg gagcctgcat gtcggtataa gcggcaaagg agacagcagg gcgataatcc   9420
tcgccggaat ggattgcgtg cgcataggct ggcgcgggag aagcttcttg ctcctcctca   9480
tggagatcaa gttcaacatc ggtgaagaaa tcttcatcgt tgaaaaaatc ttcatccgca   9540
gtatcggcga cgtctgcgtc gaatgtgtct ccagacggct cgaaaccgaa atcatcttcg   9600
gtcaggctga tttcgtcgag ccccgacagg tcatcatccg tcgattcggc ggcggcagcc   9660
gtttccggct ctgcttcaaa ggtaaaatcg tcctcaagcg aaaactcatc ctcgattggc   9720
cggaacggat cctgggcaac aaaatcctgc acaataggcg cctgggcgt tttcagttgc   9780 ggccccgagg agagcacacc gggggcggct cacccggcg caaaattgct gcgcggataa   9840
tagggatagg ccggcgcctc gccagtgcgt gacgcatagc cctgcccggc atgggacgga   9900
gcatccagat gcggttcgct gaccggcgct tccggttcgc cctgatgcgg ttgttccggc   9960
gcgtaggaaa caggctcgac gtgatccgaa tagctgttcc gggatgccac aggctgcggc   10020
```

```
tcatcgccaa acagaaggtt ttccagctcg tcttcaagcg aaagcggttg ctgtgcaggc    10080
tcagccgcga aatgcgtagc gggagcatct acaggctgct gcgcattcca attattctgt    10140
gctggccagt cattctgttc cagcctgtca ttctgtgcag gccactcatc ctgtgcctgc    10200
caattgtcct gcacgccggt atcttcacgc caagcttgct cacccggctc aatggcaggc    10260
tgatagacgg tcggatcata ttcgcccgca tctgcctcta tcggctgctg gcgatcacca    10320
taagccgcag gtgatgccat atgggcgtgt tcgctcgaat cacgagcctg cgaataatcg    10380
ttatagtcga attgcggaac gggctcggag cgatccacgt cctcgaactc gaaaatttcc    10440
ggtgacggtg ctgcttctgc cgagccaagg tcgagatcga attcttcttc cagcgcggca    10500
gcgaacgcat cctcctccaa cggagactgc tcgccatagg cccgctcccc gtgcacgcca    10560
aaggttgcgg tcgaaacggt ttcgctatga gctgtaggct gcgtataatc gtcgaaatgc    10620
cccataagct cgcgctcaag atcgagaacg ggatcaaaag aggggtcatc ctgcgccgaa    10680
tcaaagcgcg gctctgctcg gccctgatcc tcgaattgac tgtcatggcg gcgctcattc    10740
cgagcgacgt tatcatcagc aggcgtgtcg aagtccataa tccgcgaaag ttccatcagc    10800
ggatcatctt cgtgcaccgg acgctcgccg taattacggg gatttgcact gctgtccgtc    10860
atggcgtgtt cctaactcaa accctggacg ccgcaagacg tctccataca ttgcatatta    10920
gcgaggcaat gtgggcaaaa gttgacggaa gtttcctgca caggaaggaa gatcc         10975

<210> SEQ ID NO 27
<211> LENGTH: 4500
<212> TYPE: DNA
<213> ORGANISM: Brucella melitensis

<400> SEQUENCE: 27
tattagcgag gcaatgtggg caaaagttga cggaagtttc ctgcacagga aggaagatcc      60
atgactttca atcatactga tcttccttca cattagtctt actgtcactc atccaaaggc     120
gtctttcgac tttcagtact tcggacgacc gtgtaatcct agcgcatctc cgtaggagca     180
tccgcgccga taatcgtcaa tcctgacgtc agcacatcgg aaacaacctg caccagccct     240
agcctggcca gcgacaagtc tggatcgtta accttaataa aacgtaagtc cggatttttcc    300 gcgcctctgt tccattgcga atggaacgaa ctggcgaggt cgtagaggta gaaagccagg     360
cgatgcggct cctgatgaat ggctgccgat tcgatcaggc gcgggtattc cgcaagcttg     420
cgaacgagcg caatttcgct ctcgtcggtc agcttttcaa aatgcgaccc catggccacg     480
cggtcaagat cgacaagccc aagctggtcc gcagcctgac ggaaaaccga atggcagcgc     540
gcggaagcat attgcacata gaaaaccgga ttgtccttgg actgctccgt caccttggcg     600
aagtcgaagt ccaatggcgc atcgttcttc cggtaaagca tcatgaagcg gaccggatcg     660
cgaccgacct cgtccaccac atcgcgcagc gtaatgaact cgcctgcccg cttggacatg     720
cgcaccggct cgccattgcg gaacagcttc acgagctggc acaggagcac ggtcaatttg     780
gccttgccat cggaaacggc acgcgcaacg gcttccagac gcttgacata accgccatga     840
tccgcgccga gcacatagat catctcattg aagccgtggt cgtacttgtc cttgaaatag     900
gccacgtcac ccgcaaaata ggtgaacgag ccatcggact tcatcagcgg acggtcaata     960
tcatcgccca cttccgtaga acggaacagc gtctgctcac ggtcttccca atcttccggc    1020
aactgcccct tcggaggcgg cagcttgccc ttataaacat ggcccttgag cgtcagatca    1080
ttgatcgcgt tacggatcgc gcgcgcatgg tcgacatgta gcttgcgctc ggaatagaag    1140
acatcatgat gcacgttcag cgcgtcgaga tcagcgcgga tcattgccat catggcgtcg    1200
```

-continued

```
atcgtgcggt ccttcacgat ggccagtgct tcggcttcag gcatttccag aagttttgtg   1260
ccaaactcac cggcaagctc ctgcccgacc cgcacgagat aatcaccggg gtaaagcccc   1320
gccggaatct cgccgatgct ttcgcccagt gcctcacgat agcgcagcat cacagaacgc   1380
gcgagaacat cgatctgcgc gcccgcatcg ttgatgtaat attccttgac gacgtcatag   1440
cccgcgaatt tcagcaggtt cgccagcaca tcacccacaa ccgcgccccg gcaatggccg   1500
acatgcatcg ggcccgtagg gttggccgat acatattcga cattgacctt cttgcccgcg   1560
ccaagcctgg agcggccaaa atccgttccc tcgttcagca tcaccaaaag ctcgcgctgc   1620
caatagctgg ccttgaggcg cagattgatg aagcccggac cggcgacatc gacggattcg   1680
acatcctcat cggccttcag cgcctcggca atgcgggcag caagctcgcg cgggttctgg   1740
ccgaccgcct tggaaagcac cattgcggca ttggtcgcga tatcgccatg cgaagcatcg   1800
cgcgggggct cgacacctat gcgtgaaagg tcaagttcac caccatcttt tggtttcaga   1860
tcaatatctt gcaacgtttt tttaatacgt gcatcgaaat ctgcaaagat attcatggtc   1920
tgtcctgtca ggctagcgcg gttcctgttt aacagaatc gccggaacca ctctaactat   1980
tgttttgtcg cattttccaa cgcaaaaccg tttcacactt ttggctcgaa aatactctaa   2040
cgcctggatt tttttccagt tttcccggcg cgggttcatc caaaaaacgc ggatattcga   2100
tgcatttgcg tatcgaagcc gcttcgtccg gccccgatta agctaaatcg ggggttcggt   2160
caaacaatcg tcggtgttcg cgcacggcat aattatcagt catcccggcc agataatcgg   2220
ctacgcggcg tgcgagtgct gccttatcca gtgcctcaca gcccaaacgc cattcatcag   2280
gcatcaatga gggatcggtg aaacaggcat cgaagagatc ctgcacgatc ctgtcggctg   2340
cgtgcctgcg caccaccacg ctttcgtgaa aatagagatt cttgaacaaa aagcgcttca   2400
gcacctttc ctcggcccgc atggcgtcgg aaaagccaac cagcgcgcgc ggctggttgt   2460
gcacgtcttc catcgttccg ggcctggcgg atgcaaggcg cgctgcgcc tcctcgatca   2520
cgtcttccac catgatcgtg atctggcggc gcaccagttc gtgtccagtg cggacggggt   2580
cgagattggg ataacgtgtc cgcacaatat caagcagccg tttggcgagc ggtacttcgt   2640
ccagcgattc gagggtcaag agccctgccc gcaagccatc atcaatgtca tgcgcattgt   2700
aggcaatgtc gtcggcaatg gccgcgcatt gcgcctcaag gctcgcaaag cgtgaaagct   2760
ccagatcata gcgcgcgtta aaatccagaa tgggttgcgg aaccgggata tcgggatggg   2820
ctgcatatgg ccccagcaac gggccattat gcttcaccag accttccagc gtttcccacg   2880
aaaggttgag gccatcgaaa tcagcgtagc gatgctcaag cttcgtgacg atcctgagcg   2940
actgggcatt atggtcgaaa ccgccgaaat tcttcatgcg ctcgttgagt gcgtcctcgc   3000
cggtatggcc gaagggcgtg tggccgaaat catgaacgag agcgacagct tcagcgaggt   3060
cttcatccag gcgcagcgcg cgcgccagcg cccgcgcaat ctgcgccacc tcgatggtgt   3120
gcgtcagcct cgtgcggtaa tgatcgccct catgcgcgat gaaaacctgc gtcttgtgct   3180
ttaaacgccg gaaagccgtg gagtggataa tacggtcacg gtcccgctgg aacggcgtgc   3240
gggtcgggct ttccggttcc ggcaccagcc ggccacggct gaaagcagga ttgctggcat   3300
aaggcgcacg ttcgcgataa ccgaagccta ttccttccag cgacattgcg atgttttcct   3360
cactgtaata tgattacgtc aaattggtgc gtcattgact tccgcaacct gcgttcatag   3420
ctatcagcta aacatgaagg caagtacgcg gctatcggaa aatctcaaga acgcataacc   3480
cgatccccgt ccctgcaaac ggaacaaggc aaatgacagg cattaccgtt tcagattccg   3540
ctgccaggcg gatcgccaaa attctcgatt cggagccggg aaagaccgcg cttcgcgttt   3600
```

```
ctgtcgaagg tggcggctgc tccggctttt cctataaata tgacctcgtc gacgcacaga    3660
ccgaggatga catcgtcatc gaaaaactcg gcgccagagt gctgattgat tccatctccg    3720
tgccttatat ggacggctct gaaattgatt tcgtcgatga tctgatgggg caatcattcc    3780
agatccgcaa ccccaatgcg accgcttcct gcggctgcgg caccagcttc gcgatctgag    3840
cggcgcaaca aaacccgtga tgcaaaaccg gcggccagat ggccgccgtt tttttaacca    3900
tggcaacaag cggacagttt cagactttca ctgaagcaac ggtcgcttcg atgtggtcca    3960
ccagcgcatc ttgcaggcca agccgcccgg caagcatatc agatagccg cgttcggcgc     4020 ggttatctgg atcgatagcc agccgcgatg ccgtataaag ttcaactttc tgctcttccg    4080
tctgcgctgc ggcaaccagc acatcgagat cgacgggttc ggccagttcc cttgcaagga    4140
aggcctcagc ctcgtcgtcc agaccggaaa tcttcaccct ttccatgatg cgggcacgtt    4200
cggcatcatc aatataacca tcagccctgg cggcggcgat catggcctga ccagcgtca    4260 gcgcgaaact attgctcatc gcgggagaat gcggatggaa gggtgaatcg gccggtggcg    4320
ccggaagaag ctccggctct tttgccaccg gctgttccgc ctcctgcggg gcctgaccgg    4380
acttataatt cttgtaggca agatagccca atccggctat ggcggcgatg ccgccgacag    4440
ttgctacatt gccagcaagt ttgcggcccg ttttcgtgcc aaaaatggct gcggctatgg    4500
```

<210> SEQ ID NO 28
<211> LENGTH: 1008
<212> TYPE: DNA
<213> ORGANISM: Brucella melitensis
<220> FEATURE:
<221> NAME/KEY: CDS
<222> LOCATION: (1)..(1005)

<400> SEQUENCE: 28

```
atg aca att ctt gta aca ggt

| | | | | | | | | | | | | | | | | |
|---|---|---|---|---|---|---|---|---|---|---|---|---|---|---|---|---|
| gac | ctt | tat | aac | agt | gac | aat | agc | tgg | gcg | att | gcg | att | ctg | cgc | tat | 528 |
| Asp | Leu | Tyr | Asn | Ser | Asp | Asn | Ser | Trp | Ala | Ile | Ala | Ile | Leu | Arg | Tyr | |
| | | | 165 | | | | 170 | | | | 175 | | | | | |
| ttc | aat | cct | gtc | ggc | gct | cat | gaa | agc | ggg | ctt | atc | ggt | gaa | gac | ccg | 576 |
| Phe | Asn | Pro | Val | Gly | Ala | His | Glu | Ser | Gly | Leu | Ile | Gly | Glu | Asp | Pro | |
| | | 180 | | | | | 185 | | | | | 190 | | | | |
| aag | ggt | att | ccc | aac | aat | ctg | atg | ccc | att | att | gct | cag | gtc | gca | act | 624 |
| Lys | Gly | Ile | Pro | Asn | Asn | Leu | Met | Pro | Ile | Ile | Ala | Gln | Val | Ala | Thr | |
| | | 195 | | | | | 200 | | | | 205 | | | | | |
| gga | cga | cgc | gaa | aag | ctg | aac | atc | tgg | ggc | aac | gac | tat | ccg | aca | ccg | 672 |
| Gly | Arg | Arg | Glu | Lys | Leu | Asn | Ile | Trp | Gly | Asn | Asp | Tyr | Pro | Thr | Pro | |
| | 210 | | | | | 215 | | | | | 220 | | | | | |
| gat | ggc | acc | ggc | gta | cgc | gac | tat | atc | cat | gtc | aac | gat | ctg | gct | gcc | 720 |
| Asp | Gly | Thr | Gly | Val | Arg | Asp | Tyr | Ile | His | Val | Asn | Asp | Leu | Ala | Ala | |
| 225 | | | | | 230 | | | | | 235 | | | | | 240 | |
| ggg | cac | ctc | aag | gcc | ctg | aaa | aag | ctg | gat | aag | ccc | aag | tgc | ttc | gcc | 768 |
| Gly | His | Leu | Lys | Ala | Leu | Lys | Lys | Leu | Asp | Lys | Pro | Lys | Cys | Phe | Ala | |
| | | | | 245 | | | | | 250 | | | | | 255 | | |
| gtc | aat | ctt | gga | acg | ggg | cag | ggc | tat | agt | gtt | ctt | gat | gtg | atc | aag | 816 |
| Val | Asn | Leu | Gly | Thr | Gly | Gln | Gly | Tyr | Ser | Val | Leu | Asp | Val | Ile | Lys | |
| | | | | 260 | | | | | 265 | | | | | 270 | | |
| gcg | ttt | gaa | cat | gtc | tcc | aat | cgc | gag | atc | aaa | tat | gag | att | gcg | ccg | 864 |
| Ala | Phe | Glu | His | Val | Ser | Asn | Arg | Glu | Ile | Lys | Tyr | Glu | Ile | Ala | Pro | |
| | | | 275 | | | | | 280 | | | | | 285 | | | |
| cgc | cgt | ccc | ggc | gat | gtt | gcc | gaa | tgc | tat | gcc | gat | ccc | ggc | ttt | gca | 912 |
| Arg | Arg | Pro | Gly | Asp | Val | Ala | Glu | Cys | Tyr | Ala | Asp | Pro | Gly | Phe | Ala | |
| | 290 | | | | | 295 | | | | | 300 | | | | | |
| aag | aaa | ttt | ctg | ggc | tgg | tcg | gct | gag | aaa | aac | ctg | cgt | gaa | atg | tgt | 960 |
| Lys | Lys | Phe | Leu | Gly | Trp | Ser | Ala | Glu | Lys | Asn | Leu | Arg | Glu | Met | Cys | |
| 305 | | | | | 310 | | | | | 315 | | | | | 320 | |
| cag | gac | atg | tgg | aac | tgg | caa | tcg | aaa | aat | ccg | aac | ggc | tac | gaa | taa | 1008 |
| Gln | Asp | Met | Trp | Asn | Trp | Gln | Ser | Lys | Asn | Pro | Asn | Gly | Tyr | Glu | | |
| | | | | 325 | | | | | 330 | | | | | 335 | | |

<210> SEQ ID NO 29
<211> LENGTH: 335
<212> TYPE: PRT
<213> ORGANISM: Brucella melitensis

<400> SEQUENCE: 29

```
Met Thr Ile Leu Val Thr Gly Gly Ala Gly Tyr Ile Gly Ser His Thr
1               5                   10                  15

Cys Val Gln Leu Ile Glu Ala Gly His Glu Val Val Val Val Asp Asn
            20                  25                  30

Phe Asp Asn Ser His Pro Glu Ala Leu His Arg Ile Glu Lys Ile Thr
        35                  40                  45

Gly Arg Ala Pro Arg Arg Glu Pro Gly Asp Ile Arg Asp Arg Ala Leu
    50                  55                  60

Met Glu Gln Met Ile Lys Arg His Lys Cys Thr Ala Val Ile His Phe
65                  70                  75                  80

Ala Gly Leu Lys Ala Val Gly Glu Ser Ser Glu Lys Pro Leu Leu Tyr
                85                  90                  95

Tyr Asp Cys Asn Val Leu Gly Thr Leu Arg Leu Leu Gln Ala Met Glu
            100                 105                 110

Ala Thr Gly Val Lys Lys Leu Val Phe Ser Ser Ser Ala Thr Val Tyr
        115                 120                 125

Gly Asp Pro Asp Lys Leu Pro Ile Thr Glu Asp Gln Pro Leu Ser Ala
    130                 135                 140
```

-continued

```
Thr Asn Pro Tyr Gly Arg Thr Lys Leu Val Ile Glu Asp Met Leu Arg
145                 150                 155                 160

Asp Leu Tyr Asn Ser Asp Asn Ser Trp Ala Ile Ala Ile Leu Arg Tyr
                165                 170                 175

Phe Asn Pro Val Gly Ala His Glu Ser Gly Leu Ile Gly Glu Asp Pro
            180                 185                 190

Lys Gly Ile Pro Asn Asn Leu Met Pro Ile Ile Ala Gln Val Ala Thr
        195                 200                 205

Gly Arg Arg Glu Lys Leu Asn Ile Trp Gly Asn Asp Tyr Pro Thr Pro
        210                 215                 220

Asp Gly Thr Gly Val Arg Asp Tyr Ile His Val Asn Asp Leu Ala Ala
225                 230                 235                 240

Gly His Leu Lys Ala Leu Lys Lys Leu Asp Lys Pro Lys Cys Phe Ala
                245                 250                 255

Val Asn Leu Gly Thr Gly Gln Gly Tyr Ser Val Leu Asp Val Ile Lys
                260                 265                 270

Ala Phe Glu His Val Ser Asn Arg Glu Ile Lys Tyr Glu Ile Ala Pro
            275                 280                 285

Arg Arg Pro Gly Asp Val Ala Glu Cys Tyr Ala Asp Pro Gly Phe Ala
        290                 295                 300

Lys Lys Phe Leu Gly Trp Ser Ala Glu Lys Asn Leu Arg Glu Met Cys
305                 310                 315                 320

Gln Asp Met Trp Asn Trp Gln Ser Lys Asn Pro Asn Gly Tyr Glu
                325                 330                 335
```

BRUCELLA MELITENSIS MUTANTS AND METHODS

CROSS-REFERENCE TO RELATED APPLICATIONS

This application is a Continuation of U.S. application Ser. No. 11/633,371, filed Dec. 1, 2006, which claims benefit of U.S. Provisional Application No. 60/741,282, filed Dec. 1, 2005; both applications are incorporated by reference herein to the extent there is no inconsistency with the present disclosure.

STATEMENT REGARDING FEDERALLY SPONSORED RESEARCH OR DEVELOPMENT

This invention was made with government support under Grant Nos. R01AI048490 and AI057153 awarded by the National Institutes of Health (NIH/NIAID. The government has certain rights in the invention.

REFERENCE TO SEQUENCE LISTING, A TABLE, OR A COMPUTER PROGRAM LISTING COMPACT DISK APPENDIX

The Sequence Listing filed herewith is incorporated by reference.

BACKGROUND OF THE INVENTION

The field of this invention is microbial genetics, especially as related to immunogenic compositions comprising attenuated bacterial pathogens or components thereof.

The *Brucella* species are important zoonotic pathogens affecting a wide variety of mammals. In agriculturally important domestic animals, these bacteria cause abortion and infertility, and they are of serious economic concern worldwide (5). In humans, *Brucella* species constitute potential bio-warfare agents. *Brucella* species that infect humans cause in undulating fever, which if untreated, can manifest as orchitis, osteoarthritis, spondylitis, endocarditis, and neurological disorders (11, 46). Currently there is no vaccine to protect against human brucellosis, especially that caused by *B. melitensis*. Treatment of brucellosis requires a prolonged combination of antibiotic therapy and is still problematic because of the potential for relapse.

Identifying *Brucella* virulence factors has been of great interest in understanding *Brucella* pathogenesis and immune evasion. After entry into macrophages virulent *Brucella* cells reside in an acidified vacuole, the *Brucella* containing vacuole (BCV). The BCV transiently interacts with early endosomes, followed by VirB-dependent sustained interaction with the endoplasmic reticulum (7). Thus, the BCV matures into a replicative niche in a VirB-dependent manner (7, 8). VirB proteins forming the type IV secretion system (T4SS) constitute important factors for *Brucella* virulence and intracellular replication (9, 14, 34). Lipopolysaccharide (LPS) is also an important virulence factor (27). *Brucella* LPS has minimal endotoxic effect, blocks complement activation, and protects against bactericidal cationic peptides (28). The O-chain is also important for the conventional entry of *Brucella* into macrophages through lipid rafts, a route which avoids fusion of the BCV with lysosomes (33, 37). Cyclic β-1, 2 glucan has been shown as an important virulence factor required for intracellular survival of *Brucella* (3). Although T4SS, cyclic β-1, 2 glucan, and LPS are clearly virulence factors of *Brucella*, the attenuated mutants lacking these virulence factors are either considered not safe or insufficient information is available to use them as vaccines for humans. This has necessitated identification of additional vaccine targets.

Several genetic loci that are required for *Brucella* replication in vitro have been identified (14, 24). In vitro conditions may not adequately reflect in vivo infection, and therefore, findings may have little or no in vivo relevance (45). In vivo screening methods have been used to identify *Brucella* genes required for survival and persistence (18, 26), however, these previous studies have relied on the conventional approach of determining tissue-specific cell counts (CFU) from multiple animals at different times, a process that is labor intensive and requires large numbers of animals. Because infection is a dynamic process and varies within individual mice, monitoring disease progression temporally within the same mouse provides a more comprehensive picture of pathogenic events. Further, such real-time analysis may reveal virulence determinants responsible for tissue specific replication of bacteria that would not be revealed using conventional CFU enumeration from liver and spleen.

Bioluminescent imaging of mice allows direct visualization of the infection process and is highly useful for bacterial pathogenesis studies (10), because the intensity of bioluminescence strongly correlates with the number of bacteria in the infected organs (16, 40). Bioluminescent imaging is useful in analyzing sub-acute and chronic infections that are often difficult to assess using conventional approaches because of uncertain bacterial locations (16, 40).

There is a long felt need in the art for safe and effective vaccines that protect humans and animals from infection by the pathogenic *Brucella* species, especially *B. melitensis*.

BRIEF SUMMARY OF THE INVENTION

The present invention provides attenuated mutants of *Brucella*, including *Brucella abortus* and *Brucella melitensis*, which are useful in generating protective immunity to infection by virulent *Brucella*, including *Brucella melitensis* and *Brucella abortus*. In particular, mutants in which the galE gene (ORF BMEI0921 or the corresponding gene in other species of *Brucella*) is inactivated are useful in live vaccine formulations and mutants in which one or more peptidoglycan biosynthetic genes are functionally inactivated, i.e., the genes encoding the lytic murein transglycosylase and/or β-hexosaminidaseare inactivated, for example polar mutations in the operon in which these genes are expressed, with the disruption eliminating all, four or three genes within the relevant operon (ORFs BMEI1087-1090 in *B. melitensis* or corresponding genes/operon in other species of *Brucella*) are not functionally expressed. See Tables 5 and 6 and SEQ ID NOs:26 and 27. The mutations resulting in the attenuated phenotype due to inactivation of galE can be insertion, substitution or deletion mutations. With respect to the peptidoglycan related genes, it is not entirely sufficient to eliminate functional expression of only the dGTP phosphohydrolase gene to produce a mutant which is attenuated enough to be a desirable vaccine strain. Where the galE-like mutant of *B. melitensis* is used, it is recommended that the genetic background into which the mutation is introduced is a 16M genetic background.

Also within the scope of the present invention, are attenuated mutants of other species of *Brucella*, including *Brucella abortus, B. suis, B. ovis*, etc, where the functionality of the corresponding gene(s) as described above are destroyed. The coding sequence identified by ORFs BMEI1087-1090 are presented in Tables 5 and 6; see also the corresponding regions of SEQ ID NO:26-27. In strains and species other than *B. melitensis* 16M, from which the sequence information of Tables 5 and 6 is derived, the corresponding genes will have at least 85% or higher nucleotide sequence identity, thus enabling the generation of equivalent mutants in these coding sequences. Such mutants, when administered as live vaccines, provide an immune response to the cognate species of *Brucella*.

Within the present invention, there is at least one attenuated strain of *Brucella* in which there is a mutation which functionally inactivates or prevents expression of at least one of the galE and having at least 85% nucleotide sequence identity to SEQ ID NO:28, the gene encoding lytic murein transglycosylase and having at least 85% nucleotide sequence identity to nucleotides 7908-10817 of SEQ ID NO:26, β-hexosaminidase and having at least 85% nucleotide sequence identity with nucleotides 6688-7740 of SEQ ID NO:26, or a gene encoding deoxyguanosinetriphosphate triphosphohydrolase and having at least 85% nucleotide sequence identity with nucleotides 2138-3346 of SEQ ID NO:27. Also encompassed are immunogenic compositions for administration to a human or animal comprising an attenuated strain of the present invention. The bacterial cells in the composition can be killed or live, advantageously alive.

Further embodied within the present invention are immunogenic compositions comprising live cells of attenuated *Brucella* cells, and a pharmaceutically acceptable carrier. These attenuated *Brucella* cells can be deficient in the functional expression of at least one gene selected from the group consisting of galE, lytic murein transglycosylase and β-hexosaminidase. Such compositions include vaccine compositions for use in humans, sheep, goats, cattle, bison and other susceptible animals. It is understood that the immunization with one particular species of *Brucella* results an immune response primarily to same species as administered. Thus, for protection against *B. melitensis*, it is desired to administer an immunogenic composition comprising at least one live attenuated *B. melitensis* mutant, as set forth herein. These compositions can further comprise an agent which stimulates the immune response, for example, an interleukin such as interleukin 12.

The present invention further provides methods for generating an immune response, especially a protective immune response in humans, sheep, goats, and other animals. Desirably, the immune response generated is a T cell response. A single injection with live cells of least one attenuated *Brucella* mutant strain (desirably from $10^3$ to $10^8$ viable cells of each strain) as set forth above can trigger a protective immune response in the human or animal to which it has been administered, due to the persistence of the bacterial within the body of that animal. The immunogenic composition can be administered by any route of administration, such as subcutaneous, intramuscular, intraperitoneal, intravenous, mucosal, intradermal and so on. Because of the ability of the attenuated mutants of the present invention to persist in the body, it is not necessary for there to be repeated administrations of the immunogenic composition, although booster immunizations may be given.

Also within the scope of the present invention are attenuated mutants of *Brucella* strains having the same or equivalent defects to those of GR024 and GR026, as described herein, in which the hly gene (listeriolysin O) of *Listeria monocytogenes* is expressed. This results in *brucella*-infected cells which are "leaky", thus resulting in a more effective immune response.

The present invention further provides methods for identifying *B. melitensis* peptides that correspond to MHC class I-restricted T cell epitopes, especially those associated with MHC class I (H-2 $K^d$).

Applicants have deposited samples of *Brucella melitensis* strains GR026 and *Brucella melitensis* strain GR01090Δ with the American Type Culture Collection (ATCC), 10801 University Boulevard, Manassas, Va. 20110-2700 on May 3, 2011, in accordance with the provisions of the Budapest Treaty, and these strains have been assigned the following identification numbers: PTA-11877, and PTA-11878, respectively. Each of these strain deposits will be maintained without restriction in the ATCC depository for a period of 30 years, or 5 years after the last request, or for the effective life of the patent, whichever is longer, and will be replaced if the deposit becomes non-viable during that period. Upon grant of a patent, all restrictions imposed by the depositor on the availability to the public of the deposited biological material will be irrevocably removed.

Additionally, the present invention provides a number of peptides that are associated with intracellular survival strategies of *Brucella*. These include several derived from an extracellular serine protease (BMEEII0148), characterized by a carboxy terminal region (amino acids 2349-2554) with high sequence homology to the β-domains of autotransporters of the Type V Secretory Systems of bacterial pathogens.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

FIG. 2A: Stationary phase grown cultures (30 μl) were inoculated into 30 ml of *brucella* broth and grown at 37° C. with shaking and $OD_{600}$ was determined. FIG. 2B: RAW264.7 macrophages were inoculated with a standardized bacterial suspension of different strains and growth monitored at specified times. The CFU counts were log transformed and values are average±standard error for duplicate samples.

FIGS. 3B and 3C show virulence in IRF-1$^{-/-}$ mice. RAW264.7 macrophages were inoculated with a standardized bacterial suspension of GR019 and GR019 complemented strains, and the growth was monitored at specified times. The CFU counts were log transformed and values are average±standard error for duplicate samples. IRF-1$^{-/-}$ mice were inoculated i.p. with $1\times10^7$ CFU of GR019 and GR019 complemented strains, and mouse survival (FIG. 34) as well as CFU from livers, spleens and testes (FIG. 4C) were determined. The CFU counts from livers, spleen and testes were log transformed and the data are an average of 4 mice. Error bars represent the range of CFU.

Spleens were scored on loss of white and red pulp architecture at 4× magnification; (−) normal spleen or no noticeable changes, (+) enlarged follicles, increased cellularity, and white pulp, (++) hyperplasia, with a significant increase in follicle size, and white pulp. (+++); increased red pulp and loss of white pulp architecture.

Figure 7:
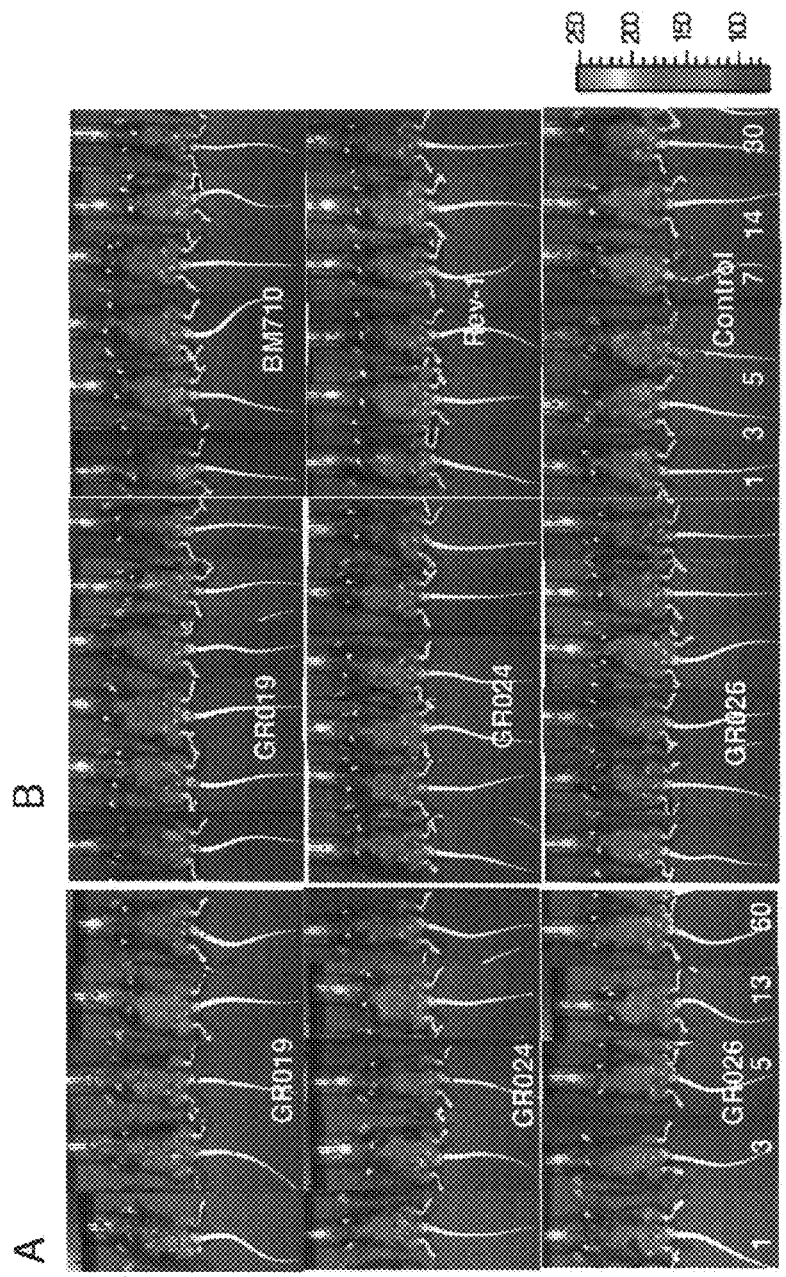

FIG. 7A illustrates real-time analysis of attenuated bioluminescent B. melitensis strains in C57BL/6 mice. C57BL/6 mice were infected with $5\times10^7$ cfu of B. melitensis strains GR019, GR024, and GR026 and imaged daily with a 10 min exposure. Numbers at the bottom indicate days PI and images representing same PI day from different groups are shown. Similar to IRF-1$^{-/-}$ mice, GR024 and GR026 resulted in only a localized bioluminescence suggesting a defect in systemic spread. Rainbow scale represents approximate photon counts. FIG. 7B shows the results of bioluminescent monitoring of the virulent B. melitensis infection in vaccinated C57BL/6 mice. C57BL/6 mice vaccinated with different attenuated strains were challenged with GR023 and imaged for 10 min. Rainbow scale represents approximate photon counts.

FIGS. 8A-8B shows the results of CFU counts from livers and spleens, respectively, of C57BL/6 mice vaccinated with different attenuated strains followed by virulent GR023 challenge. The CFU counts were log transformed and the data are an average from 3-4 mice at each time point. Error bars represent the range of CFU of the samples from each time point.

FIG. 9A is a photomicrograph of large grossly visible focal calcified granulomas in C56BL/6 mice vaccinated with Rev-1. FIGS. 9B-9C are photomicrographs of large focal granulomas contained secondary changes including a central area of necrosis, neutrophil infiltration, and fibrosis with calcification.

Figure 10:
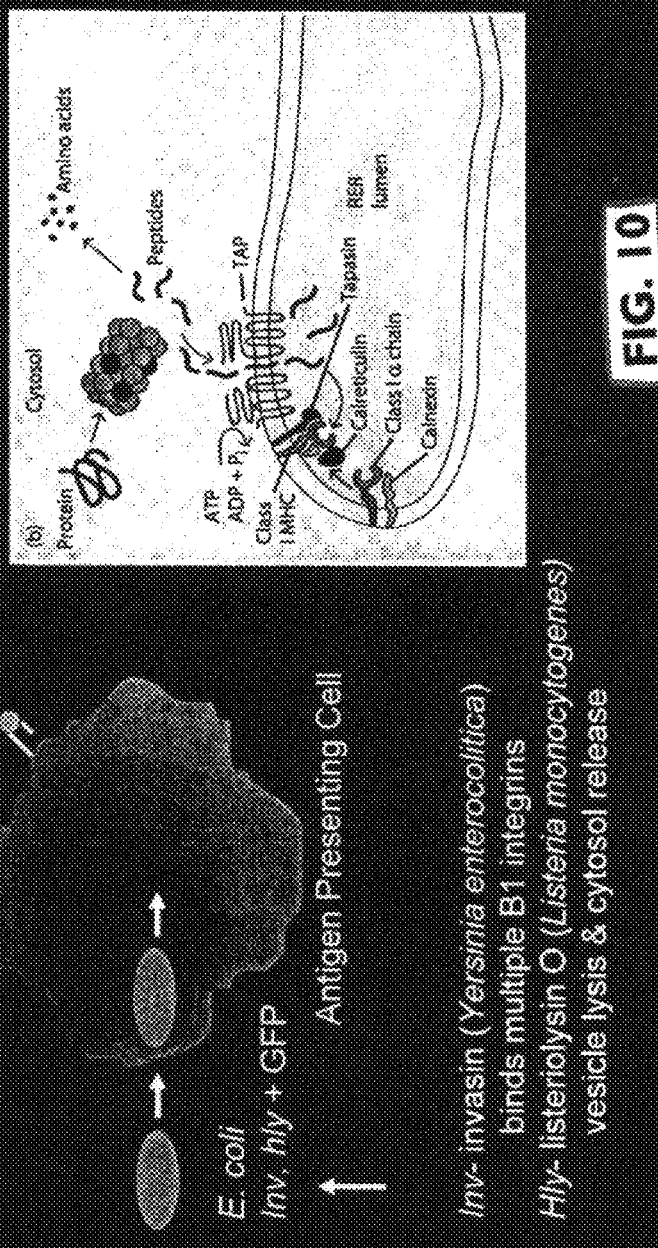

FIG. 10 illustrates the generation of antigenic peptide MHC class I complexes. As shown in the control experiment, a recombinant E. coli expressing the Yersinia enterocolitica invasin (inv) and the Listeria monocytogenes listeriolysin O (Hly) as well as a green fluorescent protein (GFPuv) was allowed to infect macrophages in culture for 24 hrs.

Figure 11:
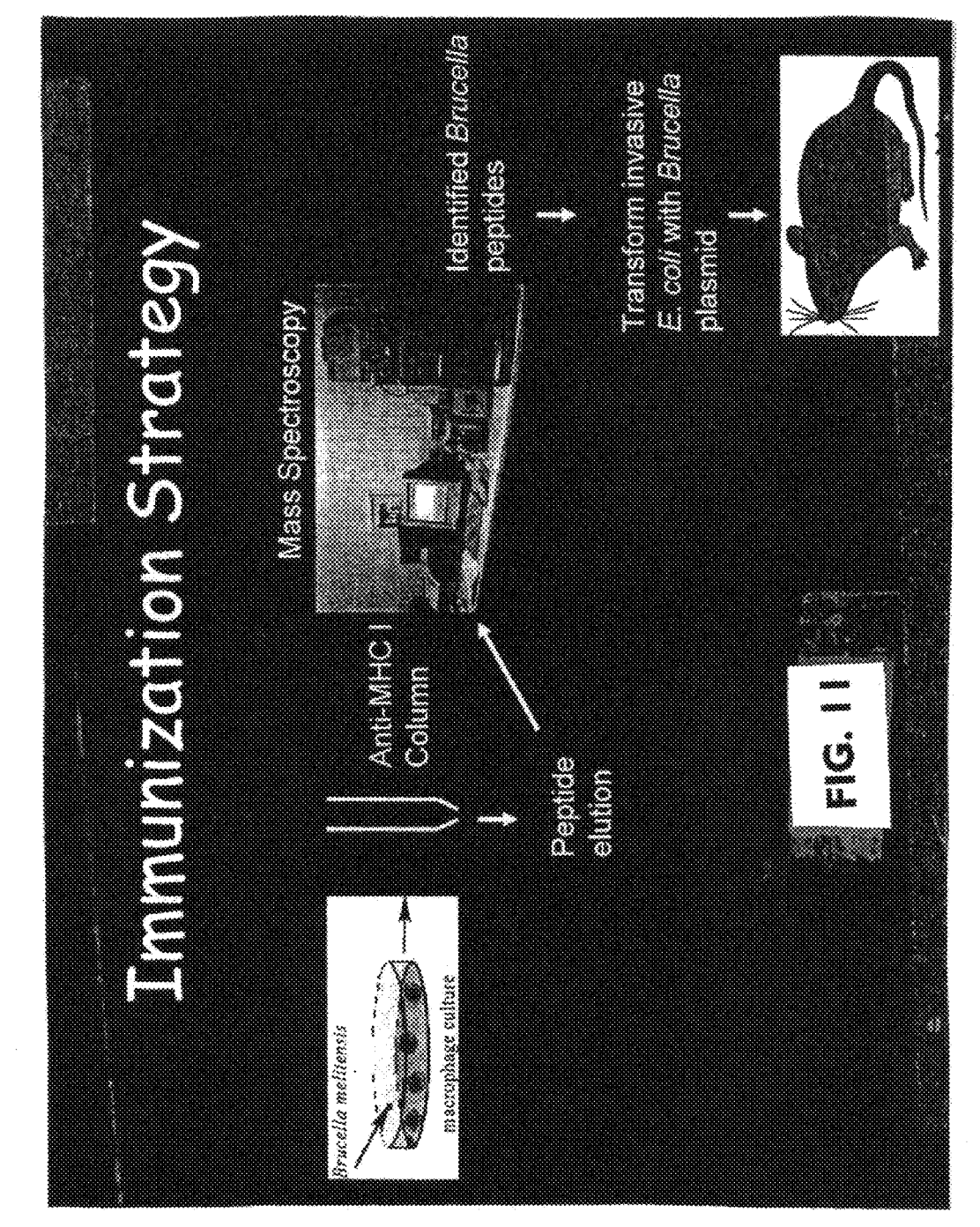

FIG. 11 shows the strategy for the identification of relevant peptide epitopes of B. melitensis. Brucella infects macrophages in culture; MHC class I proteins complexed with epitopic peptides are purified by MHC I-specific immunoaffinity chromatography, the peptides are eluted and then those peptides are characterized by mass spectroscopy. The invasive listeriolysin-expressing E. coli are transformed with plasmids expressing the peptide epitopes identified; these cells are useful for immunizing humans or animals with Brucella-specific peptides.

Figure 12:
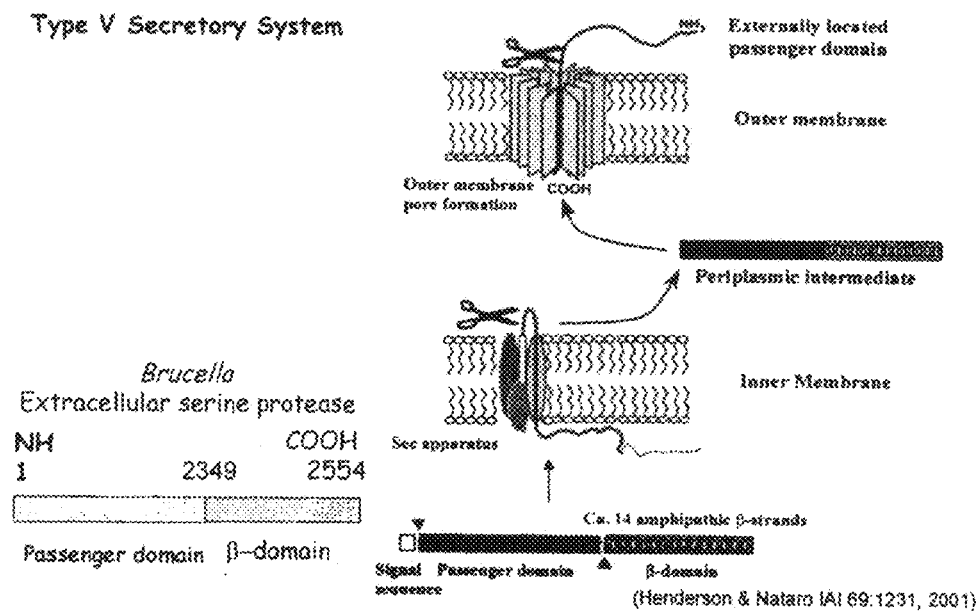

FIG. 12 provides schematic illustrations of the Brucella extracellular serine protease (encoded by ORF BMEII0148), which contains a β-domain (amino acids 2349-24554) and passenger domain (amino acids 1-2348). This structure is characteristic of autotransporters of Type V secretory proteins. The peptide of the Brucella extracellular serine protease was isolated from MHC class I molecules following a 24 hr infection of macrophage cells in culture; the peptide was identified by MALDI-TOF mass spectroscopy.

FIG. 13 summarizes the results of the demonstration project in which the Inv+ Hly+ E. coli expressing the GFPuv protein was cultured in macrophages. The MHC class I-peptide complexes were collected, the peptides were eluted and then characterized. Within the peptides isolated was NYNSHNVYIT (SEQ ID NO:25) from within the GFPuv protein.

Figures 14A, 14B:
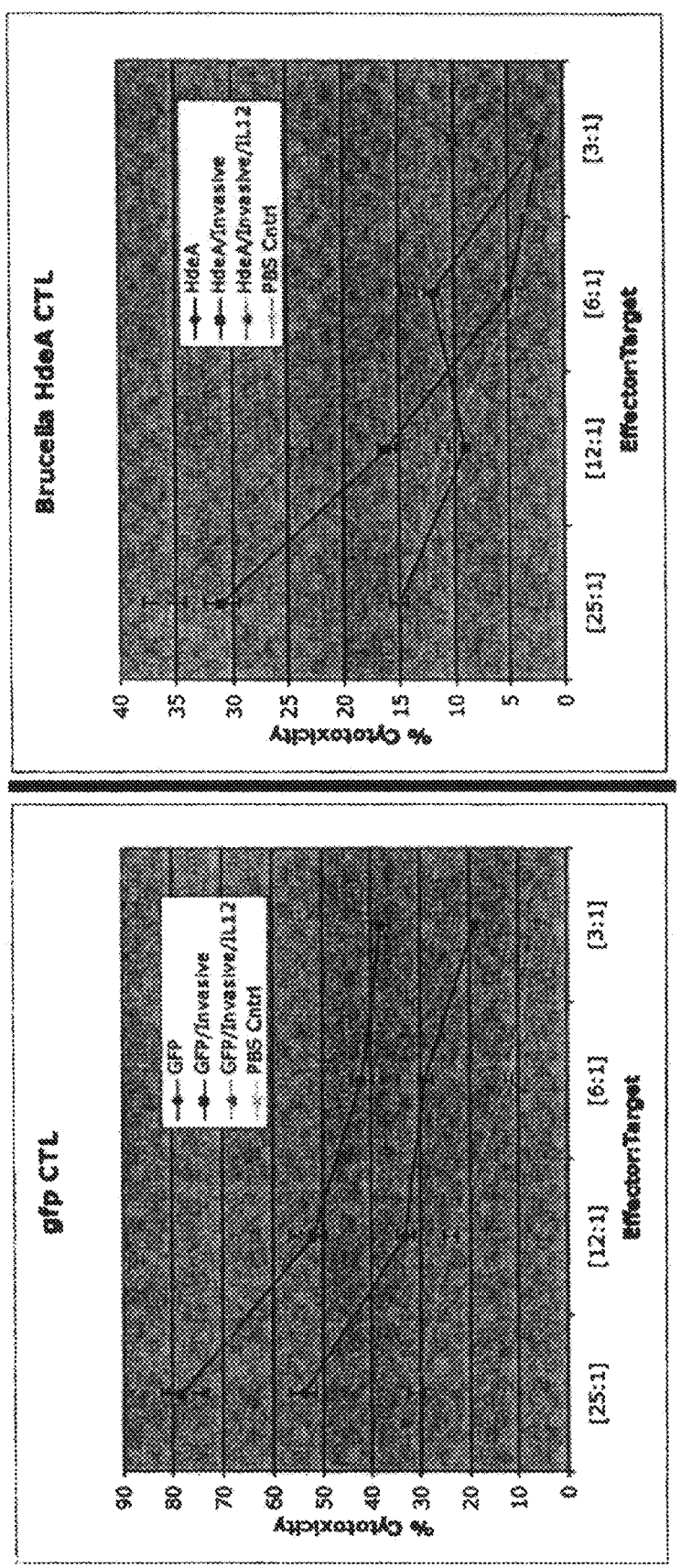

FIGS. 14A-14B summarizes the experiment carried out with the invasive Inv+ Hly+ E. coli transformed with the B. melitensis hdeA (small chaperone protein functioning in Type II secretion) gene and the GFPuv (a green fluorescent protein) gene. These E. coli strains were injected into mice intraperitoneally. The invasive E. coli generates antigen-specific cytotoxic T lymphocytes in the mice. After 6 wks, cytotoxic lymphocyte (CTL) assays were performed with transduced target cells. FIG. 14A shows the results of the CTL assay carried out with serum from mice immunized with the Inv+ Hly+ E. coli expressing the GFPuv protein. FIG. 14B shows the results of the CTL assay carried out with serum from a mouse immunized with the Inv+ Hly+ E. coli expressing the B. melitensis HdeA protein.

FIG. 15 shows the bioluminescence transposon used to produce the GR019, GR024 and GR026 mutants described herein. GR023 is an insertion mutant which was not affected with respect to virulence in the mouse model. The strategy used for analyzing the bioluminescence transposon insertion mutants is also shown.

DETAILED DESCRIPTION OF THE INVENTION

Figure 1:
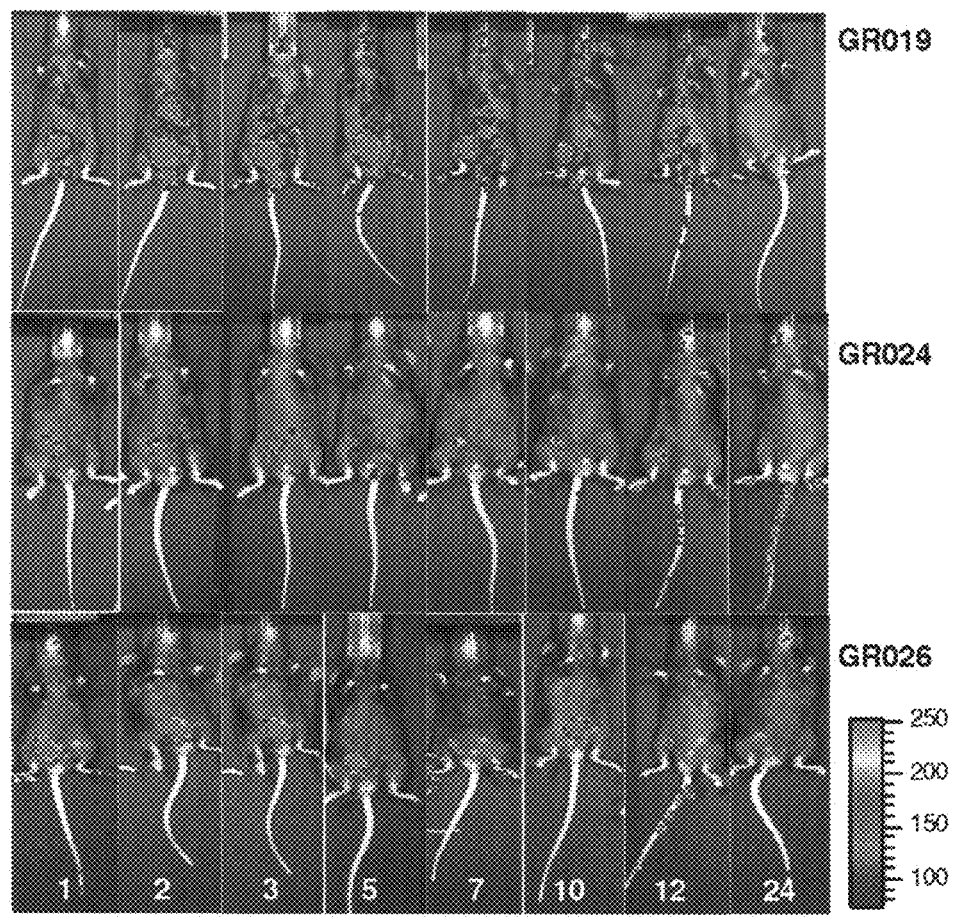
FIG. 1 shows the results of a real-time analysis of the attenuated bioluminescent *B. melitensis* strains in IRF-1$^{-/-}$ mice. IRF-1$^{-/-}$ mice were infected with $1\times10^7$ CFU of *B. melitensis* strains GR019 (virB4), GR024 (galE) and GR026 (90-91IR) and imaged daily with a 10 min exposure. Numbers at the bottom indicate days PI. Unlike GR019, infection with GR024 or GR026 resulted in a localized bioluminescence suggesting a defect in systemic spread. Rainbow scale represents approximate photon counts.

Certain bioluminescent mutants of B. melitensis are avirulent in IRF-1$^{-/-}$ mice. IRF-1$^{-/-}$ mice are highly susceptible and succumb to virulent Brucella infection; however, their response varies with the virulence of the Brucella strains (21, 22). Therefore, attenuated strains can be readily identified using these mice. We tested the three EZ::TN/lux bioluminescent mutants, GR019, GR024 and GR026 in IRF-1$^{-/-}$ mice to determine the virulence and pathology associated with these strains. In addition, we also tested two other B. melitensis mutants, BM710, a rough strain and Rev-1, a vaccine strain, so that the bioluminescent mutants could be evaluated for their ability to confer protection against challenge with virulent B. melitensis. IRF-1$^{-/-}$ mice (n=4) infected with bioluminescent strains were monitored for bacterial dissemination and persistence. Bioluminescence spread systemically in GR019 infected mice by day 1 post infection (PI), however, in the GR024 or GR026 infected mice bioluminescence localized primarily at the injection site (FIG. 1). By day 2 stronger bioluminescence was observed in many areas including the submandibular region only in GR019 infected mice. However, by day 6 GR019 infected mice began to clear the infection indicated by reduced bioluminescence and by day 24 minimal bioluminescence was observed in the extremities (FIG. 1). In contrast, in both GR024 and GR026 infected mice bioluminescence was predominantly observed at the injection site. However, by day 12, bioluminescence began to appear in the tail as multifocal lesions and was more prominent in GR024 infected mice by day 24 (FIG. 1). Mice infected with all three bioluminescent strains appeared healthy and survived longer than 24 days suggesting attenuation of these strains. Similarly mice infected with rough B. melitensis strain BM710 survived greater than 24 days suggesting attenuation. However, all Rev-1 infected mice died by 7 days PI. Although Rev-1 is a commercial vaccine, it was fully virulent in these mice. To determine the relative pathology associated with different attenuated mutants, the livers and spleens were processed for CFU and histopathology. Livers and spleens from GR019 or BM710 infected mice had lower CFU counts compared to GR024 or GR026 infected mice (Table 2). However, except for the GR026 infected group, livers and spleens from other groups had no observable histological changes (Table 2, data not shown). GR026 infected mice displayed very few multi-focal granulomas in livers and minor changes in the white pulp of spleens.

GR019, but not GR024 or GR026, is attenuated in RAW macrophages. We examined the growth of bioluminescent mutants in RAW macrophage-like cells. All three insertion mutant strains exhibited growth rates similar to that of the virulent parent strain 16M with a duplication time of 2 hr in *brucella* broth suggesting no general growth defects in GRO19, GRO24 and GRO26 (FIG. 2A). RAW macrophages were infected with each strain at a MOI of 1:50 and the growth was monitored for 72 hrs. Interestingly, only GR019 was defective in replication with a significant decrease in intracellular bacteria by 24 hr PI compared to 16M (FIG. 2B). On the other hand, both GR024 and GR026 displayed a growth distinct from GR019 or 16M. Both strains were phagocytosed more with no apparent intra-macrophage replication during 24 hr PI as bacterial levels remained constant. However, by 48 hr their growth was similar to 16M. The growth curves of GR024 and GR026 appeared as intermediate between a virulent (eg., 16M) and rough (e.g., perA, GI-2 mutant) strains of *Brucella* (41, unpublished data). Rough strains of *Brucella* are phagocytosed at even higher number and are defective in intra-macrophagic replication though they persist in higher numbers for more than 3 days in culture (35, 20, and unpublished data). This led us to suspect that both GR024 and GR026 are defective in LPS. Therefore we tested the LPS phenotype of these two mutants by the acriflavin agglutination test (6). As suggested by the macrophage growth pattern, both strains resulted in fine amorphous agglutination particles that were less intense compared to known LPS rough strains of *Brucella* (data not shown). In addition, unlike GalE mutants from other bacteria, GR024 did not show any sensitivity to galactose (1, 36, data not shown).

To determine the EZ::TN/lux insertion site in GR019, GR024, GR026, we performed 'rescue cloning' of the R6KΔori present in EZ::TN transposon from genomic DNA of each strain. Nucleotide sequencing of the rescued R6K plasmid clones in both orientations identified the transposon insertion in VirB4 (BMEII0028) for GR019, GalE homolog (BMEI0921, SEQ ID NO:28) for GR024, and in the intergenic region of BMEI1090-1091 (nucleotides 2138-3839 of SEQ ID NO:27) for GR026 (FIG. 3). The type IV secretion system encoded by 11 ORFs virB1-11 are transcribed as a polycistronic message and the disruption of these genes has been shown to attenuate *Brucella* in macrophages as well as in mice (9, 14, 34). Similarly, in GR024, the insertion disrupted the GalE homolog (BMEI0921, SEQ ID NO:28) that has been previously shown to attenuate *Brucella* (38). However, in GR026 the insertion was located in the intergenic region of two divergent ORFs BMEI1090 (complement of nucleotides 2138-3346 of SEQ ID NO:27) and BMEI1091 (nucleotides 3513-3839 of SEQ ID NO:27). Annotation of the *B. melitensis* genome suggested that BMEI1090 (complement of nucleotides 2138-3346 of SEQ ID NO:27) is the first gene in a cluster of genes that are transcribed in minus orientation, whereas BMEI1091 (nucleotides 3513-3839 of SEQ ID NO:27) is an independent transcriptional unit (FIG. 3). Based on the sequence data obtained by transposon mapping, we have concluded that the altered expression of BMEI1090 (complement of nucleotides 2138-3346 of SEQ ID NO:27) or its downstream genes is responsible for attenuation of GR026. Further, Southern blot analysis confirmed the sequencing results and also revealed the single copy insertion of the transposon in these strains.

To determine the gene(s) likely responsible for the observed phenotype of GR026, we created non-polar mutations in BMEI1090 (complement of nucleotides 2138-3346 of SEQ ID NO:27) and 1091 (nucleotides 3513-3839 of SEQ ID NO:27) by allelic replacement. The respective ORFs were replaced with a $kan^r$ marker by homologous recombination and resulting strains, GR-1090Δ and GR-1091Δ, were tested for virulence in IRF-$1^{-/-}$ mice. IRF-$1^{-/-}$ mice infected with GR-1091Δ died within 10 days similar to virulent 16M; however, only two mice infected with GR-1090Δ died and the remaining mice survived for at least 21 days (Table 2). The livers and spleens from the surviving mice had an average CFU of 6.65E+04 and 1.14E+06, respectively. Therefore inactivation of 1090 resulted in partial attenuation suggesting the phenotype associated with GR026 is likely due to altered expression of I1090 (complement of nucleotides 238-3346) and its downstream genes.

To confirm that the attenuation of bioluminescent mutants is due to disruption of transposon insertion targets and not due to secondary mutations, we complemented GR019, GR024 and GR026 with the corresponding ORFs. Because GR019 has a growth defect in RAW macrophages, the GR019 containing either pBBVirB4 or pBBVirB were tested for growth in these macrophages. Introduction of pBBVirB4 into GR019 resulted in partial restoration of the ability to grow in macrophages, as reflected by increase in intracellular bacteria at 24 hr PI (FIG. 4A). However, addition of pBBVirB, containing the entire virB operon (34), into GR019 resulted in complete restoration of growth (FIG. 4). In addition, GR019 complemented with pBBVirB but not pBBVirB4, was able to kill IRF-$1^{-/-}$ mice and restore complete virulence (FIG. 4B). Consistent with the in vitro results, mice infected with pBBVirB4-complemented GR019 did not die and contained more bacteria in livers and spleens compared to GR019 infected group (FIG. 4C).

Because both GR024 and GR026 agglutinated in the presence of acriflavin, we tested the GR024 and GR026 complemented strains for agglutination. GR024 complemented with pBBGalE resulted in no agglutination in the presence of acriflavin. Our earlier results suggested that the observed phenotype for GR026 is due to the altered expression of 11090 and its downstream genes, so we complemented GR026 with a plasmid containing 4 ORFs likely to form an operon (12). Surprisingly, addition of pBB1087-90 to GR026 resulted in much more pronounced agglutination, as seen with rough strains of *Brucella*. The functions encoded by BMEY1087-1090 are β-hexosaminidase, soluble lytic murein transglycosylase, arginyl tRNA synthetase and deoxyguanosinetriphosphate triphosphohydrolase (See Tables 5-6 and SEQ ID NOs:26-27). Consistent with the acriflavin agglutination results, both GR024 and GR026 were partially resistant to smooth-type specific Tbilisi (Tb) phage, and the addition of pBBGalE restored the susceptibility of GR024 to Tb phage. However, GR026 complemented with pBBI1087-90 was completely resistant to Tb phage suggesting a rough phenotype of the complemented strain.

Figure 5:
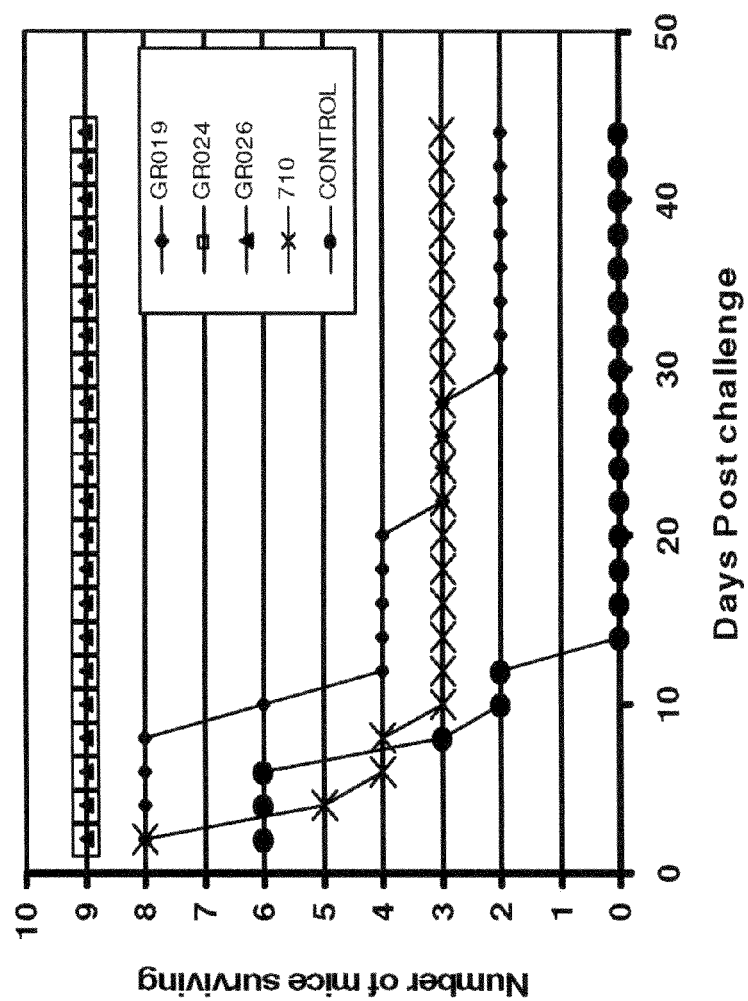
FIG. 5 demonstrates that GR024 and GR026 protect IRF-1$^{-/-}$ mice from challenge with virulent B. melitensis. IRF-1$^{-/-}$ mice (n=9) immunized with different attenuated B. melitensis strains ($1\times10^7$ i.p./mouse) were challenged with virulent B. melitensis GR023 ($1\times10^6$) and monitored for survival.

GR024 and GR026 protect IRF-1$^{-/-}$ mice from virulent challenge. IRF-1$^{-/-}$ mice, though immuno-compromised, have been shown to generate a protective immune response following vaccination with attenuated strains (22). Therefore, we tested the abilities of the attenuated bioluminescent mutants to protect IRF-1$^{-/-}$ mice from virulent challenge. IRF-1$^{-/-}$ mice (n=9) were vaccinated by intraperitoneal injection with 1×10$^7$ CFU of each *Brucella* strain, and 60 days after vaccination, the mice were challenged with 1×10$^6$ CFU of virulent bioluminescent *B. melitensis* strain GR023 (40). IRF-1$^{-/-}$ mice vaccinated with attenuated bioluminescent mutants were challenged by intraperitoneal injection when no bioluminescent bacteria were detectable. The GR023 strain of *B. melitensis* was used for challenge studies to evaluate vaccine candidates for the ability to alter the dissemination and localization of virulent *Brucella* to different tissues as visualized temporally in individual mice by imaging. All mice vaccinated with either GR024 or GR026 survived for at least 44 days, where as only 2 mice vaccinated with GR019 and 3 mice vaccinated with BM710 survived for 44 days following challenge (FIG. 5). Fifty percent of GR019 vaccinated mice died by day 12, whereas 50 percent of the BM710 vaccinated mice died by day 9 following challenge. As expected, all the unvaccinated mice died within 2 weeks following challenge with fifty percent of mice being dead by 7 days (FIG. 5).

Figure 6:
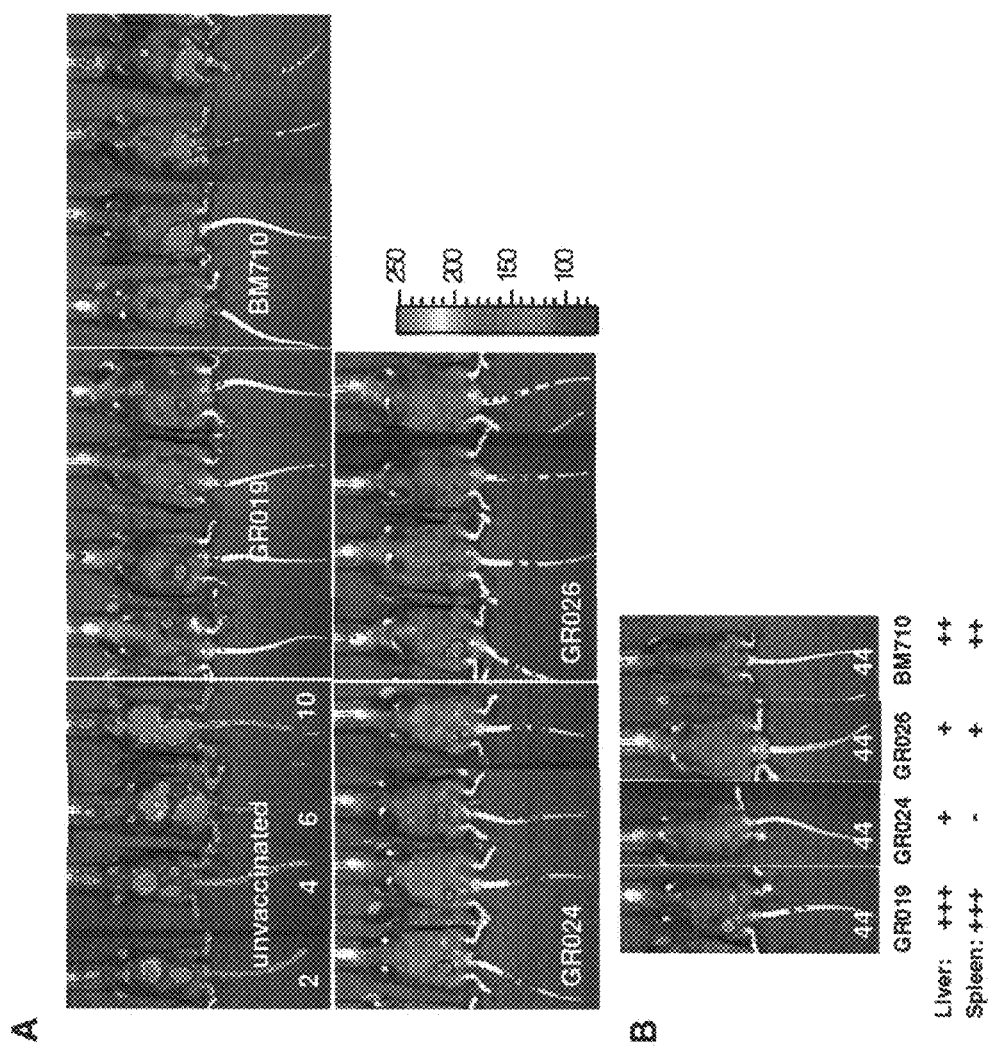
FIG. 6A shows the results of bioluminescent monitoring of virulent B. melitensis infection in vaccinated IRF-1$^{-/-}$ mice. IRF-1$^{-/-}$ mice vaccinated with different attenuated strains were imaged for 10 min following GR023 challenge. Numbers at the bottom of each figure indicate days PI and images representing same PI day from different groups are shown. Rainbow scale represents approximate photon counts.
FIG. 6B shows the results of bioluminescent imaging of surviving IRF-1$^{-/-}$ mice following challenge (upper panel) and the corresponding histological changes in livers and spleen (lower panel). Livers were scored by the number of focal granulomas observed per field of view (fov) at 4× magnification. Data represent the average number of granulomas from 8 fov. (+) 1-8; (++) 9-16; (+++) 17-24 granulomas.

The livers and spleens from surviving mice vaccinated with different strains had very similar CFUs (CFU ranges; liver: 2.2E+02-1.2E+03, spleen: 1.5E+04 to 3.4E+04). Bacteria recovered from livers and spleens of mice vaccinated with bioluminescent strains were confirmed as the GR023 challenge strain by verifying the insertion site of EZ::TN<lux> using PCR. Bioluminescent imaging of vaccinated mice following i.p. challenge revealed strikingly different dynamics of persistence and spread of virulent bacteria. Unlike the unvaccinated mice, in all vaccinated groups, bacterial spread was less extensive (See FIGS. 6A and 6B), but correlated with ability of the vaccine strain to protect from challenge. In both BM710 and GR019 vaccinated groups, bioluminescence was pronounced with systemic spread; however, in both GR024 and GR026 groups, bioluminescence was observed at the site of injection and in the tail region (see FIGS. 6A-6B). By day 44 both GR024 and GR026 vaccinated mice had no detectable bioluminescent bacteria while both BM710 and GR019 vaccinated survivors still exhibited detectable bioluminescence (FIG. 6B). Consistent with IRF-1$^{-/-}$ mice survival data, the GR024 and GR026 vaccinated mice had the least histological changes in livers and spleens. The GR024 and GR026 vaccinated mice had only few focal granulomas (less than 3/field of view) in the liver sections, while the spleens of GR024 vaccinated mice appeared normal with only minimal disorganization of the splenic white pulp in GR026 vaccinated mice. However, both GR019 and BM710 vaccinated survivors had more histological changes in both livers and spleens compared to GR024 or GR026 groups (see FIG. 6B).

Figure 9:
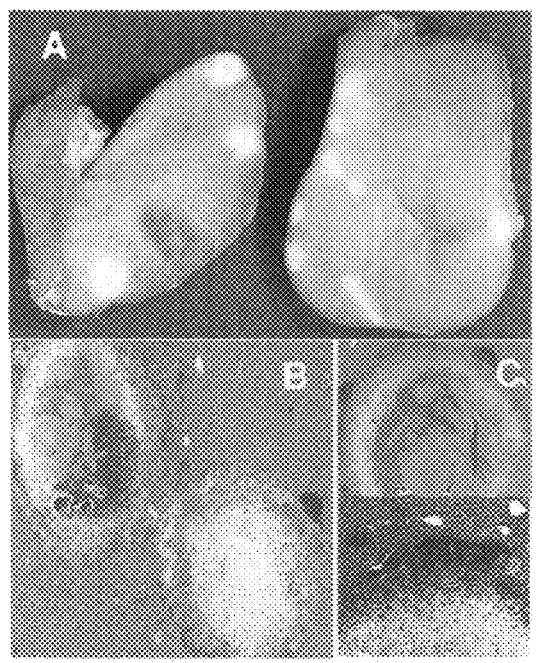

IRF-1$^{-/-}$ mice are defective in multiple aspects of the immune system (44). Therefore, to better correlate the immune protection provided by the different attenuated strains, we tested these bacterial strains in wild type C57BL/6 mice, the parental strain of IRF-1$^{-/-}$ mice. C57BL/6 mice are susceptible to virulent *Brucella* infection naturally and serve as a relevant model in which to study *Brucella* pathogenesis and immune protection. To assess the protection by different attenuated strains, we monitored bacterial clearance and histological changes in livers and spleens. In addition, the dynamics of infection by attenuated bioluminescent strains and their effects on virulent challenge were monitored by imaging. Similar to IRF-1$^{-/-}$ mice, GR019 vaccinated C57BL/6 mice had bioluminescence in systemic organs by day 1 PI; however, in GR024 or GR026 vaccinated mice bioluminescence was detected primarily at the injection site (FIG. 7A). Bioluminescence began to diminish by day 5 in all groups and by 2 weeks PI minimal or no bioluminescence was observed (FIG. 7A). However, after challenge the dynamics of virulent *Brucella* spread was similar in all vaccinated groups being limited primarily to the injection site, although bioluminescence was stronger in GR019 and BM710 vaccinated groups (FIG. 7B). Consistent with image data, all vaccinated groups had at least 2 logs less CFUs from livers and spleens at 1 week post challenge with Rev-1 and GR024 vaccinated groups containing even lower numbers of CFUs (FIG. 8). Similarly, at 2 weeks post challenge, livers from Rev-1 and GR024 vaccinated groups had significantly lower CFU compared to other groups. However, spleens from GR024 and Rev-1 vaccinated mice had lower CFU at all times compared to other groups though Rev-1 vaccinated mice had significantly fewer CFU compared to other groups (FIG. 8). To correlate the bacterial clearance with the tissue damage, histological changes were assessed in livers and spleens from immunized mice following challenge. Consistent with the bacterial clearance, GR024 and Rev-1 vaccinated mice exhibited fewer granulomas in liver at all times; however, livers from GR019 and BM710 vaccinated mice contained more granulomas (Table 3). Surprisingly, the livers from all Rev-1 vaccinated mice had large grossly visible focal calcified granulomas (FIG. 9). On the other hand, histological changes in spleens were similar in all vaccinated groups but contained fewer changes compared to unvaccinated controls (Table 3).

Mice are used extensively to study *Brucella* pathogenesis; however, the interpretation of data is often limited to CFU or histological changes observed in specific tissues. These approaches have limited our understanding of the dynamics of *Brucella* dissemination and localization into tissues beyond those organs that are conventionally used for evaluation. In this report, we describe the infection dynamics of three attenuated bioluminescent mutants in mice by visualizing how infection disseminates, bacterial preference to organs, contribution of certain *Brucella* genes to pathogenesis, and effect of vaccination on the dynamics of virulent bacterial infection. GR019, GR024, GR026, and BM710 were all attenuated in IRF-1$^{-/-}$ mice; however, Rev-1 remained virulent in these mice. Imaging of mice infected with bioluminescent strains revealed striking differences in bacterial dissemination and persistence. GR019 (VirB4), unlike GR024 or GR026, spread systemically and bioluminescence was observed in liver, spleen, testes, submandibular region and extremities early in infection, suggesting that the VirB system is not important for establishing early infection. However, the VirB system is required for *Brucella* persistence because C57BL/6 mice cleared GR019 infection faster than virulent *Brucella*. GR024 (GalE) and GR026 (90-91IR), on the other hand, failed to disseminate systemically (FIG. 1).

Figure 2:
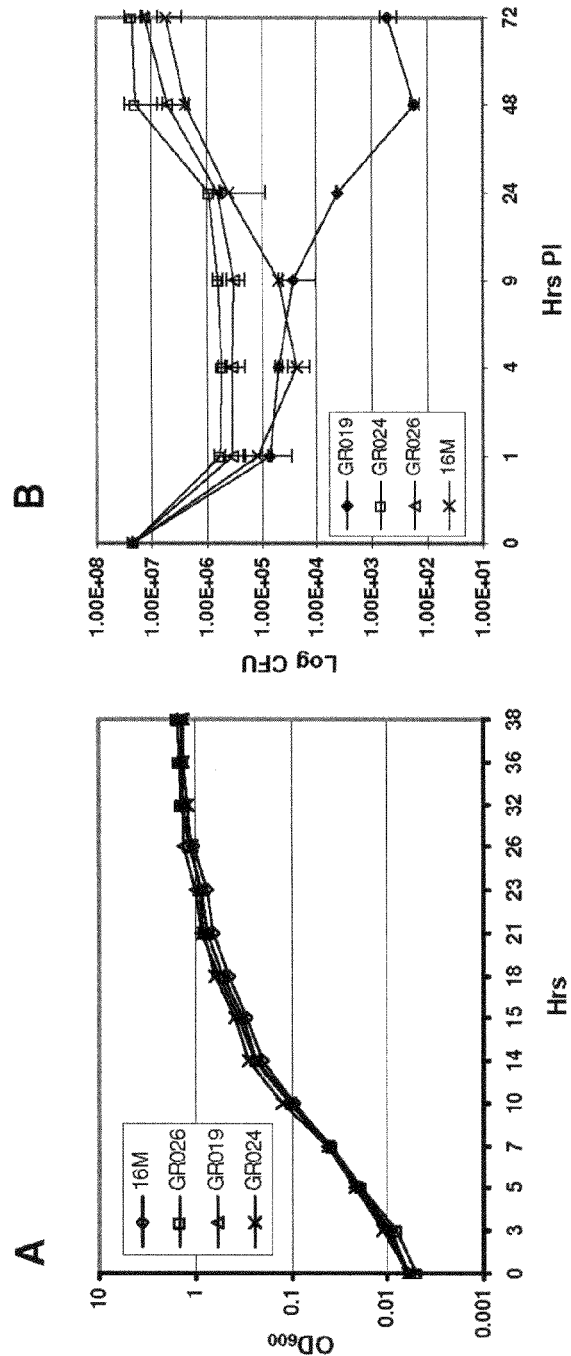
FIGS. 2A-2B illustrate replication kinetics of bioluminescent *B. melitensis* strains.
Figure 3:
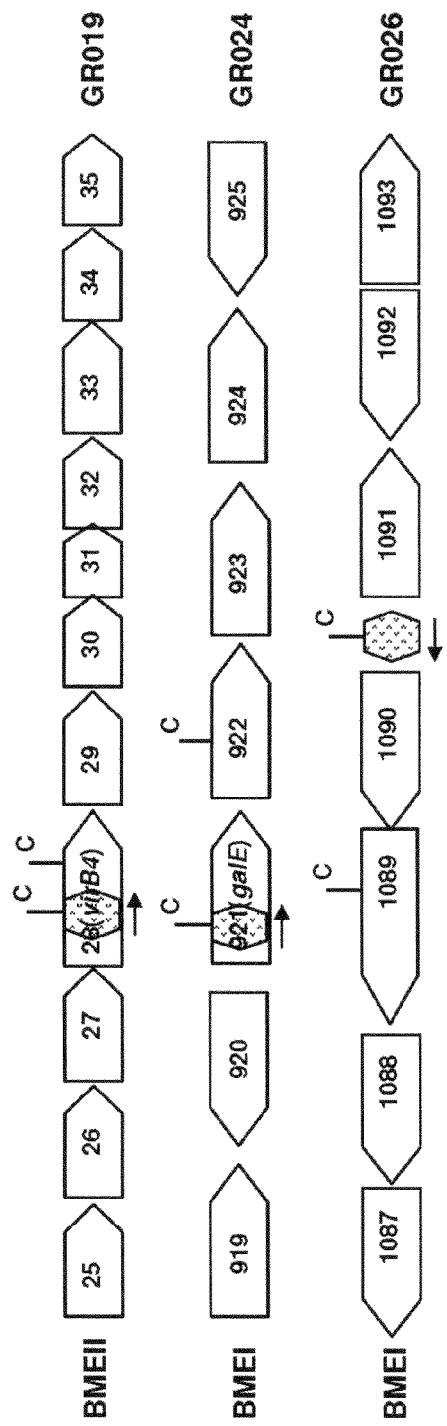
FIG. 3 provides a schematic representation of EZ:: TN<lux> transposon insertion in the three attenuated bioluminescent *B. melitensis* strains (only relevant features are shown; picture not drawn to scale). EZ::TN<lux> transposon is indicated as a closed hexagon relative to the site of insertion. The relevant ORFs upstream and downstream of the insertion are shown in open boxes with arrows indicating direction of transcription with numbers corresponding to the *B. melitensis* 16M genome sequence. The orientation of the arrow below the transposon in each strain represents the direction of Lux expression based on our sequence data. The sites for ClaI restriction enzyme used in Southern hybridization experiment are shown by the letter C.
Figure 4:
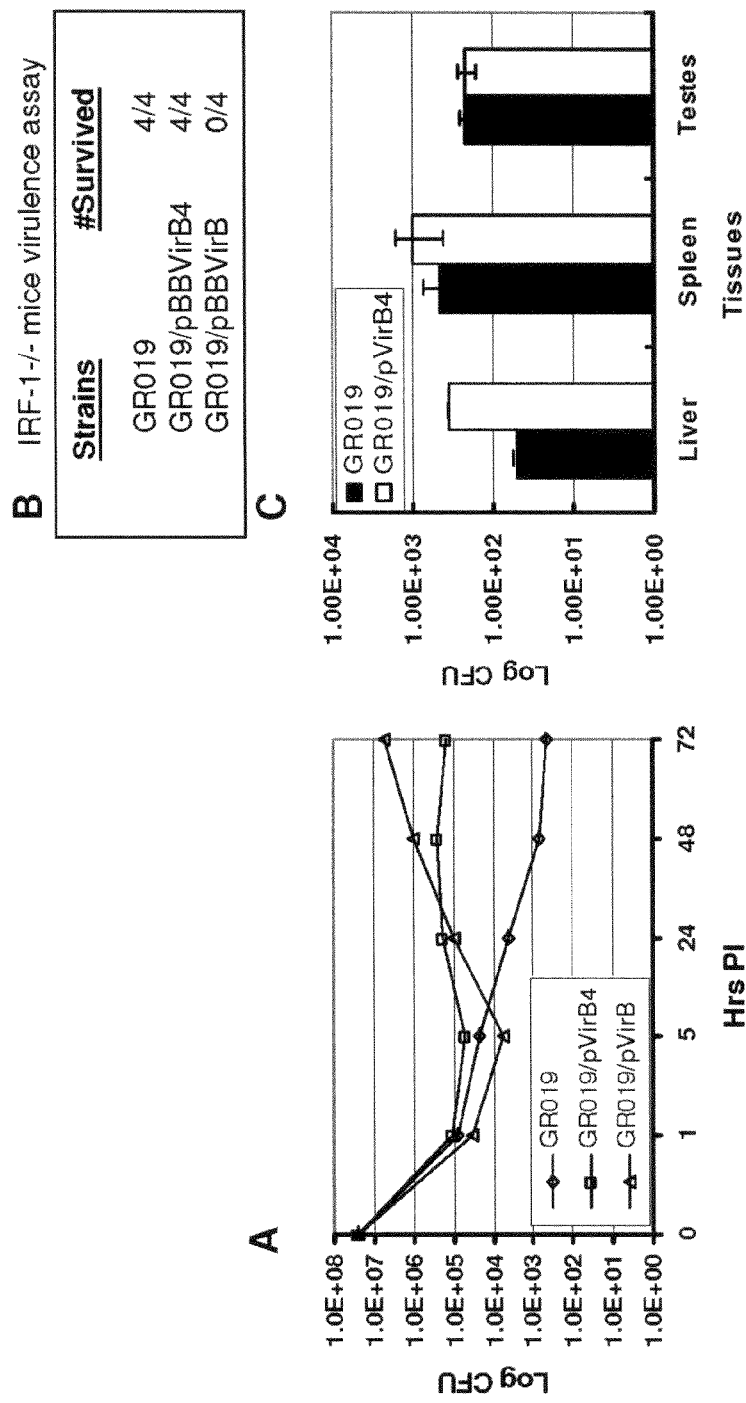
FIG. 4A illustrates complementation of GR019 with the virB operon fully restored growth in macrophages.

Interestingly, in both GR024 and GR026 infected mice, signals reappeared 12 days PI and localized in the joint-rich tail region during the later stages of infection (FIG. 1), suggesting that virulence is regulated differently in GR024 and GR026. Bioluminescent imaging is critical in identifying the contribution of *Brucella* genes to preferential tissue localization of *Brucella*. In addition, temporal bioluminescence analysis of infection revealed patterns of growth and clearance, as well as reemergence of bacteria, that is extremely difficult to observe with conventional methods. Thus, our study clearly demonstrates that conventional CFU enumeration is useful but not ideal to assess *Brucella* clearance. Importantly, only GR019 was attenuated in vitro in RAW macrophages (FIG. 2B). Therefore, in vivo imaging may provide a more comprehensive approach to identify *Brucella* virulence genes that are relevant to in vivo pathogenesis. Although GR024 and GR026 localized in the tail region in later stages of infection, no (GR024) or very minimal (GR026) histological changes in livers and spleens were observed, similar to GR019 or BM710 infected groups. Thus, these strains, individually or mixed together in combinations of two or three mutants, or two or three mutations in a single strain, are useful in the formulation of immunogenic compositions, including vaccines. candidates and bioluminescent imaging may be highly useful for vaccine selection.

Both GR024 and GR026 exhibited growth patterns in macrophages intermediate between those of smooth and rough strains of *Brucella* (41), and both strains produced very fine agglutination particles in the presence of acriflavin and were partially resistant to smooth-type specific Tb phage, suggesting that they have an altered surface structure (30). In GR024, the transposon insertion is in ORF BMEI0921 (SEQ ID NO:28), a NAD dependent epimerase/dehydratase family member that is closely related to enterobacterial galE. The galE gene is an important virulence factor in many Gram negative bacteria and is involved several cellular processes including cell membrane biogenesis (15, 17, 29, 32, 39, 42). The galE mutants in other bacteria possess defective LPS, reflecting a contribution of galE to LPS biogenesis. Likewise, acriflavin agglutination and phage susceptibility tests suggest a defect in the GR024LPS; however, GR024 was not sensitive to galactose. The galE mutants of other bacteria display a variable response to galactose, with some being sensitive while others are not sensitive to galactose (15, 19, 39). The *B. melitensis* genome contains another member of the NAD dependent epimerase/dehydratase family, BMEII0730. BMEII0730 is more closely related to UDP-glucose 4-epimerases from members of the α-proteobacteria and shares no homology with BMEI0921 (SEQ ID NO:28). A few bacterial species have two functional galE genes. In *Yersinia enterocolitica* one galE gene is linked to galactose utilization genes and the other linked to the LPS synthesis genes (39). However, neither of the *Brucella* galE genes is linked to galactose metabolic genes or to LPS biosynthetic genes. Although our results indicate that BMEI0921 plays a role in cell membrane biogenesis, whether it is involved in galactose utilization is not clear because the growth of GR024 was not inhibited in galactose-containing medium. *Brucella* genome annotation suggest that *Brucella* BMEII0730 is linked to sugar metabolism genes and may be involved in galactose utilization.

GR026 has an insertion in the intergenic region between BMEI1090 (complement of nucleotides 2138-3346 of SEQ ID NO:27) and 1091 (nucleotides 3513-3839 of SEQ ID NO:27). Further, selective allelic replacement of BMEI1090 or BMEI10191 supported the conclusion that loss of function of BMEI1090 and its downstream genes is responsible for the attenuation of GR026 (Table 1). BMEI1090 (complement of nucleotides 2138-3346 of SEQ ID NO:27) or BMEI10191 (nucleotides 3513-3839 of SEQ ID NO:27) encode HesB protein and a theoretical protein, respectively. Without wishing to be bound by any particular theory, we have concluded that 1090 and its downstream genes (1087-1090; Tables 5-6, SEQ ID NOs:26-27) form an operon. BMEI1087 (complement of nucleotides 159-1916 of SEQ ID NO:26) encodes α-hexosaminidase A, while BMEI1088 (complement of nucleotides 7908-10819 of SEQ ID NO:26) encodes soluble lytic murein transglycosylase, and these are involved in amino sugar metabolism and N-glycan biosynthesis (kegg database). Therefore, this operon may contribute to cell membrane and/or wall biogenesis. Consistent with this observation the acriflavin agglutination and Tb phage susceptibility tests suggested that GR026 has a surface structure defect. Complementation of GR026 with a plasmid containing BMEI1087-1090 ORFs resulted in more pronounced agglutination and complete resistance to Tb phage suggesting that the expression of these genes are under strict regulation.

Both GR024 and GR026 protected IRF-1$^{-/-}$ mice from virulent *B. melitensis* challenge, whereas highly attenuated GR019 and BM710 failed to protect these mice. In addition, GR024 and GR026 vaccinated mice displayed minimal changes in livers and spleens and no bioluminescence was observed at 44 days post-challenge. IRF-1$^{-/-}$ mice are defective in multiple immune components with reduced numbers of CD8$^+$T cells, functionally impaired natural killer cells, and dis-regulation of IL-12 p40 and inducible nitric oxide synthase (44). Though these mice are severely immuno-compromised, they mount an adaptive immune response sufficient to protect against virulent challenge and protection is vaccine strain dependent. Unlike, GR019, both GR024 and GR026 produced a localized but persistent infection in these mice (FIG. 1) and induced a protective immune response against virulent *Brucella* that may require some persistence of the vaccine strain. Similar results have been observed with two field vaccines stains, S19 and RB51 (23, 43). S19 persist longer and is more protective than RB51 in mice and other models (23, 43). However, S19 still possess residual virulence in domestic animals and in IRF-1$^{-/-}$ mice (22, 31), whereas RB51 is highly attenuated (22). GR024 and GR026 are highly attenuated in IRF-1$^{-/-}$ mice similar to RB51; however, they cause no or very minimal pathological changes in livers and spleen and are protective. Consistent with the IRF-1$^{-/-}$ mice data, both GR024 and GR026 provided greater protection to C57BL/6 mice than GR019 or BM 710 suggesting that IRF-1$^{-/-}$ mice may serve as an important model to rapidly assess vaccine efficacy of *Brucella* strains. Interestingly Rev-1 vaccinated mice had fewer CFU in both livers and spleens compared GR024 or GR026 vaccinated mice; however, Rev-1 vaccinated mice displayed severe liver damage with grossly visible lesions (FIG. 9) that was not seen in other groups. These lesions are likely vaccine induced as they were apparent even at 1 week post challenge. Rev-1 vaccine is used in domestic animals where *B. melitensis* is endemic with varying degrees of success (4). Although Rev-1 protected wild type mice, Rev-1 was highly virulent to IRF-1$^{-/-}$ mice (Table 2) and caused severe liver damage in wild type mice. In summary, our study revealed contribution of *Brucella* genes to in vivo pathogenesis and identified a new set of virulence genes (BMEI1090, complement of nucleotides 2138-3346 of SEQ ID NO:27, and its downstream genes). Further, the galE deficient GR024 has altered LPS structure, results in no or very minimal tissue damage, and protects against virulent *B. melitensis* challenge making it an interesting vaccine candidate for brucellosis.

While the immunization strategy has been described using particular mutants of *B. melitensis* it is understood that corresponding mutants can be made in other species of *Brucella*, for use in immunogenic compositions and vaccination strategies for protection of the cognate species of *Brucella*. It is understood that there may be some immunological cross reactivity between species of *Brucella*, the most effective protection is afforded by immunization with an attenuated mutant of the same species as that for which protection is sought.

Further to the particular insertion and deletion mutants or those having equivalent loss of function as GRO24 and GRO26 described herein, immunogenic compositions and vaccines can be prepared using such mutants in which the listeriolysin (hly) derived from *Listeria monocytogenes* is expressed. Expression of this protein results in phagosomes which are "leaky". The intracellular bacteria from the phagosomes are released into the cytoplasm of the cells in which they are reproducing, and there is a better immune response triggered. See, for example, Grode et al. (2005) J. Clin. Invest. 115: 2472-2479. For further discussions of listeriolysin, see also Giammerini et al. 2003. Protein Expr. Purif. 28:78-85; Dancz et al. 2002. J. Bacteriol. 184:5935-5945, Mengaud et al. 1988. Infect. Immun. 56:766-772 among others.

We have identified and analyzed *B. melitensis*-specific MHC class I-restricted T cell epitopes. There is additional data of MALDI-TOF Mass spectral analysis of such peptides naturally processed and associated with MHC class I molecules from macrophages infected with *Brucella* for 24 hrs. We have identified over 2500 peptides identified as *Brucella* associated with MHC class I ($2K^d$). These include peptides derived from the ORFs, as identified in Table 4.

Analysis of the peptides associated with MHC class I ($2K^d$) has revealed that a number of the peptides are likely associated with proteins previously unknown to be a part of *Brucella*'s intracellular survival strategies. For example, one of the identified peptides is from an extracellular serine protease (BMEII0148). This protein has a conserved β-domain at the carboxy-terminal region that has high sequence homology to the β-domains of autotransporters of the Type V secretory system of bacterial pathogens (see FIG. 10). Without wishing to be bound by theory, we believe that *Brucella* uses this Type V secretory system protein as an intracellular survival or virulence strategy in macrophages. Peptide epitopes identified by this strategy can be expressed by nonreplicating, non-pathogenic *E. coli* cells which have been genetically modified to express the *Yersinia enterocolitica* inv gene and the hly gene from *Listeria monocytogenes*. The invasin confers the ability to invade nonprofessional phagocytic cells. Binding of invasion to β1 integrin expressed on mammalian cells is necessary and sufficient to induce phagocytosis of the bacteria. After internalization, *E. coli* is taken into the phagosome/lysosome where lysis of the bacterium occurs. Among the various bacterial proteins released into the lysosomal vesicle, listeriolysin present in the cytoplasm of the invasive *E. coli* gains access to the phagosomal membrane, perforating it a low pH. The cytoplasmic contents of the bacteria can then escape into the cytosolic compartment of the mammalian cell through the pores generated by listeriolysin. Using this mechanism, it was demonstrated that invasive *E. coli* can be used as a delivery vector for therapeutic proteins. Furthermore, invasive *E. coli* can elicit a specific CTL response and thus, expression of *Brucella* proteins or peptides which can elicit an effective and protective T cell response within a mammalian cell and release from the phagosome via listeriolysin provides for a useful vaccine against *brucella* infections. See FIG. 13A and FIG. 13B for the results of CD8 CTL assays carried out with serum from mice immunized by intra-peritoneal injection with live Inv+ Hly+ *E. coli* expressing the GFPuv protein or the HdeA protein of *B. melitensis*. Such vaccine(s) are valuable for protection of humans and animals against the cognate species of *Brucella*; human welfare and improved animal health, with benefits to agriculture, animals in captivity and the like are achieved.

As used herein, attenuated means that a bacterial strain is reduced in virulence as compared to a "wild-type" clinical strain that causes disease in a human or particular animal; the attenuated strain does not cause disease in the human or particular animal.

With reference to a mutation, functional inactivation of a gene means that there is little or no activity of the gene product. For example, where the gene encodes an enzyme, the encoded product has less than 10%, desirably less than 5% or less than 1% of the enzymatic activity of the product from the wild type gene or there is less than 10%, less than 5% or less than 1% of the expression product. That is to say that the coding sequence can be interrupted with an inserted nucleotide or sequence, partly or wholly deleted or there can be a substitution mutation that changes the amino acid sequence of the encoded protein such that activity is significantly reduced. Alternatively, there can be an insertion, deletion or change in transcription and/or translation regulatory sequences such that expression is reduced or prevented at the level of gene transcription and/or translation of mRNA.

When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds and/or genes or mutants are intended to be exemplary, as it is known that one of ordinary skill in the art can name the same compounds differently. One of ordinary skill in the art will appreciate that methods, starting materials, mutagenic methods, compositions, vaccine regiments and immunogenic composition ingredients other than those specifically exemplified can be employed in the practice of the invention without resort to undue experimentation. All art-known functional equivalents, of any such methods, starting materials, genetic methods, and formulations and vaccination regiments are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations not specifically disclosed herein.

An immunogenic composition is one which triggers either a humoral immune response or a cellular (T cell) response, or both, in a human or animal to which the compositions has been administered. A vaccine (or vaccine composition) is an immunogenic composition, which after administered to a human or animal, which results in either no infection or infection without less severe or no symptoms upon challenge with a virulent strain of the same microorganism as the vaccine composition contained. In the context of the present invention, cellular immune responses are especially important in protecting a human or animal against infection by virulent *B. melitensis*.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art, unless otherwise defined herein.

In the present context, functionally inactivated means that a gene does not produce a biologically active gene product (there is less than 10% of the normal enzymatic activity or ligand binding activity). In the present context biological activity does not encompass triggering an immune response in a mammalian host in which the functionally inactivated gene product is expressed. However, it is intended that functionally inactivated includes those cases in which the gene is not expressed, for example, due to a large (or polar) insertion in a promoter region or other untranslated sequence.

The exact formulation, route of administration and dosage can be chosen by the individual physician in view of the patient's condition (see e.g. Fingl et. al., in The Pharmacological Basis of Therapeutics, 1975, Ch. 1 p. 1). It should be noted that the attending physician would know how to and when to terminate, interrupt, or adjust administration due to toxicity, or to organ dysfunctions, or to other negative effects. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and dose frequency, also varies according to the age, body weight, and response of the individual patient or animal. A program comparable to that discussed above also may be used in veterinary medicine.

Use of pharmaceutically acceptable carriers to formulate the immunogenic compositions herein disclosed for the practice of the invention into dosages suitable for administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

One skilled in the art would readily appreciate that the present invention is well adapted to carry out the objects and obtain the ends and advantages mentioned, as well as those inherent therein. The compositions and methods and accessory methods described herein are representative of preferred embodiments and are not intended as limitations on the scope of the invention. Changes therein and other uses will occur to those skilled in the art, which are encompassed within the spirit of the invention, are defined by the scope of the claims.

Monoclonal or polyclonal antibodies, preferably monoclonal, specifically reacting with a protein or other cellular component of interest may be made by methods known in the art. See, e.g., Harlow and Lane (1988) *Antibodies: A Laboratory Manual*, Cold Spring Harbor Laboratories; Goding (1986 and subsequent editions) *Monoclonal Antibodies: Principles and Practice,* 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol*. 218, Part I; Wu (ed.) (1979) *Meth Enzymol*. 68; Wu et al. (eds.) (1983) *Meth. Enzymol*. 100 and 101; Grossman and Moldave (eds.) *Meth. Enzymol*. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York. Abbreviations and nomenclature, where employed, are deemed standard in the field and commonly used in professional journals such as those cited herein.

All references cited herein are hereby incorporated by reference to the extent there is no inconsistency with the present disclosure. These references indicate the level of skill in the relevant arts.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Bacterial Strains, Plasmids, and Growth Conditions

Bacterial strains and plasmids used in this study are listed in Table 1. Strains GR019, GR024, and GR026 are the EZ::TN-lux transposon insertional mutants of *B. melitensis* 16M containing the promotorless lux operon. A schematic illustration of the bioluminescence transposon and the mutagenesis and analysis strategy is shown in FIG. 15. *B. melitensis* Rev-1 is an attenuated strain of virulent *B. melitensis* 6056 (2, 13) and is used as a vaccine for brucellosis in small ruminants (4). *B. melitensis* 710 is a spontaneous rough mutant of Rev-1 isolated from vaccinated sheep and is phenotypically identical to Rev-1 except for the rough LPS. GR023 is a virulent bioluminescent strain of *B. melitensis* 16M (40) used for challenge studies. All *Brucella* strains were grown in *brucella* broth (Difco, Detroit, Mich.). Ampicillin 100 μg/ml, chloramphenicol 20 μg/ml, kanamycin 50 μg/ml, and zeocin; 50 μg/ml for *E. coli* and 250 μg/ml for *Brucella* were added to the medium as necessary. *Brucella* strains were grown at 37° C. with shaking unless otherwise stated. *E. coli* strain DH5α (Invitrogen) and EC100D™ pir+ (Epicentre, Madison, Wis.) were grown in LB broth (Difco).

Suicide vectors pGR026-90K and pGR026-91K for generating deletions in BMEI1090 (complement of nucleotides 2138-3346 of SEQ ID NO:27) and BMEI1091 (nucleotides 3513-3839 of SEQ ID NO:27), respectively, were created using pZErO-1. To construct pGR026-90K, approximately 1 kb DNA sequences upstream and downstream of the deletion target was amplified by PCR (upstream: forward 5'atcaac ggtaccCGTTCAGCGCGTCGAGATCG (SEQ ID NO:1) and reverse 5'gctctaggatccGACTGATAATTATGCCGTGCG (SEQ ID NO:2), downstream: forward 5'acagtc ggatccATAACCGAAGCCTATTCCTTC (SEQ ID No;3) and reverse 5'ggtaacctgcagCGAACGTGCCCGCAT CAT (SEQ ID NO:4)) and cloned into pZErO-1 to generate plasmid pGR026-90. Appropriate restriction sites were included in the PCR primers to facilitate the insertion of the kanamycin resistance (kan$^r$) gene from pUC4K between the 2 fragments to generate pGR026-90K. Bases added to the 5' end of each primer to provide restriction sites are underlined. To construct pGR026-91 K, the desired deletion target was amplified with approximately 1 kb upstream and downstream sequences using specific primers (forward 5'agatac ggtaccTCTTCCATCGTTCCGGGCCT (SEQ ID NO:5) and reverse 5'catgcatctagaGACGCCGTTGATGTTCCATGTA (SEQ ID NO:6)) and cloned into pZErO-1 to generate pGR026-91. Then, inverse PCR was performed on pGR026-91 using primers (5'tcttgagaattcCCCAATGCGACCGCTT (SEQ ID NO:7) and 5'gattca gaattcTTTGGCGATCCGCCTGGCA (SEQ ID NO:8)) designed to amplify all but the deletion target. The inverse PCR product was digested with restriction enzyme and ligated to the kan$^r$ gene fragment to generate the final suicide vector pGR026-91 K.

To construct plasmids pBBVirB4, pBBGalE, and pBB11087-90, DNA sequences encoding the respective ORFs were amplified using primers (VirB4: forward-5'agagagGGTACCCATGTTCATATTGCCGCTGATCG (SE1Q ID NO:9) and reverse-5'agagag GGATCCTGCTGGTTACA GTCAGGGCGAAT (SEQ ID NO:10); GalE: forward 5'agagag GGTACCAAAGCCCGGTAAAACGATTGATG (SEQ ID NO:11) and reverse 5' agagag GGATCCGTTCCGGCATTTTCTGGCAAA (SEQ ID NO:12); 1087-90: forward-5'agagag ACTAGTTGTGCCGTCGTTTCCACCTG (SEQ ID NO:13) and reverse-5' agagagCTCGAGAGGGACGGGGA TCGGGTTAT (SEQ ID NO:14). PCR products were digested with restriction enzymes and ligated to pBBR-MCS4 to generate the complementation plasmids.

Example 2

Mapping of the EZ::TN/lux Transposon Insertion Site

The site of transposon insertion in GR019, GR024, and GR026 mutants was identified by rescue cloning. Two micrograms of genomic DNA from each strain was digested to completion with NcoI to generate a fragment with intact transposon and flanking sequences. Digested DNA was religated using a FastLink DNA ligation kit (Epicentre). Ligations were dialyzed and transformed into electrocompetent EC100 Dpir+ cells (Epicentre) and plated on LB agar containing kanamycin. Two independent kan$^r$ colonies were selected, the plasmid was extracted and the site of insertion was identified by sequencing the plasmid DNA bi-directionally using outward primers (40). Sequencing was performed using dye terminators at the DNA sequencing core facility, University of Wisconsin Biotechnology Center. Sequences were compared to the 16M genome sequence to determine the site of insertion.

For Southern hybridization, 10 μg of genomic DNA was digested with ClaI and separated in a 0.7% agarose gel by electrophoresis. The single copy insertion of the transposon at the expected location was detected using the $kan^r$ gene as a probe. A 700 bp internal fragment of the $kan^r$ gene was amplified from pUC4K using primers, KanF2; 5'GCTCGAGGC-CGC GATTAAAT (SEQ ID NO:15) and KanR2; 5'TCAC-CGAGGCAGTTCCATAGGA (SEQ ID NO:16), labeled with North2South Direct HRP detection and labeling kit (Pierce) and used as a probe.

Example 3

Inactivation of BMEI1090 and BMEI1091 in 16M

To generate specific deletions, suicide vectors pGR026-90K and pGR026-91K were electroporated into *B. melitensis* 16M. Cells were plated on *brucella* agar containing kanamycin. To select for double recombinants, the $kan^r$ colonies were checked for sensitivity to zeocin ($zeo^s$). The resulting $kan^r$ and $zeo^s$ clones were streak purified, and one such purified clone was used for further study.

Example 4

Macrophage Infection

The macrophage-like RAW 264.7 cells were cultured in RPMI supplemented with 10% heat-inactivated fetal calf serum. For macrophage growth assays, 24-well microtiter plates were seeded with $5 \times 10^5$ macrophages/well and infected with different *B. melitensis* strains at 1:50 multiplicity of infection. Cells were incubated for 1 hr at 37° C. in 5% $CO_2$, extracellular bacteria were removed with 3 washes of PBS followed by treatment with gentamicin 25 µg/ml for 30 min. Following gentamicin treatment, the cells were maintained with medium containing 5 µg of gentamicin/ml. At specified times, cells were washed with PBS three times, lysed with 0.1% Triton-X, and plated on *brucella* agar to determine intracellular bacterial counts. All experiments were performed in duplicate.

Example 5

IRF-$1^{-/-}$ Mice Virulence Assay

Groups of 6-9 week old IRF-$1^{-/-}$ (n=4) were infected intraperitoneally (i.p.) with $1 \times 10^7$ CFU of GR019, GR024, GR026, Rev-1 and BM710 strains. Infected mice were housed in a biosafety level 3 facility and monitored for survival (virulent *Brucella* kills these mice within 14 days; 21). For imaging, mice were anesthetized with isoflurane, and bioluminescence was recorded after a 10 min exposure using a CCD camera (Xenogen, Alameda, Calif.). From the surviving mice, livers and spleens were collected aseptically, homogenized in PBS and plated on *brucella* agar. Plates were incubated at 37° C. for 4 days, and CFU were determined. For histology, a portion of livers and spleens were collected and fixed in 10% formalin, 5 µm sections were prepared, stained with hemotoxylin and eosin and microscopically examined.

Example 6

Vaccination and Challenge Studies

IRF-$1^{-/-}$ mice 6-9 weeks old (n=9/group) were vaccinated with $1 \times 10^7$ CFU i.p. with *B. melitensis* strains GR019, GR024, GR026, or BM710 in 200 µl PBS. As a control, a group of 10 mice were injected with 200 µl PBS. Similarly, C57BL/6 mice (n=20/group) were vaccinated i.p. with $5 \times 10^7$ CFU with each of the above strains and the Rev-1. Mice were imaged daily using a CCD camera until challenge. After 60 days, both IRF-$1^{-/-}$ and C57BL/6 mice were challenged with $1 \times 10^6$ CFU of virulent bioluminescent *B. melitensis* GR023 i.p. Following challenge, mice were imaged with 10 min exposure using a CCD camera and dissemination of virulent bioluminescent GR023 in different groups was monitored.

For IRF-$1^{-/-}$ mice, the survival was recorded in different groups following virulent challenge. At 44 days post challenge, livers and spleens from surviving mice were processed for CFU enumeration. For C57BL/6 mice, to determine CFU in livers and spleens, 4 mice from each group were killed at weekly intervals. Portions of the livers and spleens were weighed and then homogenized in PBS. Homogenates were serially diluted, plated on *brucella* agar with or without antibiotic and colonies were counted after 72 hr of incubation at 37° C. To determine the histological changes at each time, a portion of livers and spleens were collected, fixed in 10% formalin, and 5 µm sections were prepared and stained with hematoxylin and eosin.

Example 7

Identification of *Brucella*-Specific MHC Class I-Restricted T Cell Epitopes

Raw264.7 mouse macrophage cells (haplotype $H2^d$) are infected (MOI 1000) with *B. melitensis* cells for 48 hrs. Infected cells, along with uninfected control cells ($2 \times 10^9$ each) are harvested by scraping, and membrane proteins are extracted using Mem-PER (Pierce Chemical Co., Rockford, Ill.). The extract is dialyzed overnight in 0/5% CHAPS buffer to prepare for immunoprecipitation. H2-$D^d$/peptide co-immunoprecipitation is performed using Seize Primary Immunoprecipitation Kit (Pierce) couple with anti-mouse H-$2D^d$ monoclonal antibody that recognizes a conformationally sensitive epitope of H-$2D^d$ (5589125, BD Biosciences Pharmingen, San Diego, Calif.). After elution of the MHC I/peptide complex in acidic conditions, the peptides are separated from MHC I components by passing through a 5 kDa MWCO filter (Millipore, Billerica, Mass.). Micro BCA protein assays are performed on the peptide mix, and the peptides are separated, sequenced and analyzed by liquid chromatograph/mass spectrometry.

Alternatively, the RAW264.7 mouse macrophage cells are infected with invasive *E. coli* expressing GFPuv for identification of infected cells (MOI 100 24 hr infection). The results demonstrated that MHC I and associated peptide can be identified, and the invasive *E. coli* vaccine vector can be used to deliver antigen to cells for processing and presentation by MHC class I. In this example, of eight H2-$D^d$ nonamers from Infected Raw264.7 cells, one (NYNSHNVYI, SEQ ID NO:17) was specific to the GFPuv protein. Other sequenced peptides included HYLSTQSAL (SEQ ID NO:18), LFTGV-VPIL (SEQ ID NO:19), KFICTTGKL (SEQ ID NO:20), DFKEDGNIL (SEQ ID NO:21), LPVPWPTLV (SEQ ID NO:22), EYNYNSHNV (SEQ ID NO:23) and TPIGDGPVL (SEQ ID NO:24).

TABLE 1

Bacterial strains and plasmids used in this study.

| Strains or Plasmids | Descriptions | Reference or source |
|---|---|---|
| Strains | | |
| 16M | Wild type strain of *B. melitensis* | ATCC |
| DH5α | *E. coli* strain used for cloning | Invitrogen |
| EC100Dpir+ | *E. coli* strain used for rescue cloning | Epicenter |

TABLE 1-continued

Bacterial strains and plasmids used in this study.

| Strains or Plasmids | Descriptions | Reference or source |
|---|---|---|
| GR019 | Bioluminescent *B. melitensis* with EZ::TN transposon inserted in the virB4 gene | This study |
| GR023 | Bioluminescent *B. melitensis* strain used for mice challenge studies | 40 |
| GR024 | Bioluminescent *B. melitensis* with EZ::TN transposon inserted in the galE homolog | This study |
| GR026 | Bioluminescent *B. melitensis* with EZ::TN transposon inserted in the intergenic region of BMEI1090-1091 | This study |
| BM710 | Spontaneous rough mutant of *B. melitensis* Rev-1 strain | This study |
| Rev-1 | *B. melitensis* 16M vaccine strain | 2 |
| GR-1090Δ | *B. melitensis* 16M with BMEI1090 replaced with $Kan^r$ | This study |
| GR-1091Δ | *B. melitensis* 16M with BMEI1091 replaced with $Kan^r$ | This study |
| Plasmids | | |
| pBBR-MCS4 | Broad host range plasmid. Ap | 25 |
| pZErO-1 | Cloning vector. Zeo | Invitrogen |
| pUC4K | Source of kanamycin resistance marker. Km | Amersham |
| pGR026-90 | pZero-1 containing BMEI1090 with approximately 1 kb upstream and downstream sequences. Zeo | This study |
| pGR026-90K | pGR026-90 containing $kan^r$ marker replacing ORF I1090. Zeo, Km | This study |
| pGR026-91 | pZero-1 containing BMEI1091 with approximately 1 kb upstream and downstream sequences. Zeo | This study |
| pGR026-91K | pGR026-91 containing $kan^r$ marker replacing ORF I1091. Zeo, Km | This study |
| pBBVirB | pBBR-MCS1 containing the virB region used for complementation. Cm | 34 |
| pBBVirB4 | pBBR-MCS4 containing *B. melitensis* virB4 ORF used for complementation. Ap | This study |
| pBBGalE | pBBR-MCS4 containing *B. melitensis* galE ORF used for complementation. Ap | This study |
| pBBI1087-90 | pBBR-MCS4 containing *B. melitensis* BMEI1087-90 ORFs used for complementation. Ap | This study |

Ap; Ampicillin,
Zeo; Zeocin,
Km, Kanamycin,
Cm; Chloramphenicol,

TABLE 2

IRF-$1^{-/-}$ mouse virulence assay.

| Strains | # of mice infected | # of mice survived | Tissue damage[a,b] Liver | Tissue damage[a,b] Spleen | CFU counts[a] Liver | CFU counts[a] Spleen |
|---|---|---|---|---|---|---|
| 16M | 4 | 0 | Severe | Severe | 1.9E+10 | 1.6E+10 |
| GR023 | 4 | 0 | Severe | Severe | 1.5E+10 | 1.4E+10 |
| GR019 | 4 | 4 | None | None | 1.3E+03 | 1.0E+04 |
| GR024 | 4 | 4 | None | None | 9.5E+03 | 1.2E+04 |
| GR026 | 4 | 4 | Minimal | Minimal | 1.3E+04 | 3.2E+05 |
| BM710 | 4 | 4 | None | None | 2.0E+02 | 4.5E+03 |
| Rev-1 | 4 | 0 | ND[d] | ND | ND | ND |
| GR-1090Δ | 4 | 2[c] (1090) | ND | ND | 6.6E+04 | 1.1E+06 |
| GR-1091Δ | 4 | 0 (1091) | ND | ND | ND | ND |

[a]CFU counts and tissue damage were assessed two weeks post infection except for the 16M and GR023 infected groups for which tissues were collected when mice were moribund.

[b]Liver damage was assessed based on the number of focal granulomas and spleen damage was assessed based on the loss of architecture of white and red pulp. Tissue sections were visualized at 4X magnification and damage was assessed by observing more than 5 fields of view.

[c]Survived for at least 3 weeks.

[d]Not determined

TABLE 3

Liver and spleen damage in C57BL/6 mice vaccinated with different *Brucella* strains following a virulent challenge.

| Treatment groups | Weeks PC Liver[a] 1 | 2 | 3 | 4 | Spleen[b] 1 | 2 | 3 | 4 |
|---|---|---|---|---|---|---|---|---|
| GR019 | ++ | +++ | ++++ | +++ | +++ | ++ | ++ | + |
| GR024 | ++ | ++ | ++ | + | ++ | ++ | ++ | + |
| GR026 | ++ | ++ | ++ | + | +++ | ++ | + | − |
| Rev 1 | + | ++ | ++ | + | ++ | +++ | ++ | + |
| 710 | +++ | ++++ | ++ | ++ | + | ++ | ++ | ++ |
| Control | +++++ | +++++ | +++ | ++ | ++ | ++++ | ++++ | ++ |

[a]Livers were scored by the number of focal granulomas observed per field of view at 4X magnification. At each time, 8 fields were counted to determine the number of granulomas: (+) 1-8; (++) 9-16; (+++) 17-24; (++++) 25-32; (+++++) 33-40 granulomas.

[b]Spleens were scored on loss of white and red pulp architecture. At each time, 8 fields (4X) were scored using the following criteria: (−) normal spleen or no noticeable changes; (+) enlarged follicles, increased cellularity, and white pulp; (++) hyperplasia, with a significant increase in follicle size, and white pulp; (+++) increased red pulp, early loss of architecture, and the diminution of white pulp; (++++) severe loss of architecture, and a dramatic reduction in the number of follicles.

TABLE 4

*Brucella* peptides identified from MHC I molecules*

| | |
|---|---|
| BMEII0160 | Flagellar Hook-associated protein |
| BMEII0148 | Extracellular serine protease |
| BMEII0793 | Multidrug resistance efflux pump |
| BMEI1895 | Outer membrane protein |
| BMEII0976 | ABC transporter ATP-binding protein |
| BMEI1715 | Maltose transport permease |
| BMEII0862 | Dihydrodipicolinate synthase |
| BMEII0126 | Amino acid permease |
| BMEII0348 | 4-aminobutyrate aminotransferase |
| BMEI1744 | Glucose-resistance amylase regulator |
| BMEI1427 | UDP-4-dehydro-6-deoxy-2-actamido-D-glucose |
| BMEI0943 | Vitamin B12-dependent ribonucleotide reductase |
| BMEI0864 | NifR3 Nitrogen regulation |
| BMEII0749 | Hypothetical protein |
| BMEI0903 | Hypothetical protein |
| BMEI1718 | Hypothetical protein |

*Examples from over 2,500 different peptides isolated from MHC I H-$2K^d$

TABLE 5

Nucleotide sequence encompassing two open reading frames of the Brucella melitensis 16M genome (SEQ ID NO: 26).

```
LOCUS       AE009548               10975 bp    DNA     linear   BCT 20-MAR-2003
DEFINITION  Brucella melitensis 1GM chromosome I, section 105 of 195 of
            the complete sequence.
ACCESSION   AE009548 AE008917

VERSION     AE009548.1  GI: 17983048

ORGANISM    Brucella melitensis 16M

AUTHORS     DelVecchio et al. 2002. The genome sequence of the
            facultative intracellular pathogen Brucella melitensis.
            Proc. Natl. Acad. Sci. USA 99: 443-448)

FEATURES    Location/Qualifiers
     gene       complement (6688 . . . 7740)
                /gene = "BMEI1087"
     CDS        complement (6688 . . . 7740)
                /gene = "BMEI1087"
                /EC_number = "3.2.1.52"
                /product = "BETA-HEXOSAMINIDASE A"
                /protein_id = "AAL52268.1"
                /db_xref = "GI: 17983056"

/translation = "MIQQDNSRKSRMKECKAWIAGISGTKLTPDEIAFFRDETPWGFI
LFARNVESLEQVSELTAHLRDLTGLDQTPVFIDQEGGRVQRLRPPLVPNYPSASEIGA
IYARDKEKGLRAAWLHARLHAFDLLKVGVNADCLPVLDVPVEGAHDVIGMRAYSKNPH
AVAEMGRAAAEGLLAGGVLPVVKHMPGHGRAFSDTHKELARVSVALNELVAHDFVPFK
ALNDLPMAMTAHVVFDCIDPERPSTLSPTVINTIIRDVIGFDGLVISDDISMKALSGD
LGDITDGIVTAGCDIVLYCSGVMEELVKVAARVPVLDGKAKRRAELAEVYAGDPDLSD
            EDEVRAEFNAMFEPIA"

gene       complement (7908 . . . 10817)
                /gene = "BMEI1088"
     CDS        complement (7908 . . . 10817)
                /EC_number = "3.2.1."
                /product = "SOLUBLE LYTIC MUREIN TRANSGLYCOSYLASE"
                /protein_id = "AAL52269.1"
                /db_xref = "GI: 17983057"

ORIGIN
    1 aggctgccat tgctcaaaat caatgcaact gaagccgttc cgacaaaagc gcgaagcggt
   61 tttttggaat catcctcaaa caaaatcttg gagcgggatg atggttggac ttaaattcaa
  121 cccgttttag agcgcgtttc gatctgattg aatcagatcg gcgctctaat cctttgtttt
  181 gacgcgcatc ttttccgaaa accgtttcac acttttcggg atgcgctcta aagaacggaa
  241 gacgtgcctt cgatgaacgg ctgatatcga accggcatga ggtcttcctg ttcaaaacgg
  301 cttccaacct ttgaaatccg cgtcatgatc tggcgtccat cgccagggcg gatcggggct
  361 atcaggacgc catgggtggc gagcagttca acgaaatggc gcgtgcacctc atcgcatgcg
  421 agccagatga caatgcggtc aaacggcccg cccggcatac cgtggcgccc gtctgtatgt
  481 ttcaccatga tattctcgcg cttcagcgaa acgaactgct ggagagcgtg gtcgcagagt
  541 tttcgatacc gttccaccgt cgttacacgg ccggacagca aggacataac ggcggcggta
  601 aagccggagc cggtgccgat ttccagaacc cgatggcgcg gctcaagctt cagggcggaa
  661 atgacgcgcg cctgatcgtc tatgccttcc atatattcac cgcaatcaag cggcgcggtt
  721 cgcgggctat aggcaagatg cgaccatgcc gccgccagaa agctctggcg cggcgttgct
  781 tcaattgccg caaaaagttg cggatcatca atgctgtgcc cacgcatccg cagaacaaag
  841 gatgcaaatc cctcccggtc cgaaagccgc gggcgttcag acgttgccgc cctcatgctt
  901 ccactccaag cgccgcgccc agttctgcac gaaccttatg agcggtcaga tcaaggtgga
  961 gtggggtcac tgaaatgcaa cccgaacgga tggcagcaat atcgctgtcg tcggcaaccg
 1021 gagccttgcc gcgaccgaaa tgcagccaga aataagggaa accacgtcca tcgcggcgct
 1081 cgtcaaggcg cgcatcatgg ctaagcttgc cttgtgccgt gacgcgcagc ccctcactt
 1141 cttccggagc gcaattcggg aaattgaggt tcaacagcac gccttccggc cagcccgcct
 1201 ccatcagcct cccgataagc tcaggcgcat gagcttccgc cgtttccac ggcacgatcc
 1261 ggcgatcgcc cgcatattca tattcctgcg acaaagcgat ggctcgcaca ccaagcaatg
 1321 tccctccat cgcaccggca accgtgcccg aataggtcac atcgtcgcc atgttcgcc
 1381 cggaattgac gccgagagg acgagatcgg gcgcgcccgg caatacatgg cgcaccccca
 1441 tgatgacgca atcggtcgga gtgccgcgca gggcaaaatg acgggcatcg atctggcgaa
 1501 ggcgaagcgg ctccgacagt gtcagtgagt gggcaagccc gctctggtcc gtttcagggg
 1561 ccaccaccca cacatcgtcg gagagcttgc gtgcaattcg ctccagaaca gcgagggctt
 1621 cagcgtggat accgtcatcg ttcgtcagca gaatacgcaa tttgtcactc cttcgccgaa
 1681 atggataaga cacttaagac actacagcgg ttccagttga aatgggatcg ttgaaactgc
 1741 tctctctttg ttctttcgca tgtccccaaa accggttccc acttttgggg gcatgctata
 1801 attccagatc aagcggcttt ttcgatccgc gtgaggccgc ccatatatgg ctgtaatgct
 1861 tcaggaatat gaatgctgcc gtcttcctgc tggtaatttt ccataaccgc aatcagcgcg
 1921 cgcccgacag cagcgcccga cccgttgagg gtgtgcacga agcgcgtgga tttttcgcct
 1981 tccgggcgat agcgggcatt catgcggcgg ccctggaaat caccgcaggt cgaacagctt
 2041 gaaatttcgc gataggtgtt ctgccccggc aaccagacct cgatatcata ggtccgctgt
 2101 gcgccaaagc ccatgtcgcc cgtgcaaagc acaacggtac ggaacggcag gcccagccgc
```

TABLE 5-continued

Nucleotide sequence encompassing two open reading frames of
the *Brucella melitensis* 16M genome (SEQ ID NO: 26).

```
2161  ttcagcactt cttccgcgca agccgtcatg cgctcatgct cggcaacgga gctttccgca
2221  tcggtgatcg ataccatctc cactttcagg aactgatgct ggcgcaacat gccgcgcgta
2281  tcgcgcccgg ccgaccccgc ttccgagcga aaacatgggg tcagcgccgt gaagcgcagc
2341  ggcagcccct tcatatcgac aatttcttcg gcaaccagat tggtgagcgg cacctccgcc
2401  gtcgggatca gccagcggcc atccgtcgtg cggaaaagat cttctgaaaa cttcggcaat
2461  tgccccgtgc catagaccgc ttcgtcgcgc accatcagcg gcggcatgac ttcggtataa
2521  ccgtgttctg tcgtgtgaag atcgagcatg aactggccaa gcgcgcgctc aagacgggcg
2581  agcgggcctt tcagcaccgt aaagcgcgca ccggcaagct tggccgcgcg ctcgaaatcc
2641  atgtatccaa gcgcctcgcc aagctcaaaa tgctctttcg gctggaagga gaaattgtgc
2701  gggttgccaa tgcggcgcag ctcaacattg tcgctttcat ccttgccgag cggcacatca
2761  tcaagcggaa tattgggaat ggtggacaat gcgtcgctca gttccttgct gaggcggcgc
2821  tcgtcttctt ccgcatgggc gagaaaatct tcagttcgc ccacttcggc cttcagcttt
2881  tcagccgtgc ccatgtcctt tgcggccatg gccttgccga tttccttcga ggcggcattg
2941  cggcgctcct gcgctgcctg caccttgccg acatgctcgc ggcgcttttc atccagcgca
3001  atcagttcgg acgaaagcgg agcagcccca cgctttgcga gcgccttgtc gagggtttcc
3061  gggttttcgc gaatccattt gatgtcgagc atggaaaaaa gccatttcgt gaaattgaac
3121  agaagcgagg ctaaacgatc ttcagcccca aagatgcctg acgtcagatc aggtggagga
3181  agcgttgtta tcagcgtcgg cagatgcctg cgcctcatcc cgcttcttct cgatcatgcg
3241  cgccagaaag atcgaaatct cgtaaagaag gatcgtcggc aaggcaagac cgatctggct
3301  cgccgggtcc ggcggggtca gcaccgcagc cgcgacgaag gcaatgacga tcgcatattt
3361  gcgcttgtcc ttcagccccg ccgaagtcac cagcccaca cgcgccatga ggctcgtcac
3421  caccggcaac tggaagacca ggcaaaagc aaagatggac gtcatgatga ggctcagata
3481  ttccgacact ttcggcagaa gcgaaatctg gacctcgccg ctgccgccgg tctgctgcat
3541  ggcgaggaag aaccacatca ccatgggcgt gaaaaagaaa tagacgagcg cgccgccgat
3601  caggaacaga atgggcgacg cgatcaggaa cggcagaaat gcagtgcgtt cgtgcttgta
3661  gagaccggga gccacgaatt tataaatctg tgcggcgatg accgggaggg ccagcacaat
3721  gccgccgaac atggccacct tcacctgcgt gaagaagaat tcctgaggtg cggtatagat
3781  caattccgcc ttggagcggt ccatgccggc ccagtcgatg gcccattgat acggcaccac
3841  aagcaggttg aagagctgtt ttgcgaaagc aaagcagaaa atgaatgcca cgaaaaaagc
3901  caggatagcc caaataaggc ggcggcgcag ttcgatcagg tgttcaagca gaggcgctgc
3961  gctctgttcg atttcatcct cgtcccggtt cacgctttgg ttcctgtctt cttgtggtc
4021  tttttaaccg gcgttgcggt cttgtctgcc gtcgcttgg gggtagctcc ggttttttg
4081  gcagtctttg tcgtcgtcgg tttcggcccg gcttttgcag ccggacgcgg tgatgttttc
4141  ctaggcttgg cgggttcttc gggcgcggtg atcattgta cgggaactgg cggcgcggga
4201  actggcgttc cgcccggctc aaccggcgtc gtaacctcac ccaccttgtt ctcggtgact
4261  ggcgacattg atgttgcgga ctggagacca gaccgcaaat cctcgccagc actgcgaatc
4321  gggtcaaaaa cctgtgtcag ccttgtgcgc ggatcaaggc ttctggcttc atcgatgatg
4381  gtcttgacgt cttcaagttc cgcctctttc aaggcctcgt tgaattgatg gcgaaactcg
4441  ttggcggtgg tgcgcatgcg tgcagtcgcc gcgaagcat tttcggcaaa
4501  tccttgggac cgaccaccac aatcatgaca attgcgataa tcagcagttc agaccaagcg
4561  atatcgaaca taatttgata ccttgcgctc tgcgcgcaca tcctgtctct tggcgaaaag
4621  ccgcactgcc cacaaacctg ccatgcgcgt tttcagccca tggcagttca tcccggaagg
4681  atcaggactt ggtggtcttc ttgacgtcct tgacgggttc ttccgctttg gcgtcgatcg
4741  tacgcggatc ttccttggcg tcttcgtcag ccatgccctg cttaaaattc ttgatacct
4801  tggcgacatc gcccatcagc tcggggatct tgccgcggcc gaacagaaga agcacaaccg
4861  ccagaacgat cagccagtgc cagatggaaa agctaccat attattcctc tcagtgccgc
4921  ccaaggcgcg gcatatgcct gctatctccg atacgattta agcgcttttca acaaatcttt
4981  caaacagaag tgtgatgatg aacggcttca aaccggatta attcgtcgca ggcagaaatt
5041  ttgttctatt ctccctggg tgcaagcaaa cccagtccct ccagatcaat atcctccagc
5101  gggtcctccc cttcggtcag ctcgtccggg tcgatattgg ggatcggtac ggcaaaactg
5161  gaaggaatgc gcgccgagag aagccctgcg ccgcgcaatt cctcaagacc gggcagatcg
5221  cggatttccg gcaggccaaa atggtcgagg aaagcgtcgg tggtgccata tgttaccggg
5281  cgccctggcg tgcgcctgcg cccgcgcagc ttgatccagc cggtttccat caagacatca
5341  agcgtcccct tggatgtttc cacgccgcga atatcctcaa gttcggcgcg tgtcaccggc
5401  tggtgatagg caatgatggc aagcacctcc atggtcgcgc gcgaaagctt gcgctgctga
5461  acagtctcgc ggttcatgat gaaggcgaga tctggcgcgg tgcgaaacgc ccagccactg
5521  cccaccttca caaaatgcac gcccctgccc tcgtaaacct tctggagatg gttcaaaacc
5581  ggagcaatat ccacattggc gggaagccgc tcggcaagtg cgcgctcgca aacaggctgc
5641  gaagacgcaa aaacaatcgc ctccacaatg cgggcaagct cggcaagcgt caccggcgag
5701  gcaggccccg ccttgctcttc ttccccaacg ccttccatat ccatcaaatc gcggcgctct
5761  gcttcaggca ttttcgtcct catcgaattc atcgagttcg cgggtcgcgc gcatatagat
5821  cggctcgaac ggagcgttct ggcgtacttc aagcttgcct tcgcgcacca gctcgaggca
5881  tgcggcgaaa gaactggcaa gcgccgacgc cctctcctgc ggagaaagtg cataatcgat
5941  caaaaaacgg tccagcgaaa cccagtcgcc caccgcgccc atcaggcgca caagcgccgt
6001  gcgtgcctcc ttgagggacc agacgctgcg ttttttctatc tgtacctggg aaaccgcctg
6061  gcgctggcgc tgcgacgcat aagcgctaag cagatcgtaa agcgttgcgg aaaaacggct
6121  ggcgcggtcc accaccacca tttccggcat gccgcgcggg aaaacatcgc ggccgagccg
6181  atgacgattg acgagtgccg ccgccgcatc gcgcatgcct tcaagccgtt tcaaccggaa
6241  ttgcagggag gcaacgagtt cctcgcccgt ggcgccatcg tcgccctgct gcttcgggat
6301  cagcagcttg gatttcgat aggcaagcca tgccgccata acgagataat cggcggcaag
6361  ctccagacgc agcgcgcgcg cctgctccac gaaaccgaga tattgttcgg caagcgccag
6421  cacggaaatg cgcgcaagat cgacgcgctg gttacgccga agatgcagaa gaaggtcgag
6481  cggaccttca aagccctgca catcgatcag cagtgacggc tcgcctgcgc ctcgcccggc
6541  ctcatttgc cacagggtat ccatcggcac gcgtgtgccg tcgtttccac ctgtatgtgc
6601  atccgatgct gccaagcctg tcgtcctgct gttgcccctg ccggcacaga ttctgccagc
6661  aggaacaagt ttatcaagtt ttgccgatta cgctatcggt tcaaacatgg cattgaattc
6721  ggcgcgcacc tcgtcctcgt cggaaagatc ggggtcgccc gcatagactt ccgccagttc
```

TABLE 5-continued

Nucleotide sequence encompassing two open reading frames of
the Brucella melitensis 16M genome (SEQ ID NO: 26).

```
 6781  ggcccggcgc tttgctttgc catccagaac cggcacacgg gcggcaacct ttaccagttc
 6841  ctccataacg cctgagcaat agagcacgat atcgcagccc gccgtaacga tgccgtcggt
 6901  tatatcgcca agatcgccgg acaatgcctt catggaaatg tcgtcactga tgacaaggcc
 6961  gtcgaacccg atcacatcgc gaatgatcgt attaataacc gtcggcgaaa gcgtggacgg
 7021  tctttccggg tcgatgcaat cgaacaccac atgggcggtc atgccatcg gcagatcatt
 7081  gagcgccttg aacggcacga aatcatgcgc aaccagttcg ttgagcgcaa cgctgacccg
 7141  cgccagttcc ttatgcgtat cggaaaaggc gcggccatgg cccggcatat gcttcacgac
 7201  gggaagaacg ccgccagcca gaagaccttc ggcgacgcg cgtcccattt ccgcaaccgc
 7261  atgggggttt tggaatagg cccgcattcc gatcacatca tgcgcgccct ccaccggcac
 7321  atccagaacc ggcaggcaat ccgcattgac gccgaccttc aacagatcga aagcatggag
 7381  ccgggcatgg agccaggcgg cacgcaaccc cttttccttg tcgcgtgcat agatcgcgcc
 7441  aatttcggac gcggacggat agttcggtac cagcggcggg cgaaggcgct gcacgcgccc
 7501  gccctcctga tcgatgaaaa ccggcgtctg tccagcccc gtcaggtcac gcagatgggc
 7561  ggtgagctcg ctcacctgtt cgaggctttc cacattgcga gcaaaaagaa tgaagcccca
 7621  cggggtttca tcccggaaga aggcaatctc gtccggggtg agcttcgtgc cggatatacc
 7681  ggcaatccat gccttgcact ctttcatgcg gcttttcctc gaattgtctt gctgaatcaa
 7741  actcgcctcc gccgggttta gccgaaaaaa cggccgcttg taggctgta ggctgtggtg
 7801  acgaattaac ttatggttcg gtatgaacga aaatgctcaa tagcccggca gatgcgaaaa
 7861  gggcggctga cgccgccctc aaatggctgg aaccttgctg gttgtttta ctgcgtcacg
 7921  aaacagcttc cgccagccga cttgagacgg ctgcaaagcg ccaatgcatc ttccttcgag
 7981  ccagcctgta cgcgaacacg gtaataggtg ccctttgccct gaatgtcggc gcgcttgata
 8041  tcgacgctat gaccgccaat cacactggca tatttctggg ctatgttggc ataggacttc
 8101  tgcgccagct cagcagaagg ctgcgaggca atctggatga aataaccacc cgccccggct
 8161  gccgatgcga cctgcggtgc agccgatgcc tgcgcgcgct gcggcacgtt accgacgata
 8221  ttgacgggct gttcagcggg gcgcgacggc acgatcggag cgcgggtcgg aaggcgtggg
 8281  gtctccggcg tcgcggattg ctgtgcctgt ggcgctggcg gttcatttcc tgccgcgagt
 8341  gcgccgattt catcccgtgc tgccggtgcg gcaggcggcg ccatattgtc ggctaccgac
 8401  ggctgtgctg catgtccgaa cgaaggctga atgatcgtgc catccgggcg aacgatcatc
 8461  gtttcgacct cacgcggctg gatcagcggt tcatgcgtgc cggaatgagc ctgttgcgca
 8521  tcgttctgcg gtacattgcc acccggttct tctgtggcat tatattcgct gtcatcggta
 8581  ccggaaatat cgaccggttc ttcaccggat gtaatcaggg ctttctgttc cgggttgttc
 8641  ggaagcgttc cggccacacg gtcatagacc gccttatcct ggttcggaac cgtggttccg
 8701  cccggatttt ccggctgcat cttgatgggc tggttatcgg cgcgaatcac aaccggctca
 8761  ccggagcctc cgccgccgag gaaatgatag ccgattccgc cgagcagaac cgccacaccg
 8821  gcaacacttg ccaaaatcaa gccacggcga ccacgaaccg ggcgattgcg gtaagcttcc
 8881  gccgcgccgc ccagatcgtc ttccgtcggc attgcggcgc gctcgccata atcgccgcct
 8941  tccatggtct gcgcaccctg cgcggcccag tgattgtaga aatcatcctg gctggcagtc
 9001  gttgcagcgg caggtgcagc ttcagacccg gcgcgtcggt aggaagcagc agccgctgcc
 9061  gccgcagcac ccaagccggc cgcggccatg cgctattcg gcatataggt cgatgcgctt
 9121  tcacggaaga tgtcctcaaa agccctgtcg gcttcgctct ggccttccgt gatctgcaca
 9181  ttctcatcaa caccaatcgt gctgaaaact tccgcgaact ccgcttccag ctcactgaga
 9241  ttggtgcccg cttcctcttc gccgtaattc acttccggca gatcgagcga atgcgtctgt
 9301  tcgaccttgt tttccgtgac cgtgagggtc tcaacctccg gtgcaggctc cggtgcgggc
 9361  atacgccgcg gagcctgcat gtcggtataa gcggcaaagg agacagcagg gcgataatcc
 9421  tgccggaat ggattgcgtg cgcataggct ggcgcgggag aagcttcttg ctcctcctca
 9481  tggagatcaa gttcaacatc ggtgaagaaa tcttcatcgt tgaaaaaatc ttcatccgca
 9541  gtatcggcga cgtctgcgtc gaatgtgtct ccagacggct cgaaaccgaa atcatcttcg
 9601  gtcaggctga tttcgtcgag ccccgacagg tcatcatccg tcgattcggc ggcggcagcc
 9661  gtttccggct ctgcttcaaa ggtaaaatcg tcctcaagcg aaaactcatc ctcgattggc
 9721  cggaacggat cctgggcaac aaaatcctgc acaataggcg cctggggcgt tttcagttgc
 9781  ggccccgagg agagcacacc gggggcggct acacccggcg caaaattgct gcgcggataa
 9841  tagggatagg ccggcgcctc gccagtgcgt gacgcatagc cctgcccggc atgggacgga
 9901  gcatccagat gcggttcgct gaccggcgct tccggttcgc cctgatgcgg ttgttccggc
 9961  gcgtaggaaa caggctcgac gtgatccgaa tagctgttcc gggatgccac aggctgcggc
10021  tcatcgccaa acagaaggtt ttccagctcg tcttcaagcg aaagcggttg ctgtgcaggc
10081  tcagccgcga aatgcgtagc gggagcatct acaggctgct gcgcattcca attattctgt
10141  gctggccagt cattctgttc cagcctgtca ttctgtgcag gccactcatc ctgtgcctgc
10201  caattgtcct gcacgccggt atcttcacgc caagcttgct cacccggctc aatggcaggc
10261  tgatagacgt tcggatcata ttcgcccgca tctgcctcta tcggctgctg gcgatcacca
10321  taagccgcag gtgatgccat atgggcgtgt cgctcgaat cacgagcctg cgaataatcg
10381  ttatagtcga attgcggaac gggctcggag cgatccacgt cctcgaactc gaaaatttcc
10441  ggtgacggtg ctgcttctgc cgagccaagg tcgagatcga attcttcttc cagcgcgcca
10501  gcgaacgcat cctcctccaa cggagactgc tcgccatagg cccgctcccc gtgcacgcca
10561  aaggttgcgg tcgaaacggt ttcgctatga gctgtaggct gcgtataatc gtcgaaatgc
10621  cccataagct cgcgctcaag atcgagaacg ggatcaaaag aggggtcatc ctgcgccgaa
10681  tcaaagcgcg gctctgctcg gccctgatcc tcgaattgac tgtcatggcg gcgctcattc
10741  cgagcgacgt tatcatcagc aggcgtgtcg aagtccataa tccgcgaaag ttccatcagc
10801  ggatcatctt cgtgcaccgg acgctcgccg taattacggg gatttgcact gctgtccgtc
10861  atggcgtgtt cctaactcaa accctggacg ccgcaagacg tctccataca ttgcatatta
10921  gcgaggcaat gtgggcaaaa gttgacggaa gtttcctgca caggaaggaa gatcc
```

TABLE 6

Nucleotide sequence encompassing four open reading frames
from the *Brucella melitensis* 16M genome (SEQ ID NO: 27).

```
LOCUS       AE009549   10209 bp   DNA   linear   BCT   20-MAR-2003
DEFINITION  Brucella melitensis 16M chromosome I, portion of section
            106 of 195 of the complete sequence.
ACCESSION   AE009549 AE008917

VERSION     AE009549.1  GI: 17983058

SOURCE      Brucella melitensis 16M

REFERENCE   1 (bases 1 to 10209)

AUTHORS     DelVecchio et al. 2002. The genome sequence of the
            facultative intracellular pathogen Brucella melitensis.
            Proc. Natl. Acad. Sci. USA 99: 443-448 (2002)

FEATURES         Location/Qualifiers
     source      1 . . . 4500 (excerpted herein)
                 /organism = "Brucella melitensis 16M"
                 /mol_type = "genomic DNA"
                 /strain = "16M"
     CDS         complement (159 . . . 1916)
                 /gene = "BMEI1089"
                 /EC_number = + 37 6.1.1.19"
                 /product = "ARGINYL-TRNA SYNTHETASE"
     CDS         complement (2138 . . . 3346)
                 /gene = "BMEI1090"
                 /EC_number = "3.1.5.1"
                 /codon_start = 1
                 /product = "DEOXYGUANOSINETRIPHOSPHATE
                 TRIPHOSPHOHYDROLASE"
                 /protein_id = "AAL52271.1"
                 /db_xref = "GI: 17983060"
     CDS         3513 . . . 3839
                 /gene = "BMEI1091"
                 /product = "HESB PROTEIN"
     CDS         complement (3920 . . . 4411)
                 /gene = "BMEI1092"
                 /product = "hypothetical protein"
                 /protein_id = "AAL52273.1"

ORIGIN
    1 tattagcgag gcaatgtggg caaaagttga cggaagtttc ctgcacagga aggaagatcc
   61 atgactttca atcatactga tcttccttca cattagtctt actgtcactc atccaaaggc
  121 gtctttcgac tttcagtact tcggacgacc gtgtaatcct agccgcatctc cgtaggagca
  181 tccgcgccga taatcgtcaa tcctgacgtc agcacatcgg aaacaacctg caccagccct
  241 agcctggcca gcgacaagtc tggatcgtta accttaataa aacgtaagtc cggattttcc
  301 gcgcctctgt tccattgcga atggaacgaa ctggcgaggt cgtagaggta gaaagccagg
  361 cgatgcggct cctgatgaat ggctgccgat tcgatcaggc gcgggtattc cgcaagcttg
  421 cgaacgagcg caatttcgct ctcgtcggtc agcttttcaa aatgcgaccc catggccacg
  481 cggtcaagat cgacaagccc aagctggtcc gcagcctgac ggaaaaccga atggcagcgc
  541 gcggaagcat attgcacata gaaaaccgga ttgtccttgg actgctccgt caccttgcg
  601 aagtcgaagt ccaatggcgc atcgttcttc cggtaaagca tcatgaagcg gaccggatcg
  661 cgaccgacct cgtccaccac atcgcgcagc gtaatgaact cgcctgcccg cttggacatg
  721 cgcaccggct cgccattgcg gaacagcttc acgagctggc acaggagcac ggtcaatttg
  781 gccttgccat cggaaacggc acgcgcaacg gcttccagac gcttgacata accgccatga
  841 tccgcgccga gcacatagat catctcattg aagccgtggt cgtacttgtc cttgaaatag
  901 gccacgtcac ccgcaaaata ggtgaacgag ccatcggact tcatcagcgg acggtcaata
  961 tcatcgccca cttccgtaga acggaacagc gtctgctcac ggtcttccca atcttccggc
 1021 aactgcccct tcggaggcgg cagcttgccc ttataaacat ggcccttgag cgtcagatca
 1081 ttgatcgcgt tacggatcgc gcgcgcatgg tcgacatgta gcttgcgctc ggaatagaag
 1141 acatcatgat gcacgttcag cgcgtcgaga tcagcgcgga tcattgccat catggcgtcg
 1201 atcgtgcggt ccttcacgat ggccagtgct tcggcttcag gcatttccag aagttttgtg
 1261 ccaaactcac cggcaagctc ctgcccgacc cgcacgagat aatcaccggg gtaaagcccc
 1321 gccggaatct cgccgatgct ttcgcccagt gcctcacgat agcgcagcat cacagagcag
 1381 gcgagaaacat cgatctgcgc gcccgcatcg ttgatgtaat attccttgac gacgtcatag
 1441 cccgcgaatt tcagcaggtt cgccagcaca tcacccacaa ccgcgccccg gcaatggccg
 1501 acatgcatcg ggcccgtagg gttggccgat acatattcga cattgacctt cttgcccgcg
 1561 ccaagcctgg agcggccaaa atccgttccc tcgttcagca tcaccaaaag ctcgcgctga
 1621 caatagctgg ccttgaggcg cagattgatg aagcccggac cggacgacatc gacggattcg
 1681 acatcctcat cggccttcag cgcctcggca atgcgggcag caagctcgcg cgggttctgg
 1741 ccgaccgcct tggaaagcac cattgcggca ttggtcgcga tatcgccatg cgaagcatcg
 1801 gcgggggct cgacacctat gcgtgaaagg tcaagttcac caccatcttt ttgcttcaga
 1861 tcaatatctt gcaacgtttt tttaatacgt gcatcgaaat ctgcaaagat attcatggtc
 1921 tgtcctgtca ggctagcgcg gttcctgttt taacagaatc gccggaacca ctctaactat
 1981 tgttttgtcg catttcccaa cgcaaaaccg tttcacactt ttggctcgaa aatactctaa
 2041 cgcctggatt tttttccagt tttcccggcg cgggttcatc caaaaaacgc ggatattcga
 2101 tgcatttgcg tatcgaagcc gcttcgtccg gcccgatta agctaaatcg ggggttcggt
```

TABLE 6-continued

Nucleotide sequence encompassing four open reading frames
from the *Brucella melitensis* 16M genome (SEQ ID NO: 27).

```
2161 caaacaatcg tcggtgttcg cgcacggcat aattatcagt catcccggcc agataatcgg
2221 ctacgcggcg tgcgagtgct gccttatcca gtgcctcaca gcccaaacgc cattcatcag
2281 gcatcaatga gggatcggtg aaacaggcat cgaagagatc ctgcacgatc ctgtcggctg
2341 cgtgcctgcg caccaccacg ctttcgtgaa aatagagatt cttgaacaaa aagcgcttca
2401 gcaccttttc ctcggcccgc atggcgtcgg aaaagccaac cagcgcgcgc ggctggttgt
2461 gcacgtcttc catcgttccg ggcctggcgg atgcaaggcg gcgctgcgcc tcctcgatca
2521 cgtcttccac catgatcgtg atctggcggc gcaccagttc gtgtccagtg cggacggggt
2581 cgagattggg ataacgtgtc cgcacaatat caagcagccg tttggcgagc ggtacttcgt
2641 ccagcgattc gagggtcaag agccctgccc gcaagccatc atcaatgtca tgcgcattgt
2701 aggcaatgtc gtcggcaatg gccgcgcatt gcgcctcaag gctcgcaaag cgtgaaagct
2761 ccagatcata gcgcgcgtta aaatccagaa tgggttgcgg aaccgggata tcgggatggg
2821 ctgcatatgg ccccagcaac gggccattat gcttcaccag accttccagc gtttcccacg
2881 aaaggttgag gccatcgaaa tcagcgtagc gatgctcaag cttcgtgacg atcctgagcg
2941 actgggcatt atggtcgaaa ccgccgaaat tcttcatgcg ctcgttgagt gcgtcctcgc
3001 cggtatggcc gaagggcgtg tggccgaaat catgaacgag agcgacagct tcagcgaggt
3061 cttcatccag gcgcagcgcg cgcgccagcg cccgcgcaat ctgcgccacc tcgatggtgt
3121 gcgtcagcct cgtgcggtaa tgatcgccct catgcgcgat gaaaacctgc gtcttgtgct
3181 ttaaacgccg gaaagccgtg gagtggataa tacggtcacg gtcccgctgg aacggcgtgc
3241 gggtcgggct ttccggttcc ggcaccagcc ggccacggct gaaagcagga ttgctggcat
3301 aaggcgcacg ttcgcgataa ccgaagccta ttccttccag cgacattgcg atgttttcct
3361 cactgtaata tgattacgtc aaattggtgc gtcattgact tccgcaacct gcgttcatag
3421 ctatcagcta aacatgaagg caagtacgcg gctatcggaa aatctcaaga acgcataacc
3481 cgatccccgt ccctgcaaac ggaacaaggc aaatgacagg cattaccgtt tcagattccg
3541 ctgccaggcg gatcgccaaa attctcgatt cggagccggg aaagaccgcg cttcgcgttt
3601 ctgtcgaagg tggcggctgc tccggctttt cctataaata tgacctcgtc gacgcacaga
3661 ccgaggatga catcgtcatc gaaaaactcg gcgccagagt gctgattgat tccatctccg
3721 tgccttatat ggacggctct gaaattgatt tcgtcgatga tctgatgggg caatcattcc
3781 agatccgcaa ccccaatgcg accgcttcct gcggctgcgg caccagcttc gcgatctgag
3841 cggcgcaaca aaacccgtga tgcaaaaccg gcggccagat ggccgccgtt ttttttaacca
3901 tggcaacaag cggacagttt cagactttca ctgaagcaac ggtcgcttcg atgtggtcca
3961 ccagcgcatc ttgcaggcca agccgcccgg caagcatatc cagatagccg cgttcggcgc
4021 ggttatctgg atcgatagcc agccgcgatg ccgtataaag ttcaactttc tgctcttccg
4081 tctgcgctgc ggcaaccagc acatcgagat cgacgggttc ggccagttcc cttgcaagga
4141 aggcctcagc ctcgtcgtcc agaccggaaa tcttcacctt ttccatgatg cgggcacgtt
4201 cggcatcatc aatataacca tcagccctgg cggcggcgat catggcctga accagcgtca
4261 gcgcgaaact attgctcatc gcgggagaat gcggatggaa gggtgaatcg gccggtggcg
4321 ccggaagaag ctccggctct tttgccaccg gctgttccgc ctcctgcggg gcctgaccgg
4381 acttataatt cttgtaggca agatagccca atccggctat ggcggcgatg ccgccgacag
4441 ttgctacatt gccagcaagt ttgcggcccg ttttcgtgcc aaaaatggct gcggctatgg
```

TABLE 7

Coding sequence of gale-like coding sequence of
B. melitensis 16M (SEQ ID NO: 28).

atgacaattcttgtaacaggtggtgctggctatatcggctcccacacgtg tgtgcagttgatcgaggcaggccatgaagtggttgtggtcgataatttcg acaacagccatcctgaggcactgcatcggattgaaaagatcacgggccgc gcgccgcgccgcgaaccgggcgatattcgcgatcgcgcccttatggaaca gatgatcaaacgccataaatgcactgcggttatccattttgccgggctga aggccgtgggtgaatcgagcgaaaagccgctgctctattatgattgcaat gtgctgggcacacttcggcttctgcaggccatggaagcgacaggcgtgaa gaagctcgttttcagctcttcggccaccgtctatggcgaccggataaac tgccgatcaccgaagatcagcccctttcggccaccaatccctatggccgg accaagcttgtcatcgaagacatgctgcgcgaccttataacagtgacaa tagctgggcgattgcgattctgcgctatttcaatcctgtcggcgctcatg aaagcgggcttatcggtgaagacccgaagggtattcccaacaatctgatg cccattattgctcaggtcgcaactggacgacgcgaaaagctgaacatctg gggcaacgactatccgacaccggatggcaccggcgtacgcgactatatcc atgtcaacgatctggctgccgggcacctcaaggccctgaaaaagctggat aagcccaagtgcttcgccgtcaatcttggaacggggcagggctatagtgt tcttgatgtgatcaaggcgtttgaacatgtctccaatcgcgagatcaaat atgagattgcgccgcgccgtcccggcgatgttgccgaatgctatgccgat cccggctttgcaaagaaatttctgggctggtcggctgagaaaaacctgcg tgaaatgtgtcaggacatgtggaactggcaatcgaaaaatccgaacggct acgaataa Although the description herein contains many specific examples and descriptions, these should not be construed as limiting the scope of the invention but as merely providing illustrations of some of the presently preferred embodiments of the invention. For example, thus the scope of the invention should be determined by the appended claims and their equivalents, rather than by the examples given.

BIBLIOGRAPHIC CITATIONS

1. Adhya, S., 1987. The galactose operon. In: Neidhardt, F. C., Ingraham, J. L., Low, K. B., Magasanic, B., Schaechter, M., Umbarger, H. E. (Eds.), *Escherichia coli* and *S. typh-*

1. *imurium* cellular and molecular biology. Am. Soc. Microbiol. Press, Washington D.C., pp. 1503-1512.
2. Alton, G. G., S. S. Elberg, and D. Crouch. 1967. Rev. 1 *Brucella melitensis* vaccine. The stability of the degree of attenuation. J. Comp. Pathol. 77:293-300.
3. Arellano-Reynoso B, N. Lapaque, S. Salcedo, G. Briones, A. E. Ciocchini, R. Ugalde, E. Moreno, I. Moriyon, and J. P. Gorvel. 2005. Cyclic beta-1,2-glucan is a *Brucella* virulence factor required for intracellular survival. Nat. Immunol. 6:618-625.
4. Blasco, J. M. 1997. A review of the use of *B. melitensis* Rev 1 vaccine in adult sheep and goats. Prev. Vet. Med. 31:275-283.
5. Boschiroli, M. L., S. Ouahrani-Bettache, V. Foulongne, S. Michaux-Charachon, G. Bourg, Allardet-Servent, C. Cazevieille, J. P. Liautard, M. Ramuz, and O'Callaghan. 2002. The *Brucella suis* virB operon is induced intracellularly in macrophages. Proc. Natl. Acad. Sci. USA 99:1544-1549.
6. Braun, W. and A. E. Bonestell. 1947. Independent variation of characteristics in *Brucella abortus* variants and their detection. Am. J. Vet. Res. 8: 386-390.
7. Celli, J., C. de Chastellier, D. M. Franchini, J. Pizarro-Cerda, E. Moreno, and J. P. Gorvel. 2003. *Brucella* evades macrophage killing via VirB-dependent sustained interactions with the endoplasmic reticulum. J. Exp. Med. 198: 545-556.
8. Celli, J., and J. P. Gorvel. 2004. Organelle robbery: *Brucella* interactions with the endoplasmic reticulum. Curr Opin Microbiol. 7:93-97.
9. Comerci, D. J., M. J. Martinez-Lorenzo, R. Sieira, J. P. Gorvel, and R. A. Ugalde. 2001. Essential role of the VirB machinery in the maturation of the *Brucella abortus*-containing vacuole. Cell. Microbiol. 3:159-168.
10. Contag, C. H., P. R. Contag, J. I. Mullins, S. D. Spilman, D. K. Stevenson, and D. A. Benaron, 1995. Photonic detection of bacterial pathogens in living hosts. Mol. Microbiol. 18:593-603.
11. Corbel, M. J. 1997. Brucellosis: an overview. Emerg. Infect. Dis. 3:213-221.
12. DelVecchio, V. G., V. Kapatral, R. J. Redkar, G. Patra, C. Mujer, T. Los, N. Ivanova, I. Anderson, A. Bhattacharyya, A. Lykidis, G. Reznik, L. Jablonski, N. Larsen, M. D'Souza, A. Bernal, M. Mazur, E. Goltsman, E. Selkov, P. H. Elzer, S. Hagius, D. O'Callaghan, J. J. Letesson, R. Haselkorn, N. Kyrpides, and R. Overbeek. 2002. The genome sequence of the facultative intracellular pathogen *Brucella melitensis*. Proc. Natl. Acad. Sci. USA 99:443-448.
13. Elberg, S. S., and K. Faunce Jr. 1957. Immunization against *Brucella* infection. VI. Immunity conferred on goats by a nondependent mutant from a streptomycin-dependent mutant strain of *Brucella melitensis*. J. Bacteriol. 73:211-217.
14. Foulongne, V., G. Bourg, C. Cazevieille, S. Michaux-Charachon, and D. O'Callaghan. 2000. Identification of *B. suis* genes affecting intracellular survival in an in vitro human macrophage infection model by STM mutagenesis. Infect. Immun. 68:1297-1303.
15. Fry, B. N., S. Feng, Y. Y. Chen, D. G. Newell, P. J. Coloe, and V. Korolik. 2000. The galE gene of *Campylobacter jejuni* is involved in lipopolysaccharide synthesis and virulence. Infect. Immun. 68:2594-601.
16. Hardy, J., K. P. Francis, M. DeBoer, P. Chu, K. Gibbs, and C. H. Contag. 2004. Extracellular replication of *Listeria monocytogenes* in the murine gall bladder. Science 303: 851-853.
17. Hone, D., R. Morona, S. Attridge, and J. Hackett. 1987. Construction of defined galE mutants of *Salmonella* for use as vaccines. J. Infect. Dis. 156:167-74.
18. Hong, P. C., R. M. Tsolis, and T. A. Ficht. 2000. Identification of genes required for chronic persistence of *Brucella abortus* in mice. Infect. Immun. 68:4102-4107.
19. Houng, H. S., D. J. Kopecko, and L. S. Baron. 1990. Molecular cloning and physical and functional characterization of the *Salmonella typhimurium* and *Salmonella typhi* galactose utilization operons. J. Bacteriol. 172:4392-8.
20. Jimenez de Bagues, M. P., A. Gross, A. Terraza, and J. Dornand. 2005. Regulation of the mitogen-activated protein kinases by *Brucella* spp. expressing a smooth and rough phenotype: relationship to pathogen invasiveness. Infect. Immun. 73:3178-3183.
21. Ko, J., A. Gendron-Fitzpatrick, and G. A. Splitter. 2002. Susceptibility of IFN regulatory factor-1 and IFN consensus sequence binding protein-deficient mice to brucellosis. J. Immunol. 168:2433-2440.
22. Ko, J., A. Gendron-Fitzpatrick, T. A. Ficht, and G. A. Splitter. 2002. Virulence criteria for *Brucella abortus* strains as determined by interferon regulatory factor 1-deficient mice. Infect. Immun. 70:7004-7012.
23. Ko, J., and G. A. Splitter. 2003. Molecular host-pathogen interaction in brucellosis: current understanding and future approaches to vaccine development for mice and humans. Clin. Microbiol. Rev. 16:65-78.
24. Kohler, S., V. Foulongne, S. Ouahrani-Bettache, G. Bourg, J. Teyssier, M. Ramuz, and J. P. Liautard. 2002. The analysis of the intramacrophagic virulome of *Brucella suis* deciphers the environment encountered by the pathogen inside the macrophage host cell. Proc. Natl. Acad. Sci. USA 99:15711-15716.
25. Kovach, M. E., P. H. Elzer, D. S. Hill, G. T. Robertson, M. A. Farris, R. M. Roop R M 2nd, and K. M. Peterson. 1995. Four new derivatives of the broad-host-range cloning vector pBBR1MCS, carrying different antibiotic-resistance cassettes. Gene. 166:175-176.
26. Lestrate, P., R. M. Delrue, I. Danese, C. Didembourg, B. Taminiau, P. Mertens, X. De Bolle, A. Tibor, C. M. Tang, and J. J. Letesson. 2000. Identification and characterization of in vivo attenuated mutants of *Brucella melitensis*. Mol. Microbiol. 38:543-551.
27. Lapaque, N, I. Moriyon, E. Moreno, and J. P. Gorvel. 2005. *Brucella* lipopolysaccharide acts as a virulence factor. Curr. Opin. Microbiol. 8:60-66.
28. Martinez de Tejada G, J. Pizarro-Cerda, E. Moreno, and I. Moriyon. 1995. The outer membranes of *Brucella* spp. are resistant to bactericidal cationic peptides. Infect. Immun. 63:3054-3061.
29. Maskell, D. J., M. J. Szabo, M. E. Deadman, and E. R. Moxon. 1992. The gal locus from *Haemophilus influenzae*: cloning, sequencing and the use of gal mutants to study lipopolysaccharide. Mol. Microbiol. 6:3051-63.
30. Monreal, D., M. J. Grillo, D. Gonzalez, C. M. Marin, M. J. De Miguel, I. Lopez-Goni, J. M. Blasco, A. Cloeckaert, and I. Moriyon. 2003. Characterization of *Brucella abortus* O-polysaccharide and core lipopolysaccharide mutants and demonstration that a complete core is required for rough vaccines to be efficient against *Brucella abortus* and *Brucella ovis* in the mouse model. Infect. Immun. 71:3261-71.
31. Moriyón, I., M. J. Grilló D. Monreal, D. González, C. Marín, I. López-Goñi, R. C. Mainar-Jaime, E. Moreno and J. M. Blasco. 2004. Rough vaccines in animal brucellosis: Structural and genetic basis and present status. Vet. Res. 35:1-38.
32. Metzger, M., P. Bellemann, P. Bugert, and K. Geider. 1994. Genetics of galactose metabolism of *Erwinia amylovora* and its influence on polysaccharide synthesis and virulence of the fire blight pathogen. J. Bacteriol. 176:450-9.
33. Naroeni, A. and F. Porte. 2002. Role of cholesterol and the ganglioside GM (1) in entry and short-term survival of *Brucella suis* in murine macrophages. Infect. Immun. 70:1640-1644.
34. O'Callaghan, D., C. Cazevieille, A. Allardet-Servent, M. L. Boschiroli, G. Bourg, V. Foulongne, P. Frutos, Y. Kulakov, and M. Ramuz. 1999 homologue of the *Agrobacterium tumefaciens* VirB and *Bordetella pertussis* Ptl type IV secretion systems is essential for intracellular survival of *Brucella suis*. Mol. Microbiol. 33:1210-1220.
35. Pei, J. and T. A. Ficht. 2004. *Brucella abortus* rough mutants are cytopathic for macrophages in culture. Infect. Immun. 72:440-450.

36. Plommet, M. 1991. Minimal requirements for growth of *Brucella suis* and other *Brucella* species. Zentralbl. Bakteriol. 275:436-450.

37. Porte, F., A. Naroeni, S. Ouahrani-Bettache, and J. P. Liautard. 2003. Role of the *Brucella suis* lipopolysaccharide O antigen in phagosomal genesis and in inhibition of phagosome-lysosome fusion in murine macrophages. Infect. Immun. 71:1481-1490.

38. Petrovska, L., R. G. Hewinson, G. Dougan, D. J. Maskell, and M. J. Woodward. 1999. *Brucella melitensis* 16M: characterisation of the galE gene and mouse immunisation studies with a galE deficient mutant. Vet. Microbiol. 65:21-36.

39. Pierson, D. E., and S. Carlson. 1996. Identification of the galE gene and a galE homolog and characterization of their roles in the biosynthesis of lipopolysaccharide in a serotype 0:8 strain of *Yersinia enterocolitica*. J. Bacteriol. 178: 5916-24.

40. Rajashekara, G., D. A. Glover, M. Krepps and G. A. Splitter. 2005. Temporal analysis of pathogenic events in virulent and avirulent *Brucella melitensis* infections. Cellular Microbiol. 10:1459-1473.

41. Rittig, M. G., A. Kaufmann, A. Robins, B. Shaw, H. Sprenger, D. Gemsa, V. Foulongne, B. Rouot, and J. Dornand. 2003. Smooth and rough lipopolysaccharide phenotypes of *Brucella* induce different intracellular trafficking and cytokine/chemokine release in human monocytes. J. Leukoc. Biol. 74:1045-55.

42. Robertson, B. D., M. Frosch, and J. P. van Putten. 1993. The role of galE in the biosynthesis and function of gonococcal lipopolysaccharide. Mol. Microbiol. 8:891-901.

43. Schurig, G. G., N. Sriranganathan, and M. J. Corbel. 2002. Brucellosis vaccines: past, present and future. Vet. Microbiol. 90:479-96.

44. Taniguchi T, K. Ogasawara, A. Takaoka, and N. Tanaka. 2001. IRF family of transcription factors as regulators of host defense. Annu. Rev. Immunol. 19:623-55.

45. Unsworth, K. E., and D. W. Holden. 2000. Identification and analysis of bacterial virulence genes in vivo. Philos. Trans. R. Soc. Lond. B. Biol. Sci. 355:613-22.

46. Young, E. J. 1995. An overview of human brucellosis. Clin. Infect. Dis. 21:283-289.

We claim:

1. An isolated attenuated strain of *Brucella melitensis* in which there is a polar insertion mutation or a deletion mutation which functionally inactivates or prevents expression of a gene encoding deoxyguanosinetriphosphate triphosphohydrolase, wherein said gene, prior to inactivation, comprises the complement of the sequence set forth in nucleotides 2138-3346 of SEQ ID NO:27.

2. The isolated attenuated strain of claim 1, wherein said strain is a *Brucella melitensis* 16M strain.

3. The isolated attenuated strain of *Brucella melitensis* of claim 2, wherein said attenuated mutant is GR026 (ATCC Accession No. PTA-11877) or *Brucella melitensis* GR01090Δ (ATCC Accession No. PTA-11878).

4. The isolated attenuated strain of claim 1, wherein said mutant strain expresses a listeriolysin 0 gene from *Listeria monocytogenes*.

5. An immunogenic composition comprising live cells of at least one isolated attenuated mutant strain of the *Brucella melitensis* of claim 1 and a pharmaceutically acceptable carrier.

6. The immunogenic composition of claim 5, wherein said isolated attenuated mutant strain is Brucella melitensis GR026 (ATCC Accession No. PTA-11877) or *Brucella melitensis* GR01090A (ATCC Accession No. PTA-11878).

7. A method of inducing an immune response against *Brucella* infection by administering an effective amount of the immunogenic composition of claim 5.

8. The method of claim 7 wherein said isolated attenuated mutant strain is *Brucella melitensis* GR026 (ATCC Accession No. PTA-11877) or *Brucella melitensis* GR01090Δ (ATCC Accession No. PTA-11878).

9. A method of inducing an immune response against *Brucella* infection by administering an effective amount of an immunogenic composition comprising cells of at least one isolated attenuated mutant strain of the *Brucella melitensis* GR026 (ATCC Accession No. PTA-11877) or GR01090Δ (ATCC Accession No. PTA-11878) and a pharmaceutically acceptable carrier.

* * * * *

UNITED STATES PATENT AND TRADEMARK OFFICE
CERTIFICATE OF CORRECTION

PATENT NO. : 8,075,879 B2  Page 1 of 1
APPLICATION NO. : 12/580213
DATED : December 13, 2011
INVENTOR(S) : Rajashekara et al.

It is certified that error appears in the above-identified patent and that said Letters Patent is hereby corrected as shown below:

Claim 3 (Col. 61, line 46), please delete "GR01090Δ" and replace with --GR-1090Δ--.

Claim 4 (Col. 61, line 48), please delete "listeriolysin 0" and replace with --listeriolysin O--.

Claim 6 (Col. 62, line 36), please delete "GR01090A" and replace with --GR-1090Δ--.

Claim 8 (Col. 62, line 42), please delete "GR01090Δ" and replace with --GR-1090Δ--.

Claim 9 (Col. 62, line 48), please delete "GR01090Δ" and replace with --GR-1090Δ--.

Signed and Sealed this
Third Day of July, 2012

David J. Kappos
*Director of the United States Patent and Trademark Office*